(12) United States Patent
Mizoguchi et al.

(10) Patent No.: US 11,140,318 B2
(45) Date of Patent: Oct. 5, 2021

(54) LASER ENDOSCOPE DEVICE

(71) Applicant: Mie University, Tsu (JP)

(72) Inventors: Akira Mizoguchi, Mie (JP); Koji Tanaka, Mie (JP); Yuji Toiyama, Mie (JP); Kyosuke Tanaka, Mie (JP); Shujie Wang, Mie (JP); Aika Kaito, Mie (JP); Kousyoku Sai, Mie (JP); Kazushi Kimura, Mie (JP)

(73) Assignee: Mie University, Mie (JP)

( * ) Notice: Subject to any disclaimer, the term of this patent is extended or adjusted under 35 U.S.C. 154(b) by 503 days.

(21) Appl. No.: 15/999,626

(22) PCT Filed: Feb. 23, 2017

(86) PCT No.: PCT/JP2017/006962
§ 371 (c)(1),
(2) Date: Aug. 20, 2018

(87) PCT Pub. No.: WO2017/146184
PCT Pub. Date: Aug. 31, 2017

(65) Prior Publication Data
US 2021/0227133 A1 Jul. 22, 2021

(30) Foreign Application Priority Data
Feb. 23, 2016 (JP) .............................. JP2016-032520

(51) Int. Cl.
*G01N 1/30* (2006.01)
*H04N 5/232* (2006.01)
(Continued)

(52) U.S. Cl.
CPC ..... *H04N 5/23238* (2013.01); *A61B 1/00009* (2013.01); *A61B 1/00082* (2013.01);
(Continued)

(58) Field of Classification Search
CPC ....... H04N 5/23238; H04N 2005/2255; H04N 13/207; H04N 5/2254; H04N 9/07;
(Continued)

(56) References Cited

U.S. PATENT DOCUMENTS

2002/0135694 A1* 9/2002 Williams ............. A61B 1/0615
348/375
2003/0107652 A1* 6/2003 Williams ............... A61B 1/127
348/207.99
(Continued)

FOREIGN PATENT DOCUMENTS

JP 2006-187386 A 7/2006
JP 2009-545737 A 12/2009
(Continued)

*Primary Examiner* — Howard D Brown, Jr.
(74) *Attorney, Agent, or Firm* — Foley & Lardner LLP

(57) ABSTRACT

The present invention is provided with an imaging unit (10) that has an imaging head (11) to be inserted into the digestive tract (112) and images a living body by applying a laser to the digestive tract (112) via the imaging head (11); a control unit (50) for controlling the imaging head (11) to move inside the digestive tract (112); and an image processing unit (70) for processing an image captured by the imaging unit (10). The imaging unit (10) captures a plurality of imaging regions (P) to be imaged along with the movement of the imaging head (11) such that a portion of adjacent imaging regions (P1, P2) overlap, and the image processing unit (70) overlaps regions (Pa) in which the plurality of imaging regions (P1, P2) are overlapped to generate a composite image.

17 Claims, 56 Drawing Sheets

(51) Int. Cl.

| | |
|---|---|
| *A61B 1/273* | (2006.01) |
| *A61B 1/06* | (2006.01) |
| *H04N 5/225* | (2006.01) |
| *A61B 1/00* | (2006.01) |
| *A61B 5/00* | (2006.01) |
| *H04N 13/207* | (2018.01) |
| *H04N 9/07* | (2006.01) |
| *A61K 49/00* | (2006.01) |
| *A61B 1/04* | (2006.01) |
| *A61B 1/045* | (2006.01) |

(52) U.S. Cl.
CPC .......... *A61B 1/00193* (2013.01); *A61B 1/042* (2013.01); *A61B 1/045* (2013.01); *A61B 1/063* (2013.01); *A61B 1/273* (2013.01); *A61B 5/0068* (2013.01); *A61B 5/0084* (2013.01); *A61B 5/4887* (2013.01); *A61K 49/006* (2013.01); *H04N 5/2254* (2013.01); *H04N 5/2256* (2013.01); *H04N 9/07* (2013.01); *H04N 13/207* (2018.05); *H04N 2005/2255* (2013.01)

(58) Field of Classification Search
CPC .... H04N 5/2256; A61B 5/0068; A61B 1/063; A61B 5/0084; A61B 1/042; A61B 1/273; A61B 1/00082; A61B 1/045; A61B 5/4887; A61B 1/00009; A61B 1/00193; A61K 49/006
See application file for complete search history.

(56) References Cited

U.S. PATENT DOCUMENTS

| | | | |
|---|---|---|---|
| 2003/0142206 A1* | 7/2003 | Williams | H04N 7/183 |
| | | | 348/66 |
| 2009/0326359 A1 | 12/2009 | Hendriks et al. | |
| 2016/0041100 A1* | 2/2016 | Mizoguchi | C09B 11/26 |
| | | | 435/29 |
| 2016/0299170 A1* | 10/2016 | Ito | A61B 1/00177 |
| 2018/0020932 A1* | 1/2018 | Chen | A61B 1/00009 |
| | | | 600/479 |
| 2018/0368656 A1* | 12/2018 | Austin | A61B 90/20 |
| 2019/0285638 A1* | 9/2019 | Mizoguchi | A61B 1/00 |

FOREIGN PATENT DOCUMENTS

| WO | WO 2014/157645 A1 | 10/2014 |
|---|---|---|
| WO | WO 2014/157703 A1 | 10/2014 |

* cited by examiner

[Figure 1]
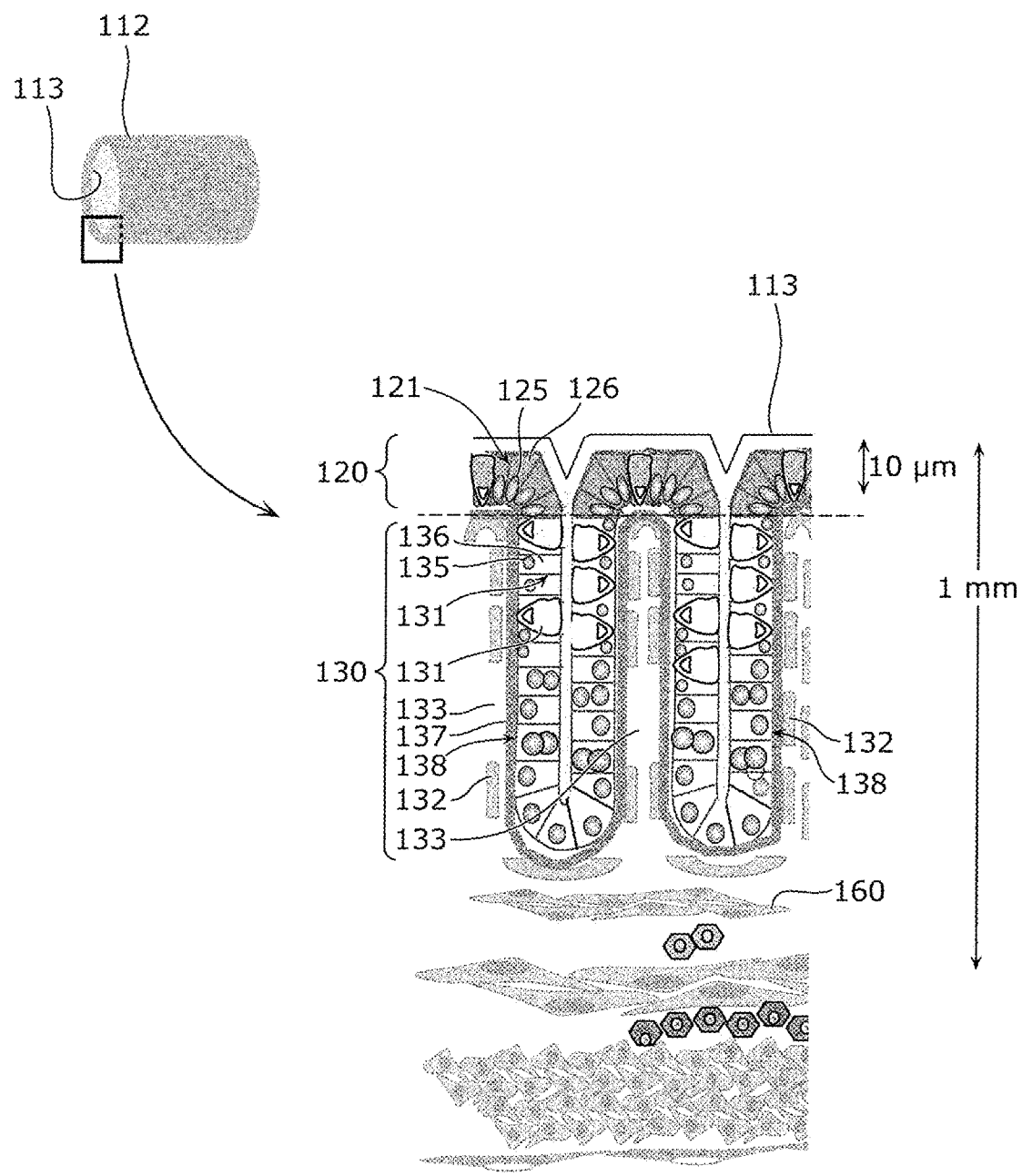

[Figure 2]
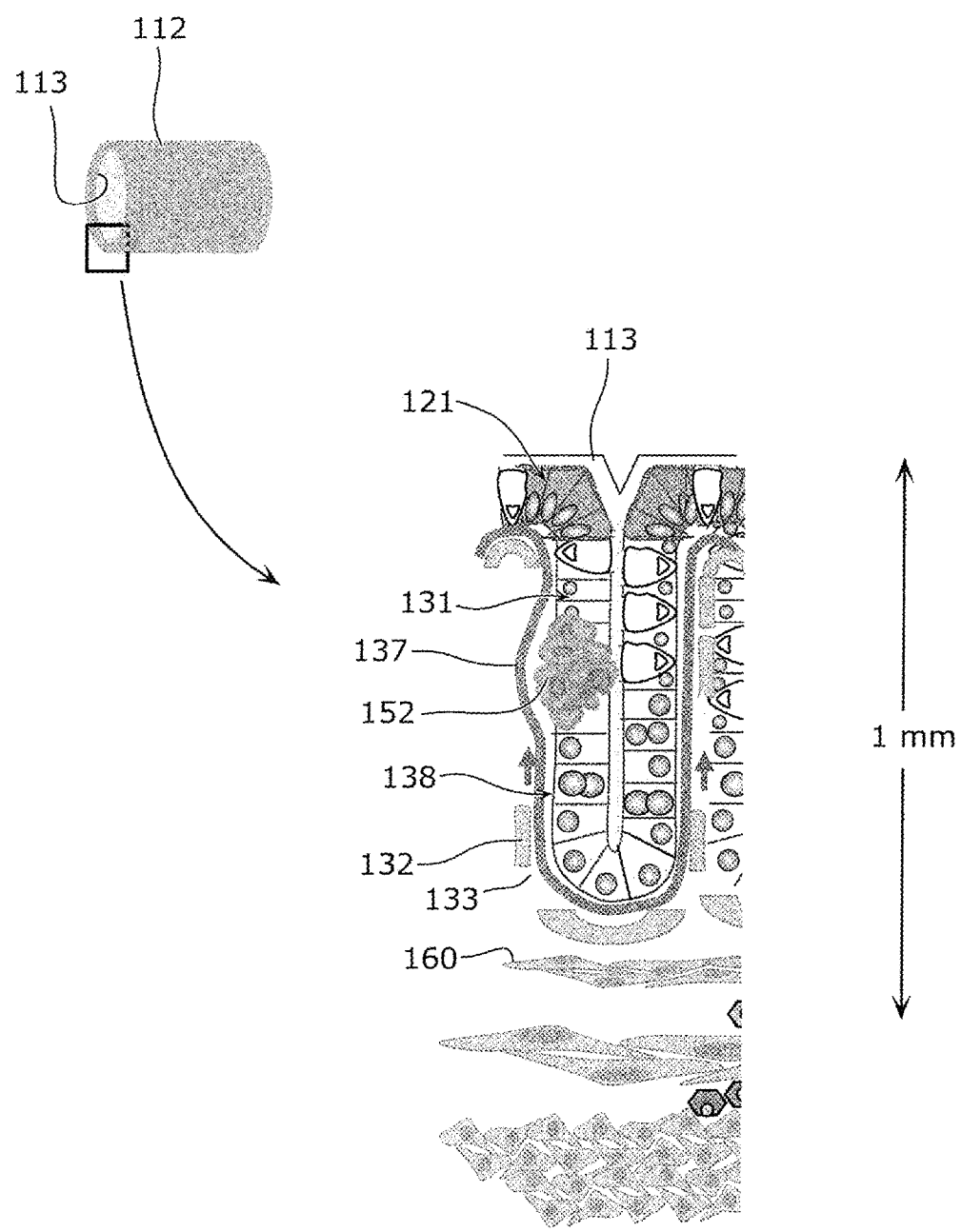

[Figure 3]
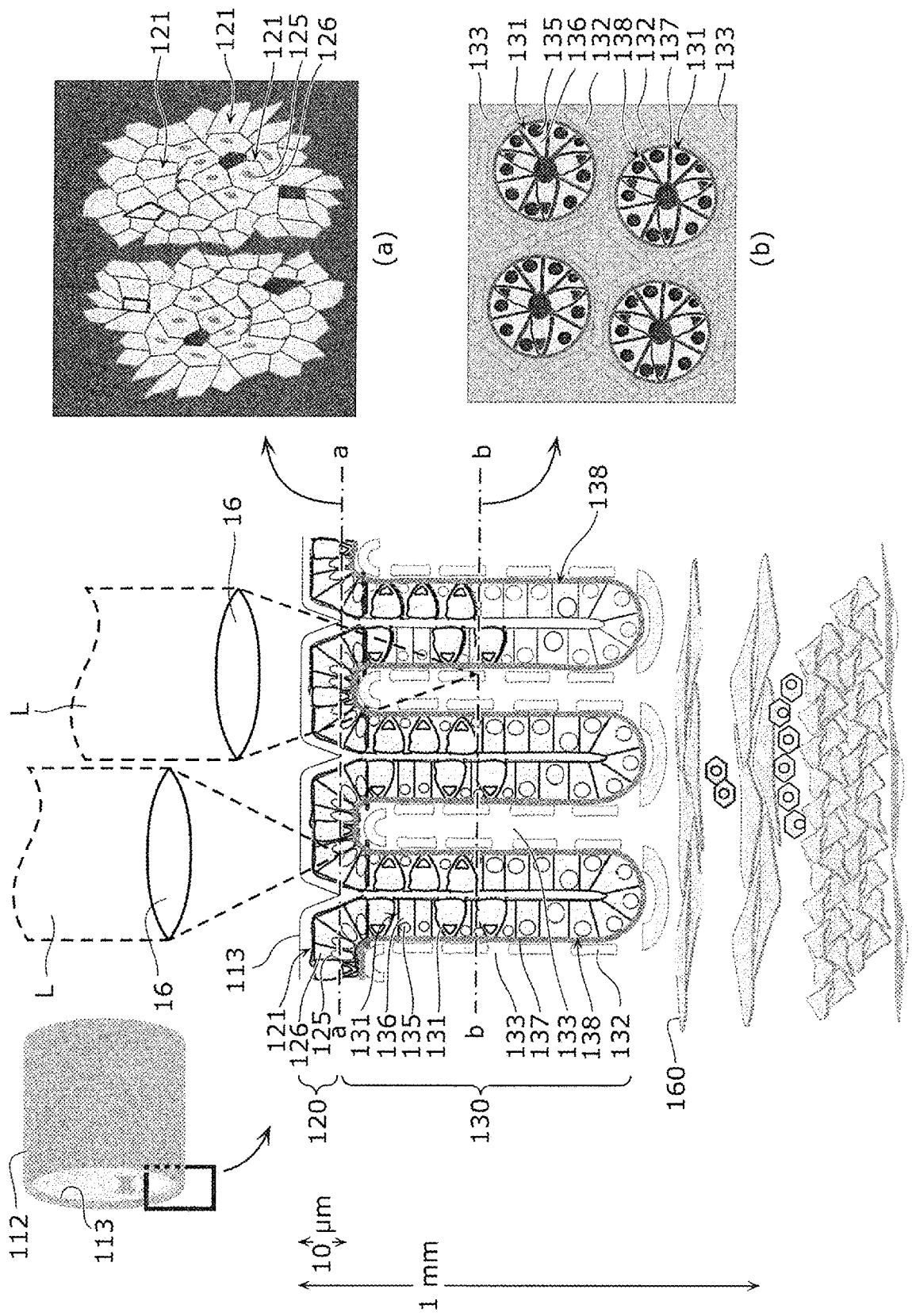

[Figure 4]
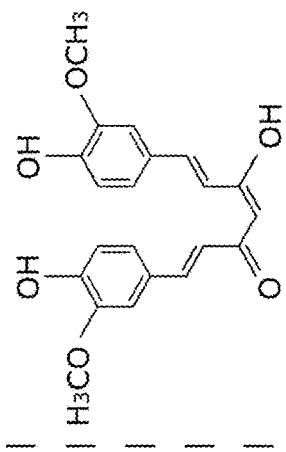
CURCUMIN
(TURMERIC DYE)
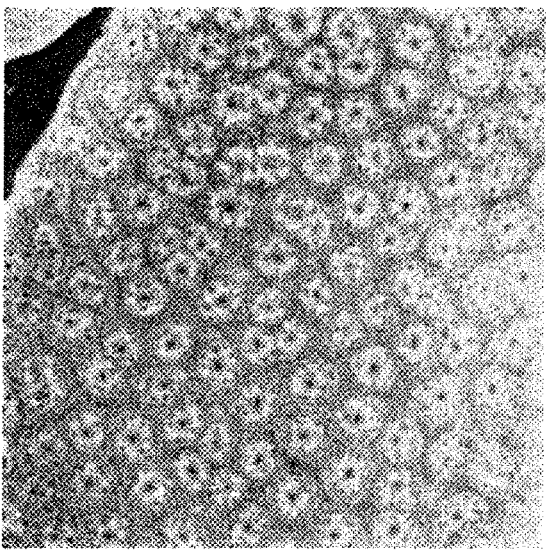
LASER WAVELENGTH 780 nm
(OBJECTIVE LENS 10 TIMES)
(a)
LASER WAVELENGTH 780 nm
(OBJECTIVE LENS 25 TIMES)
(b)

[Figure 5]
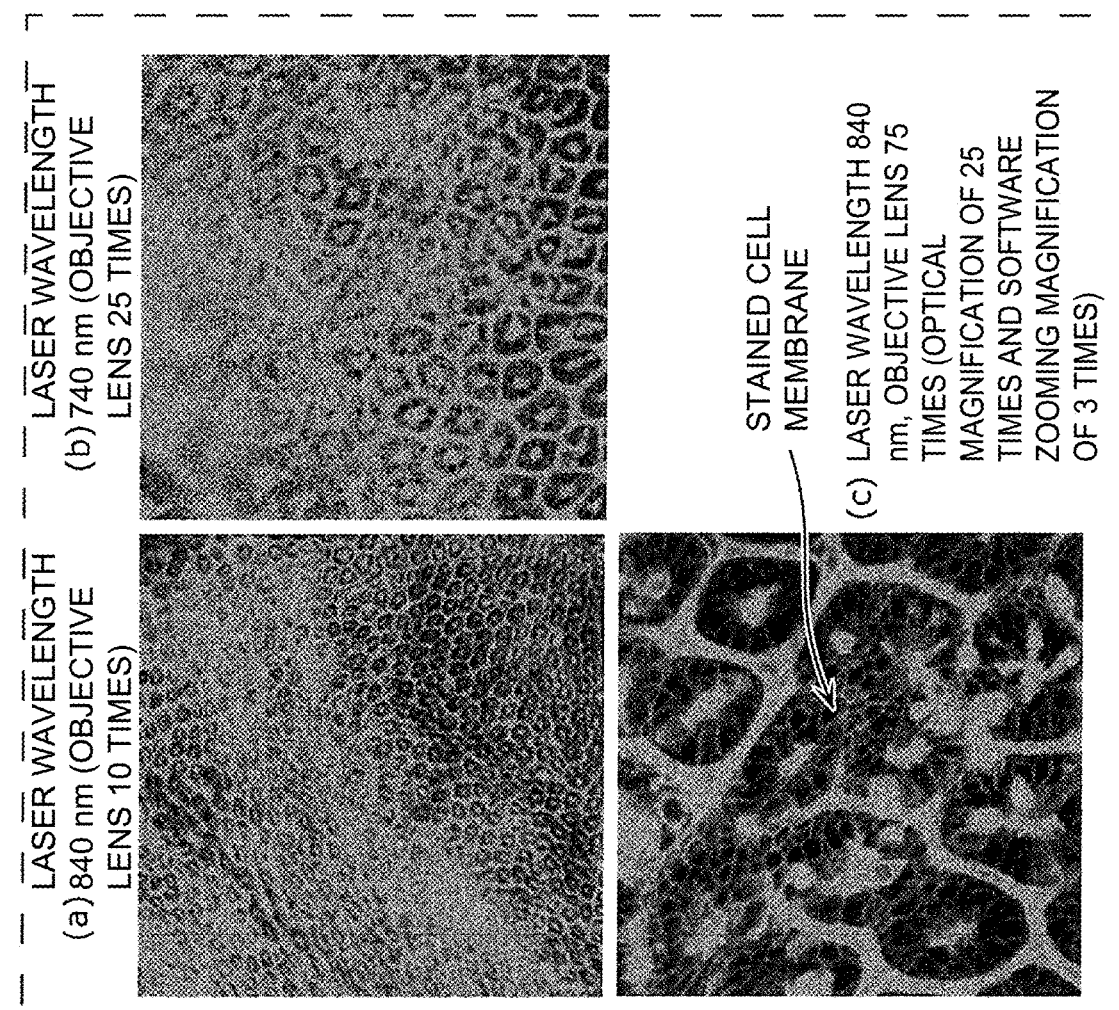
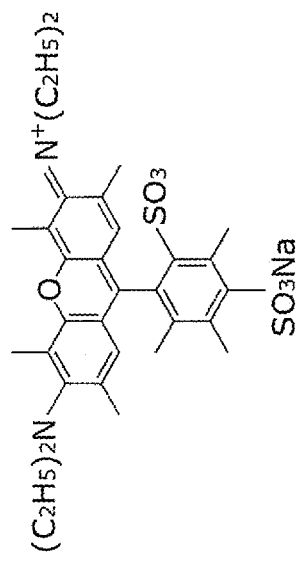
RED-#106
ACID RED

[Figure 6]
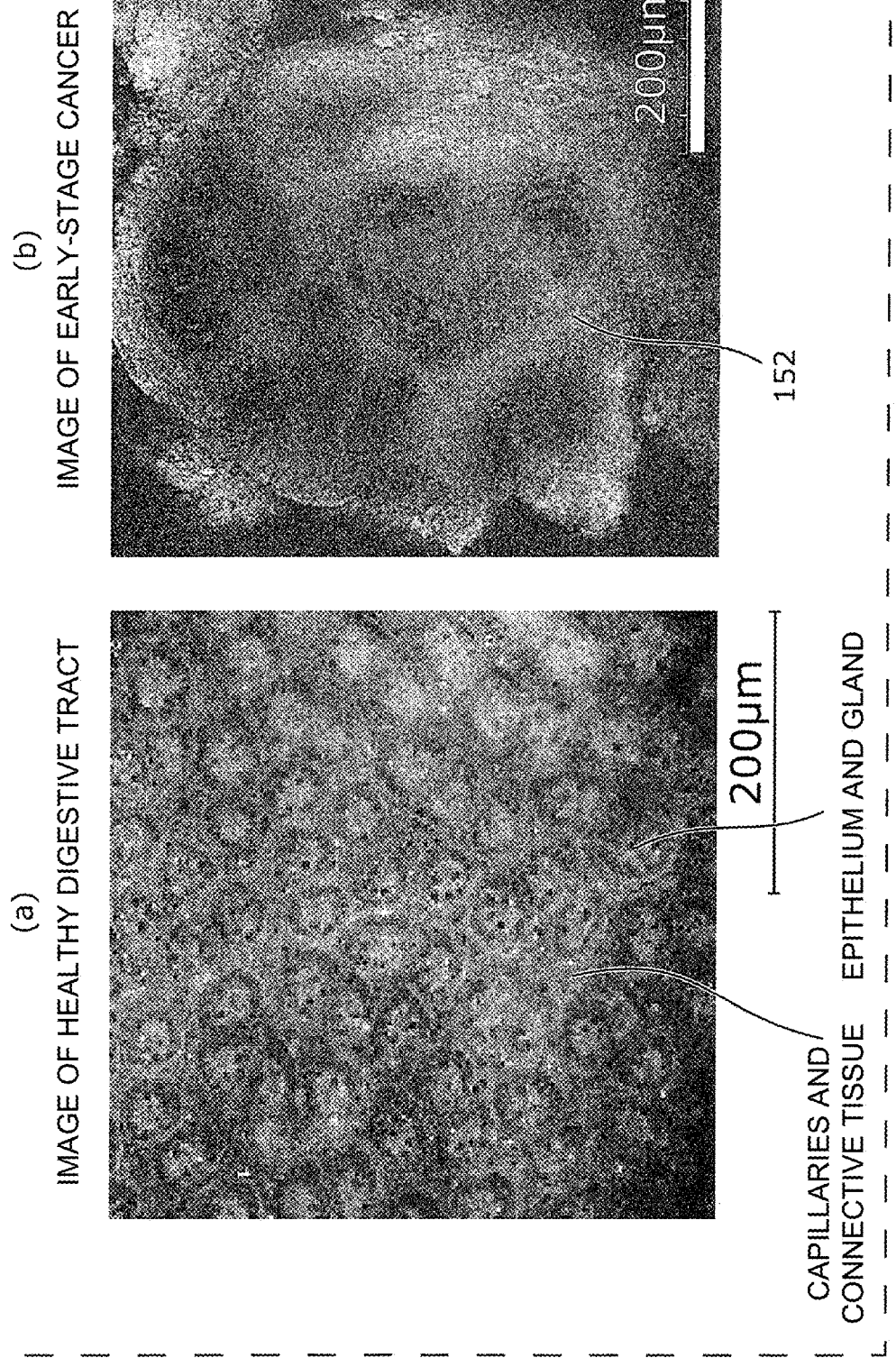

[Figure 7]
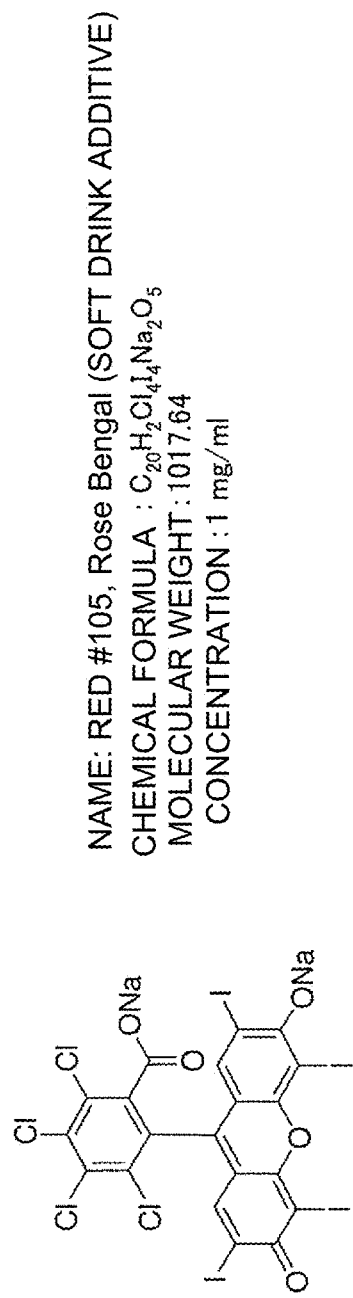
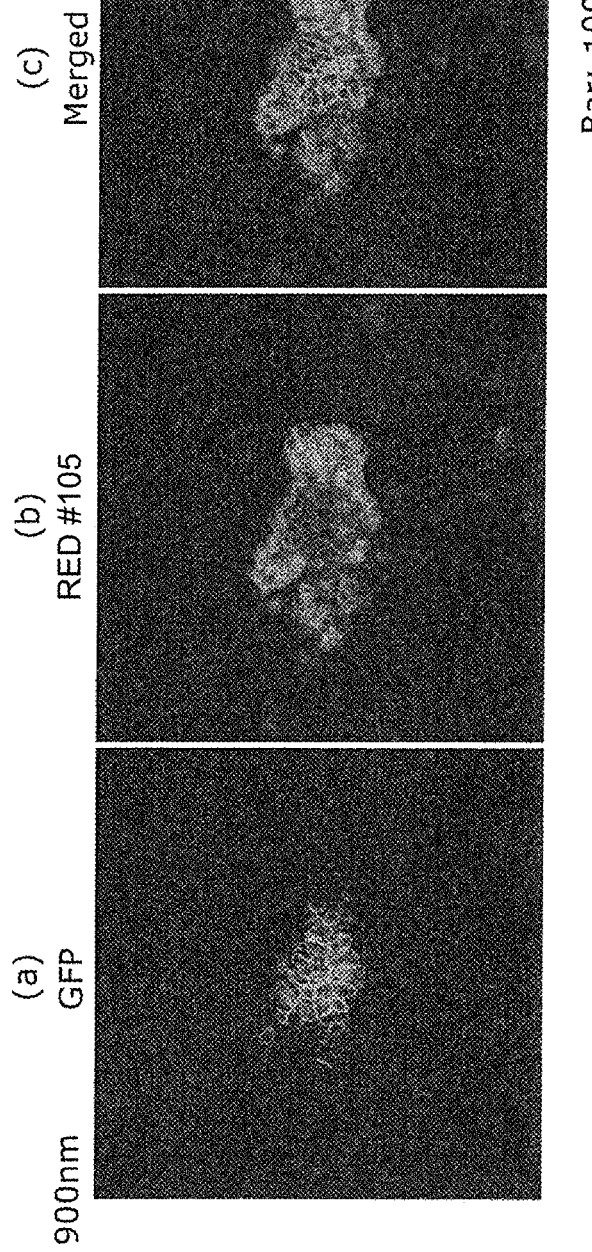
NAME: RED #105, Rose Bengal (SOFT DRINK ADDITIVE)
CHEMICAL FORMULA: $C_{20}H_2Cl_4I_4Na_2O_5$
MOLECULAR WEIGHT: 1017.64
CONCENTRATION: 1 mg/ml
900nm  (a) GFP   (b) RED #105   (c) Merged
Bar: 100 μm

[Figure 8]
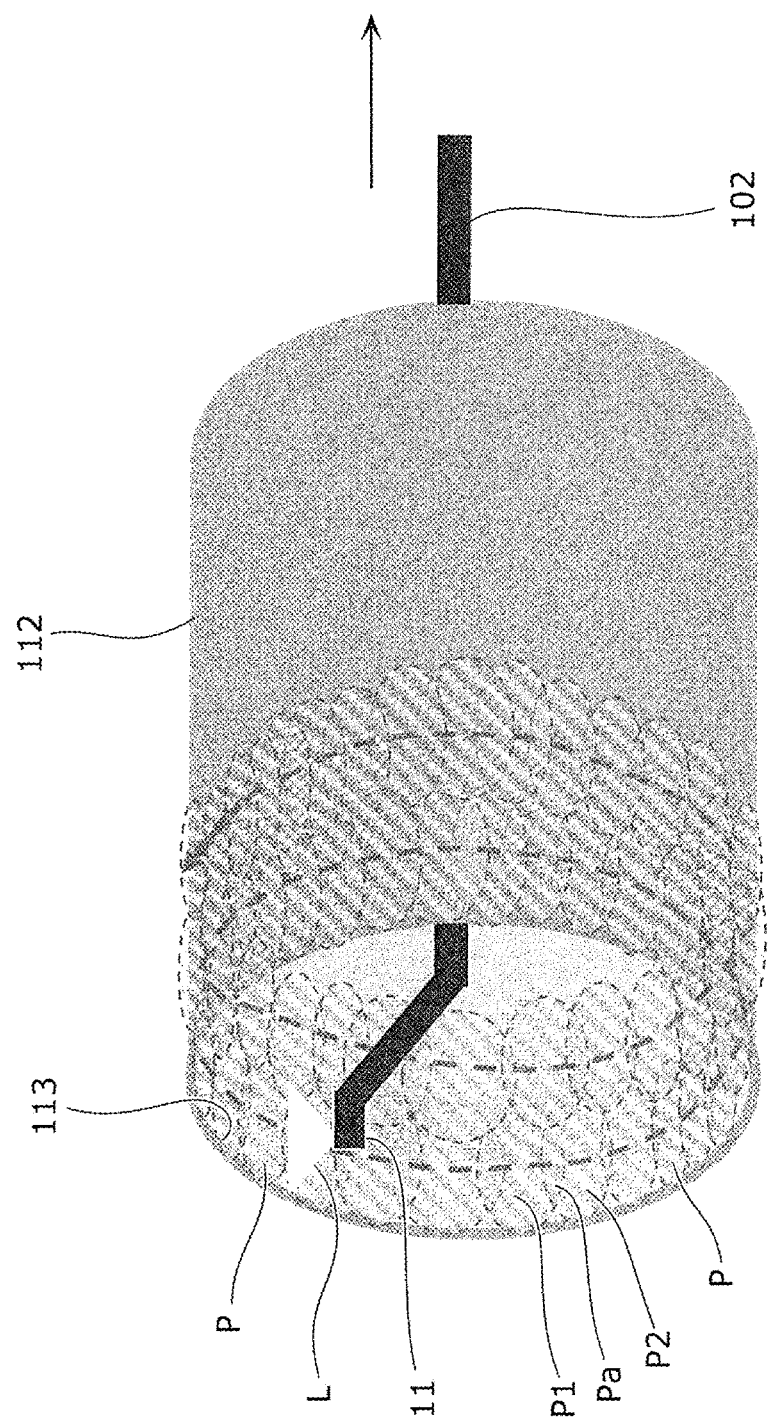

[Figure 9]
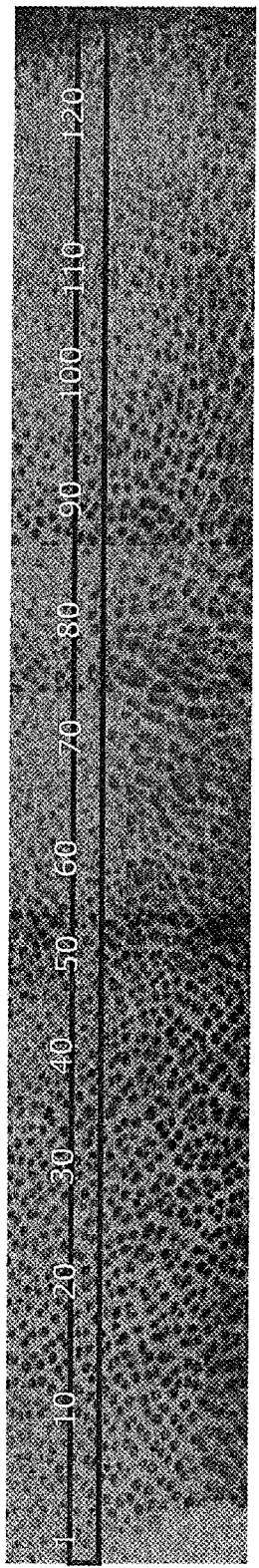

[Figure 10A]
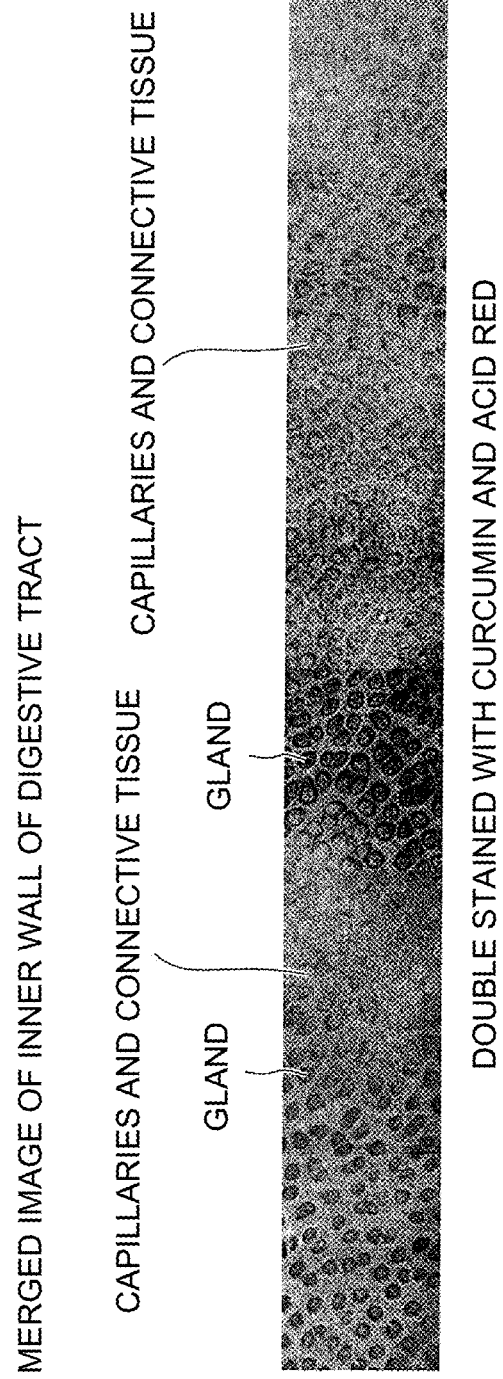

[Figure 10B]
STEREOSCOPIC IMAGE RECONSTRUCTED
FROM PANORAMIC IMAGE
(INNER WALL OF DIGESTIVE TRACT)
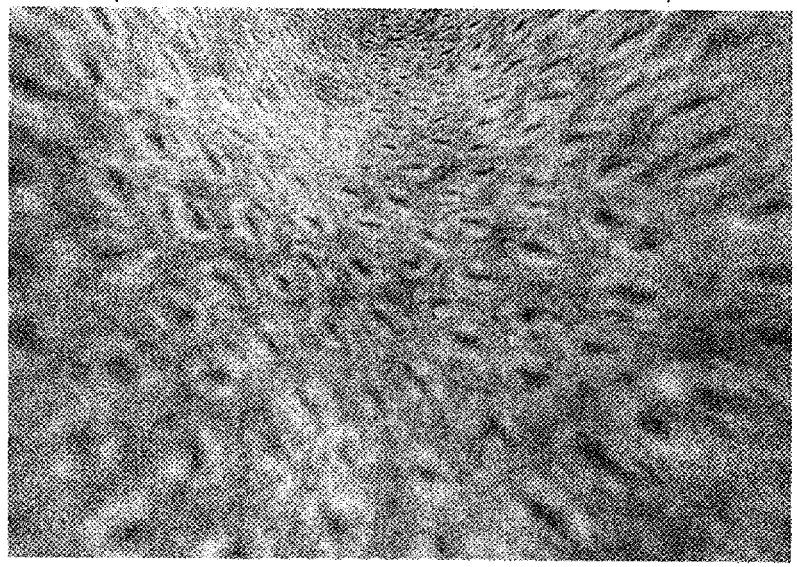

[Figure 11]
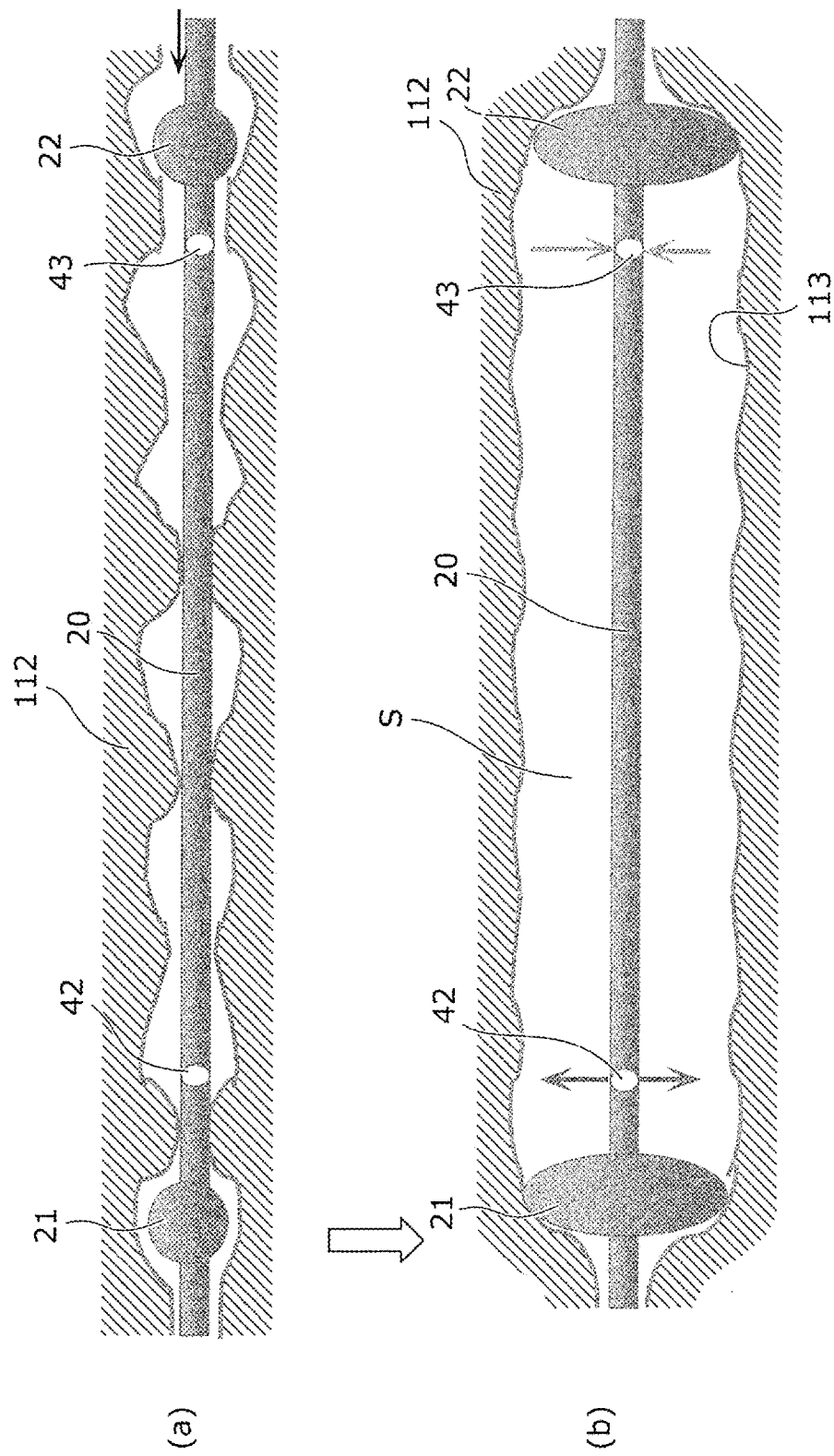

[Figure 12]
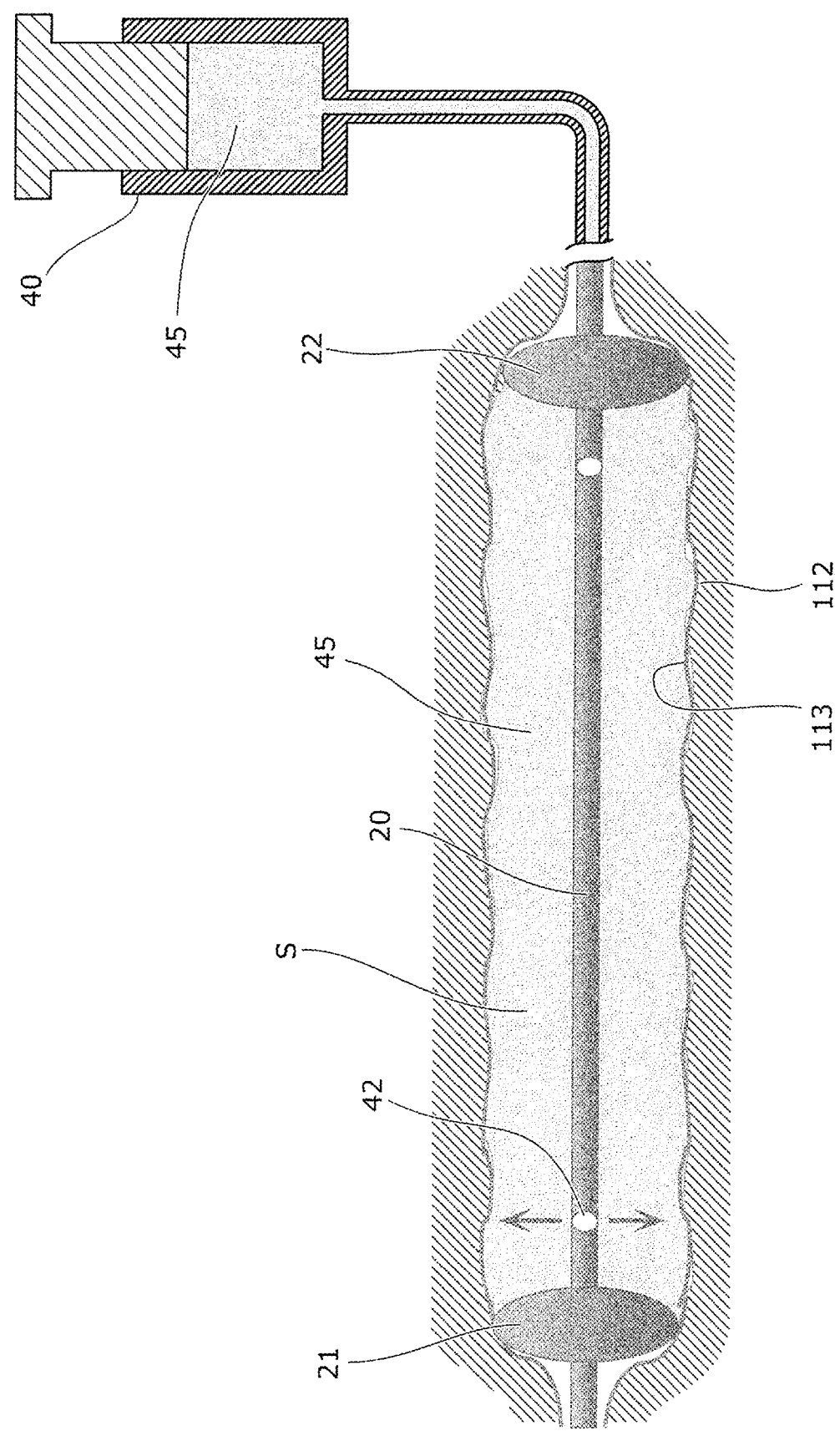

[Figure 13]
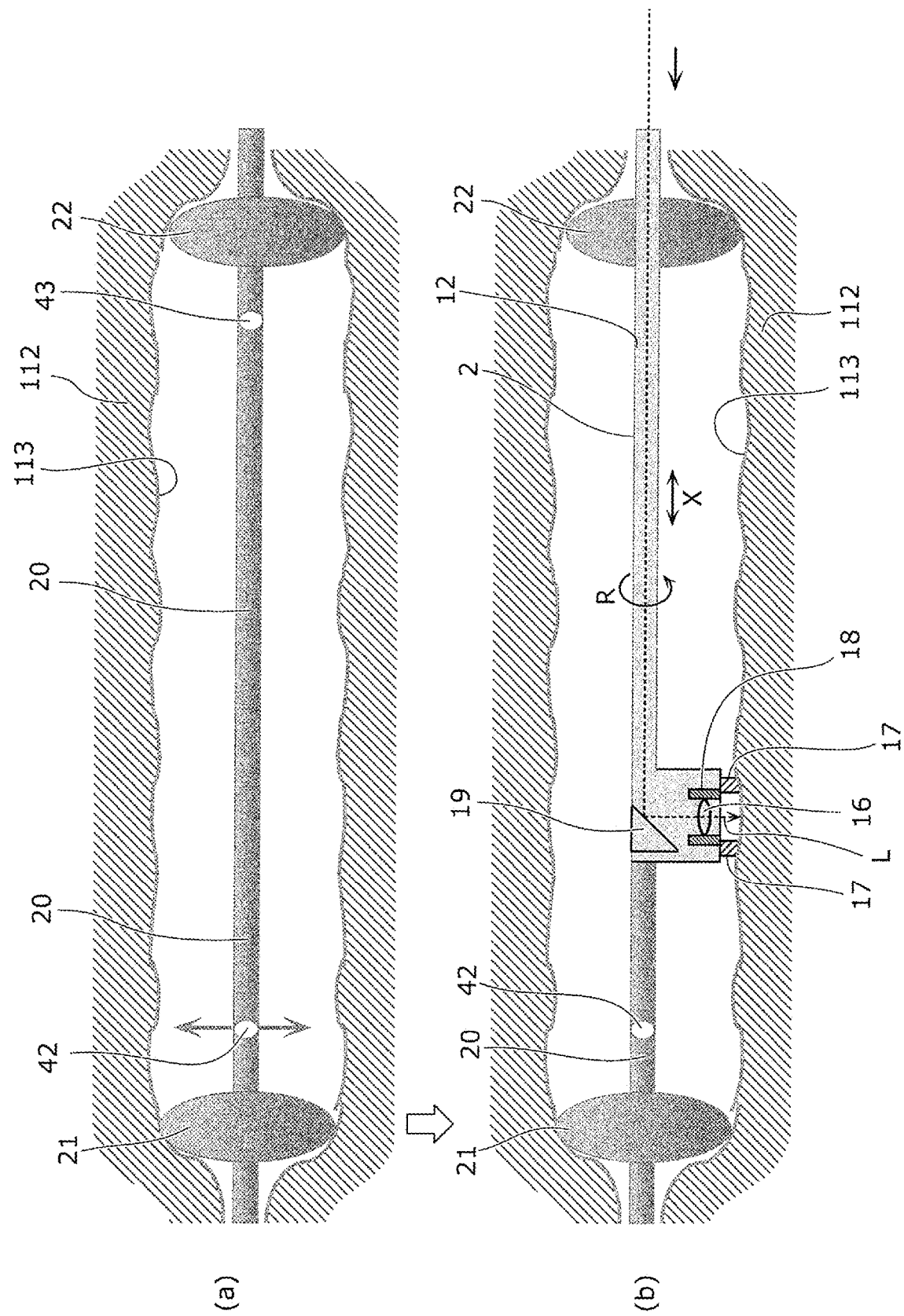

[Figure 14]
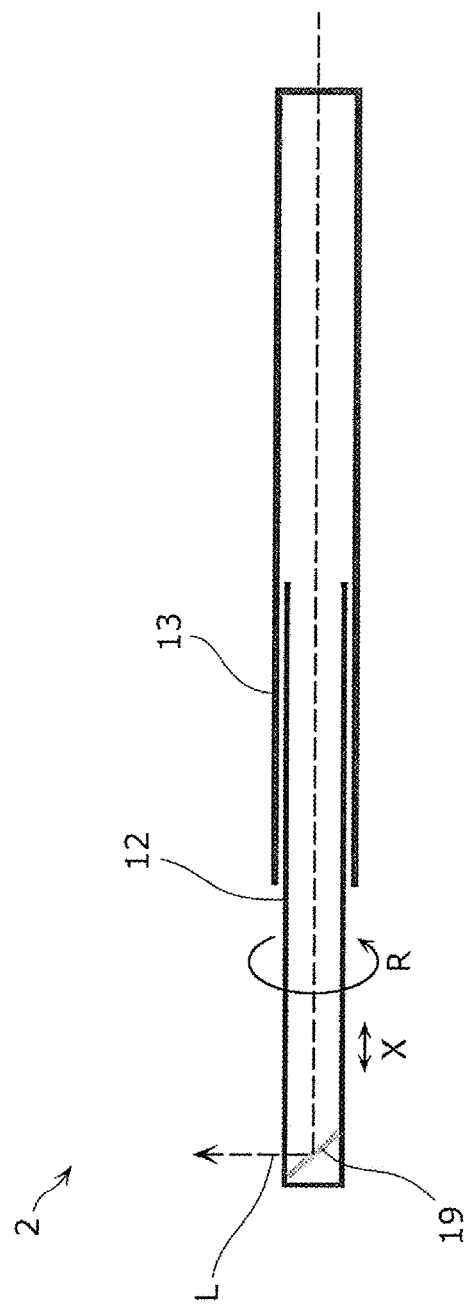

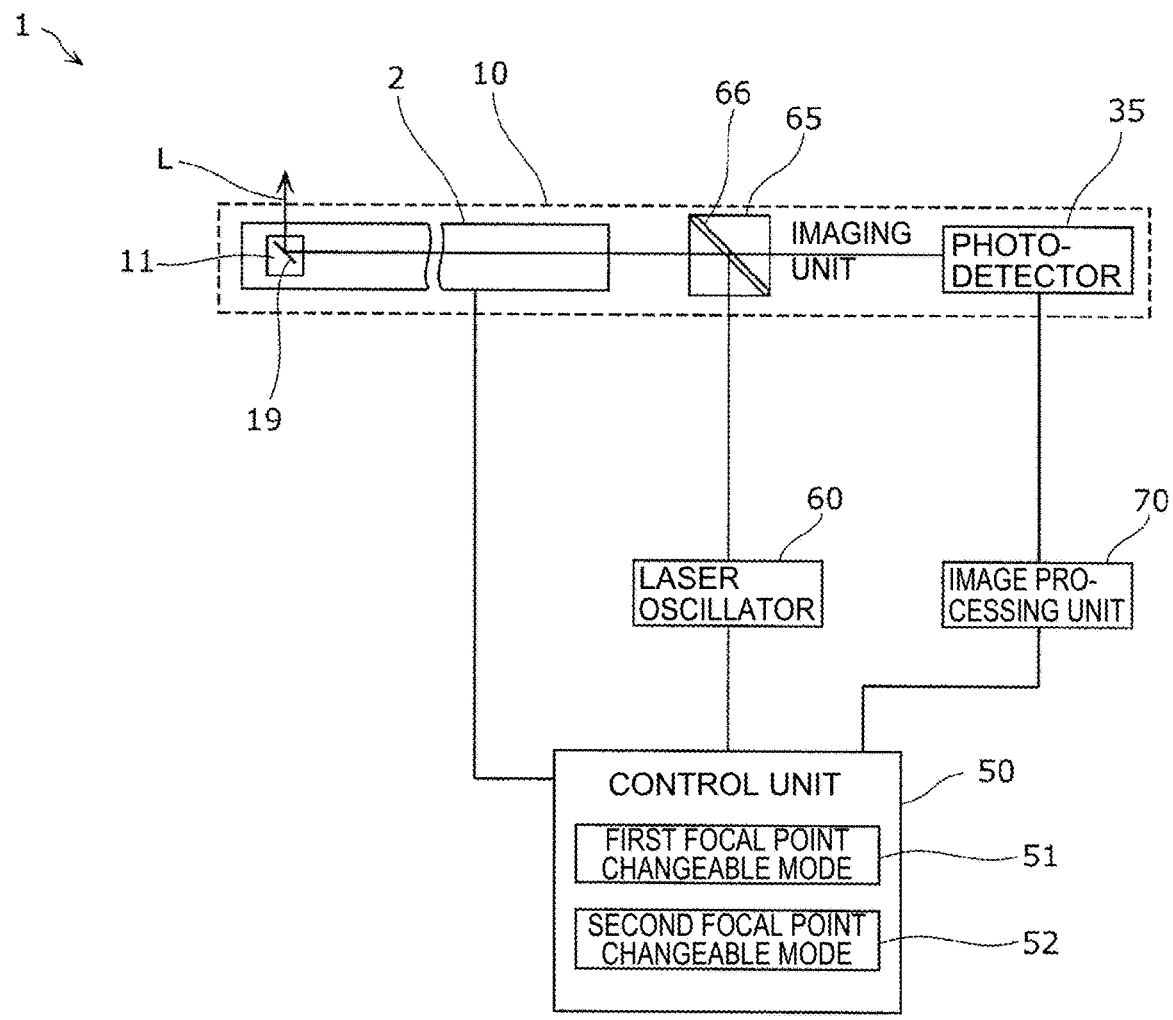
[Figure 15]

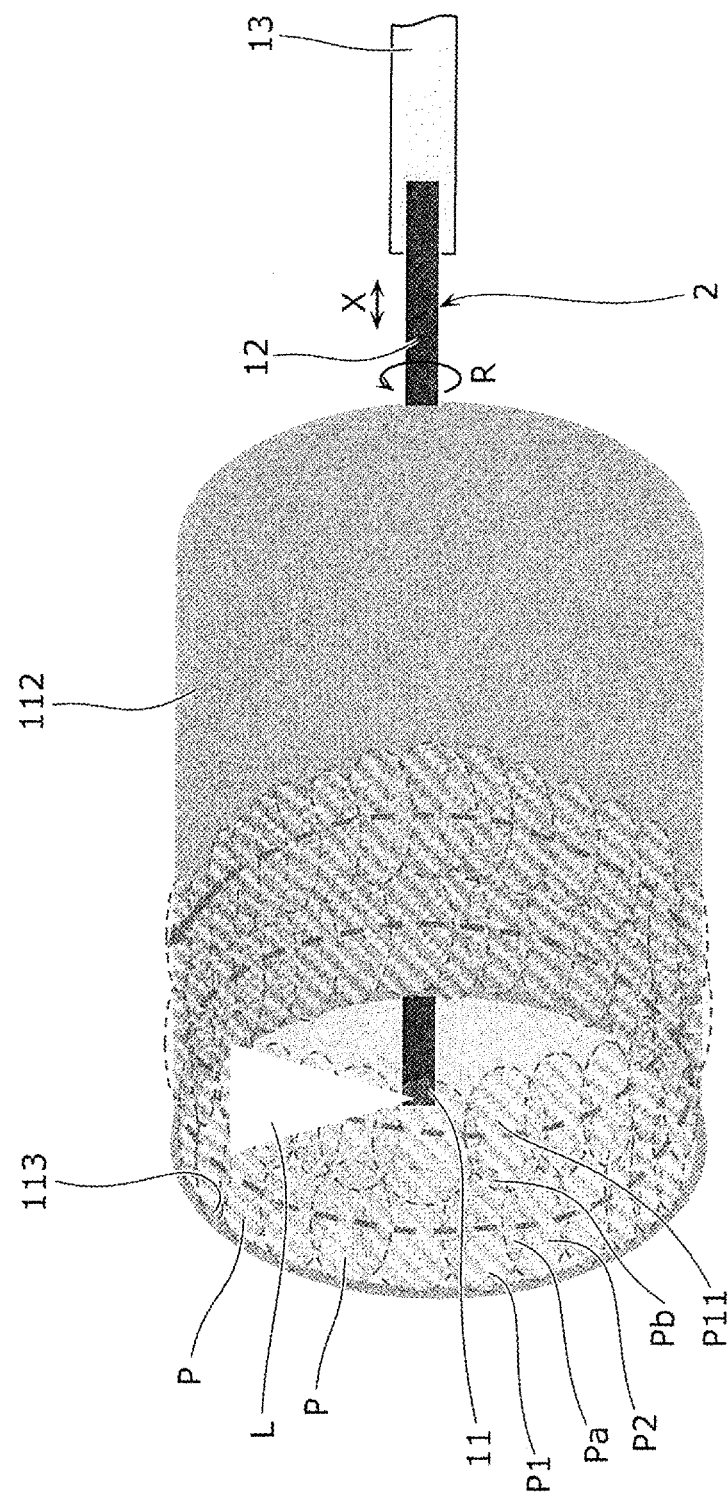
[Figure 16]

[Figure 17A]
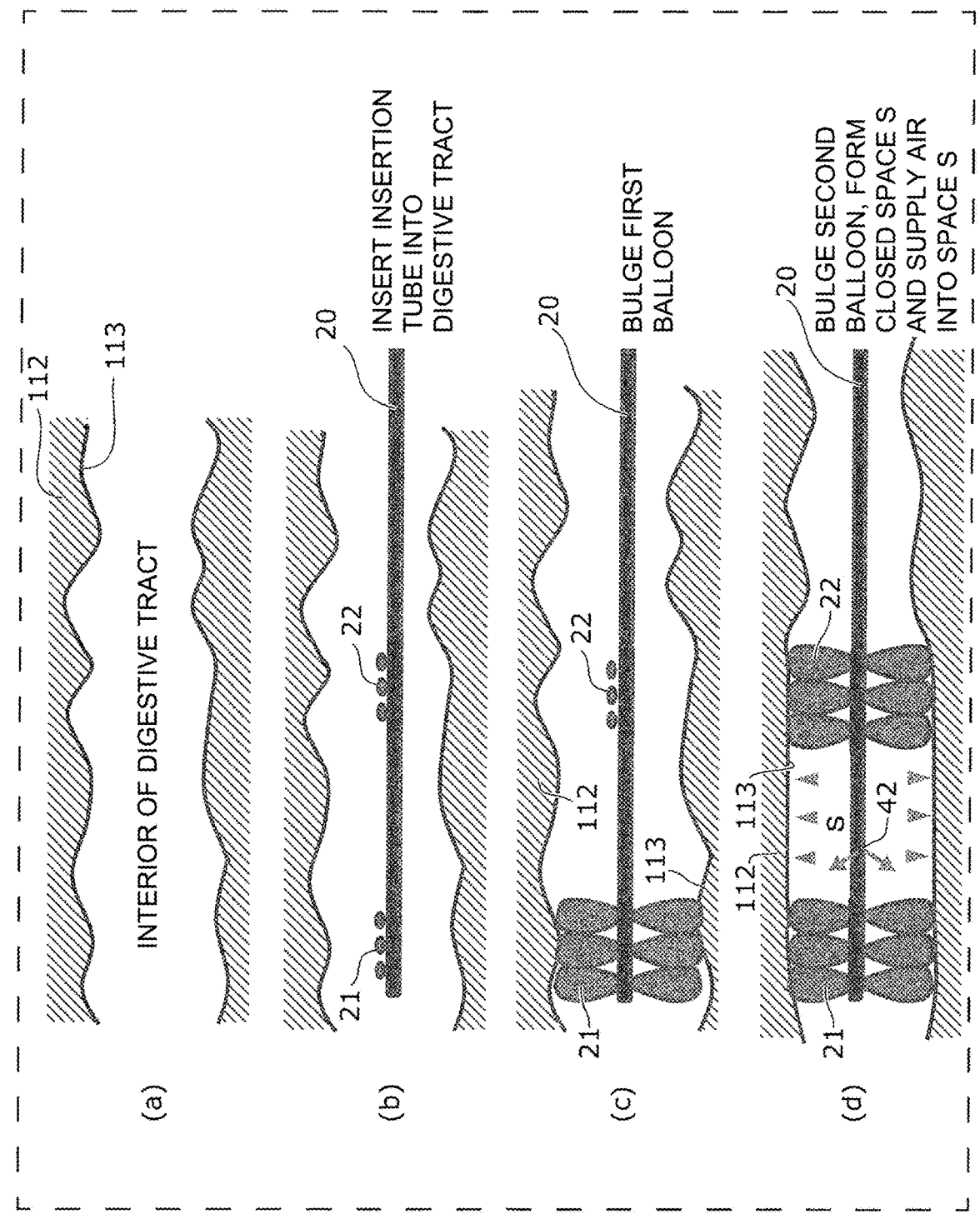

[Figure 17B]
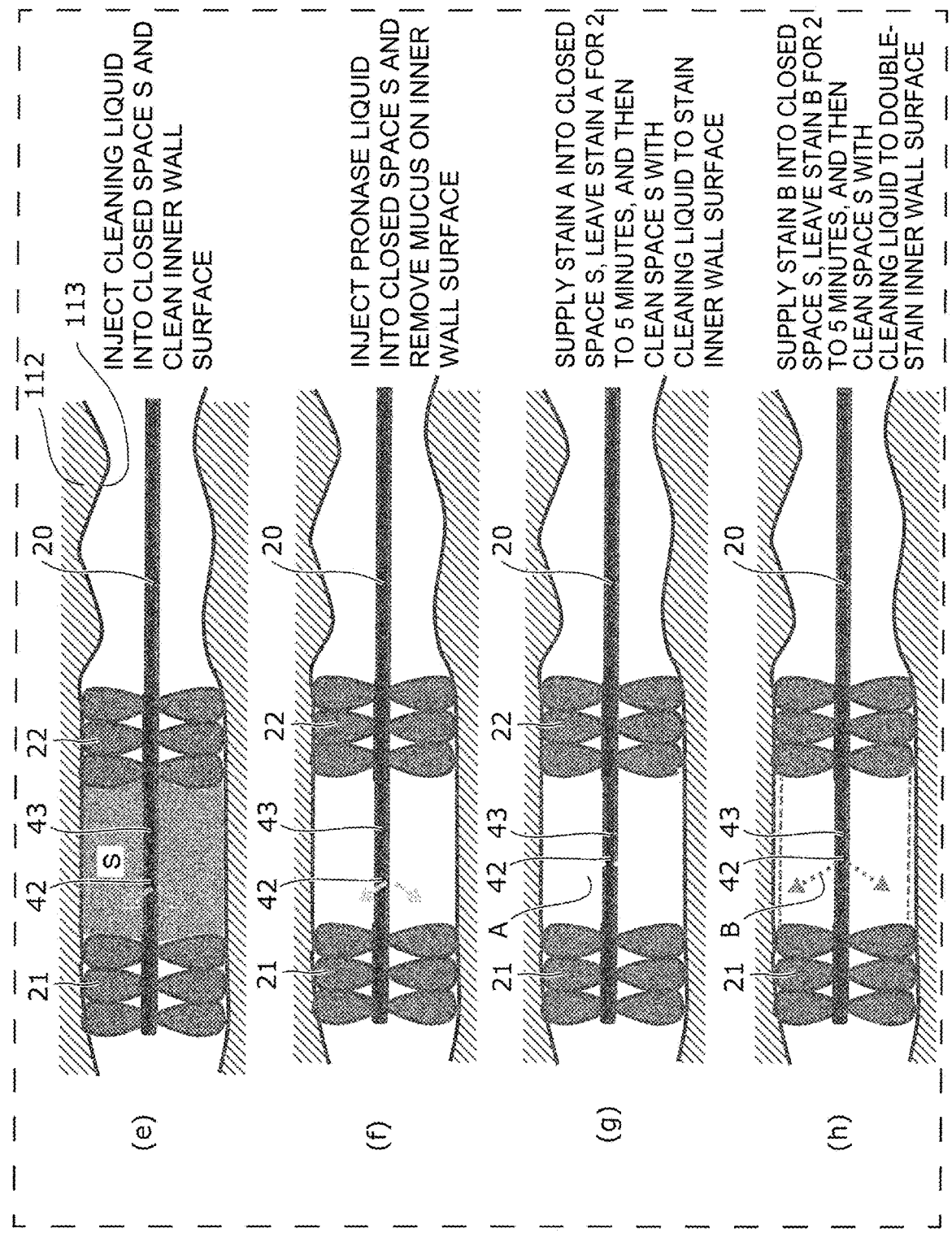

[Figure 17C]
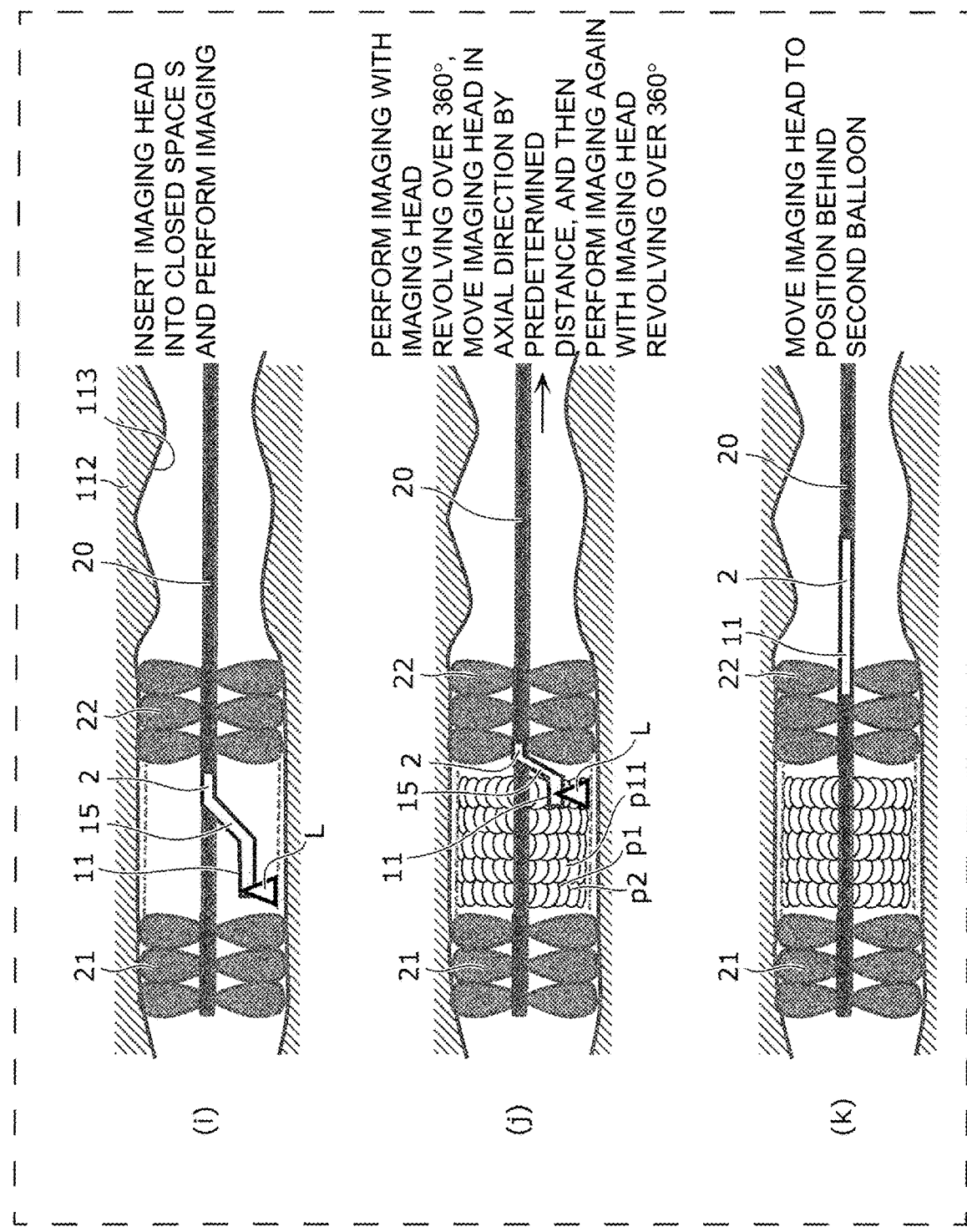

[Figure 17D]
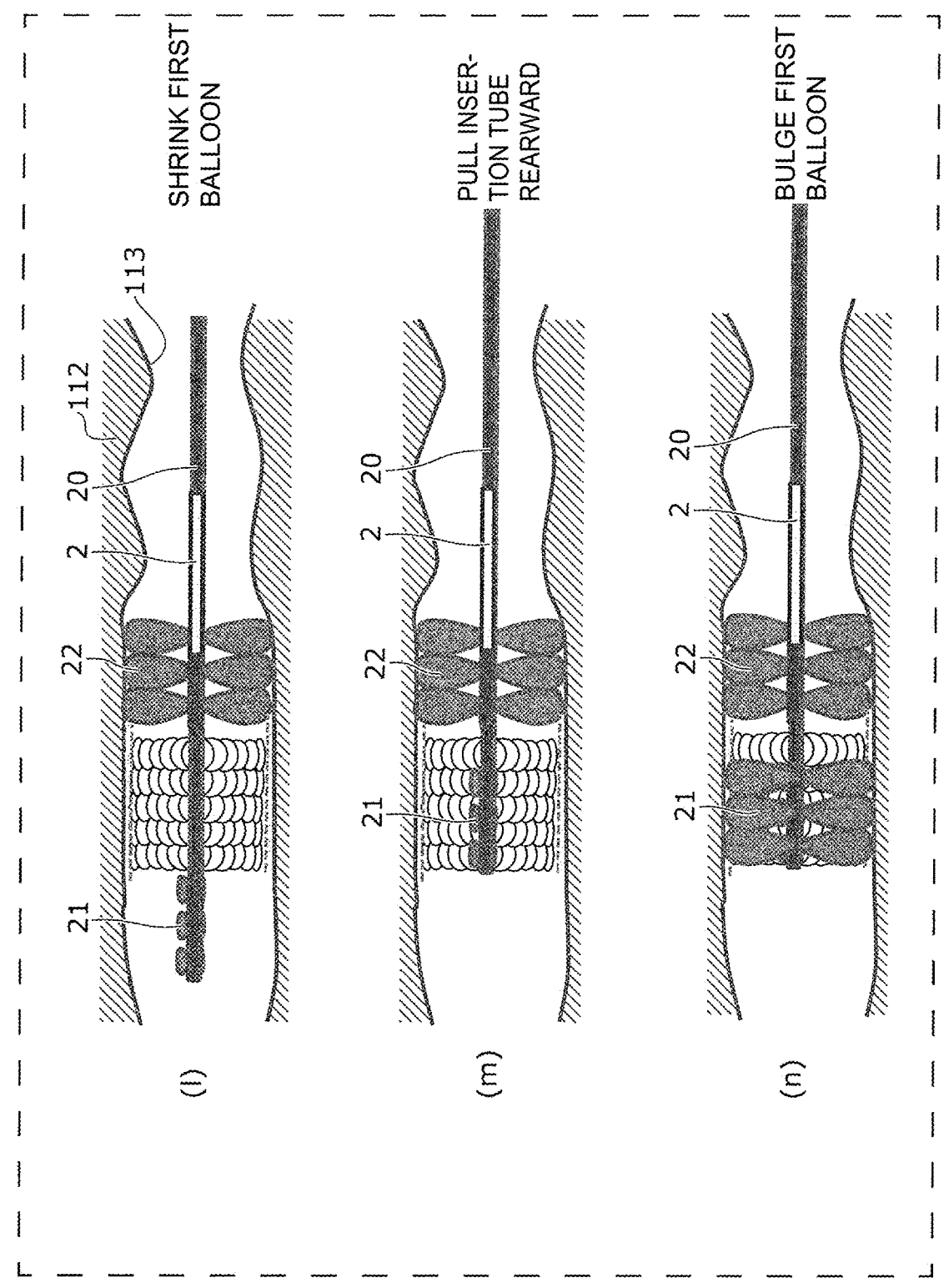

[Figure 17E]
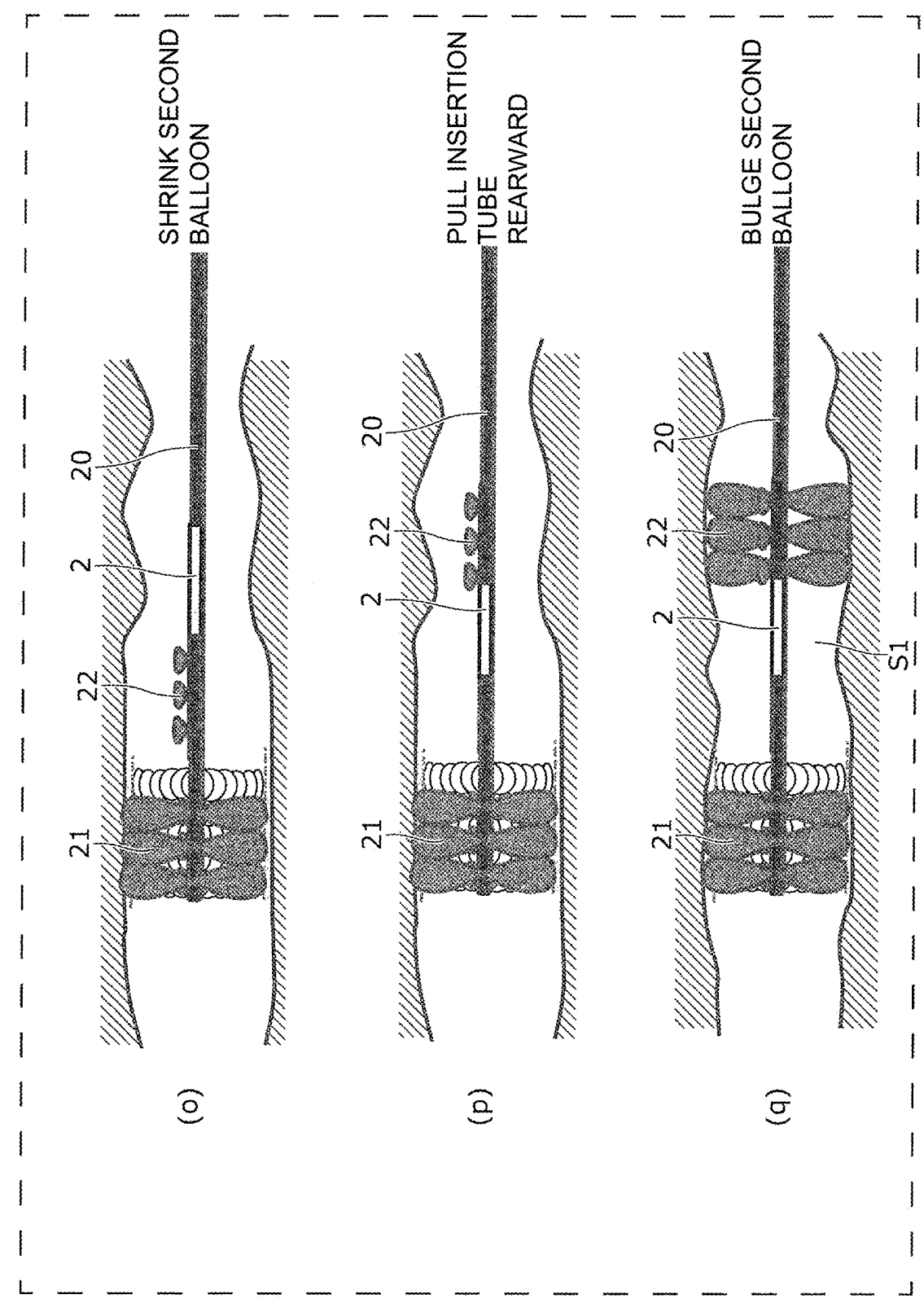

[Figure 18]
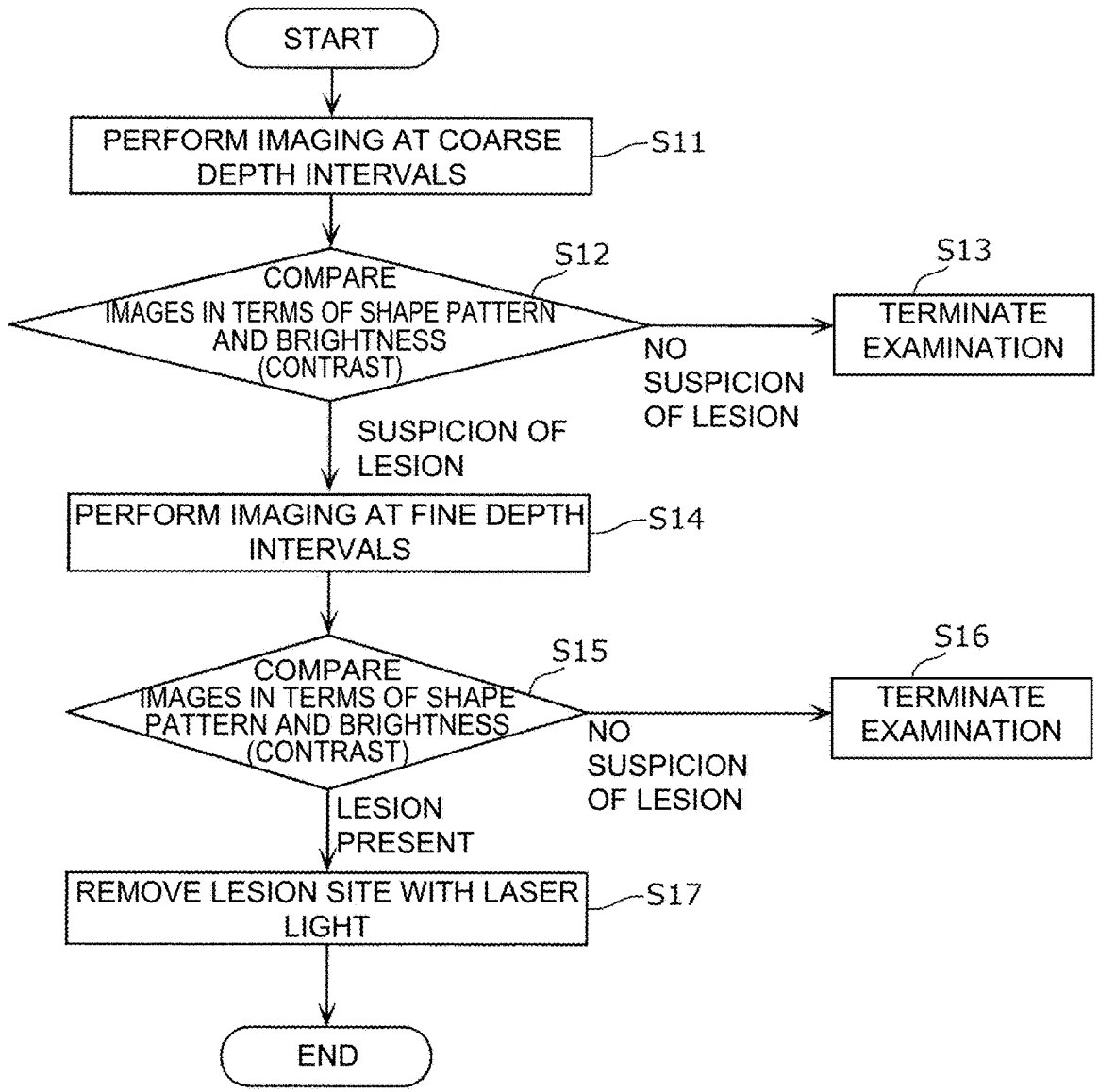

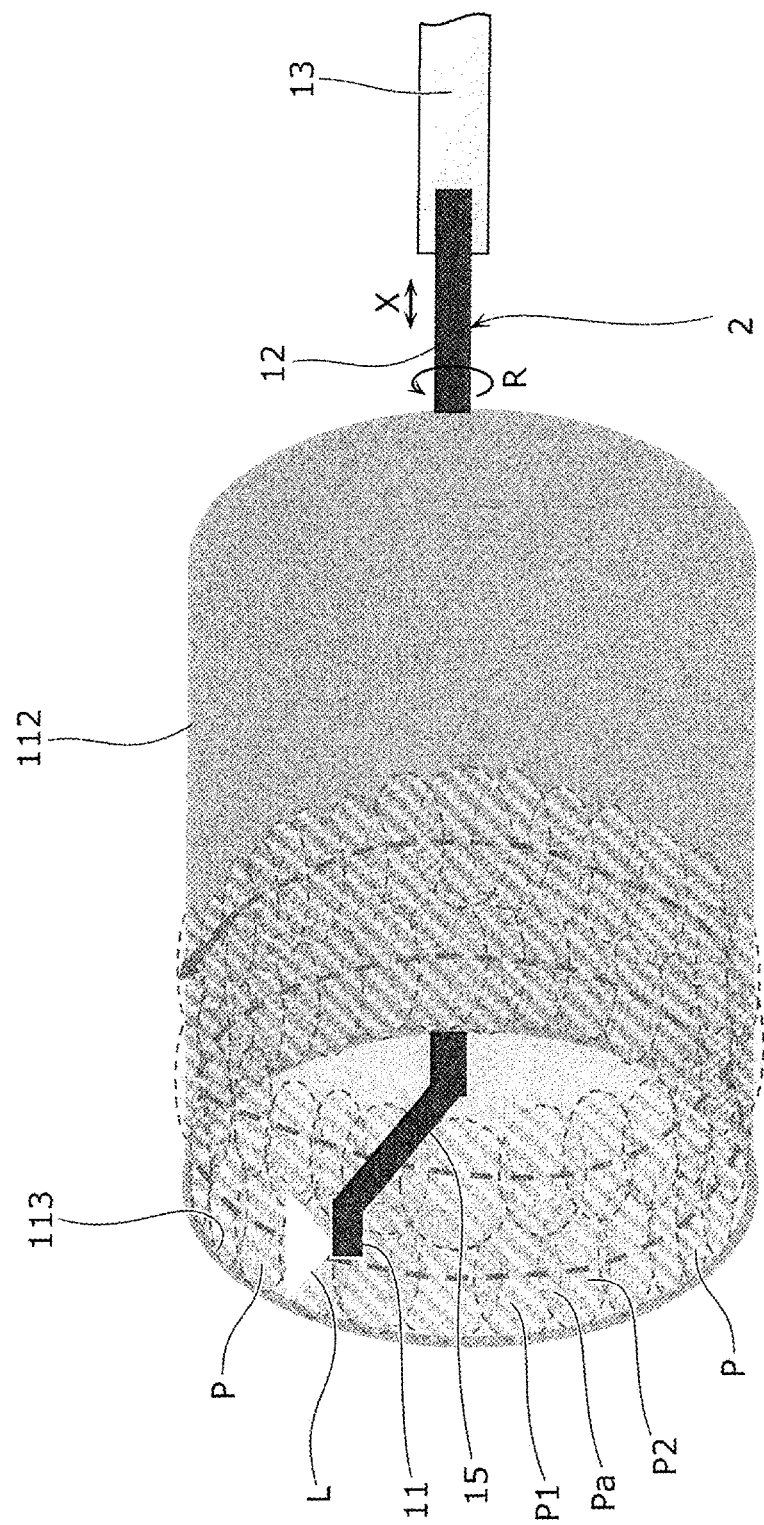
[Figure 19]

[Figure 20]
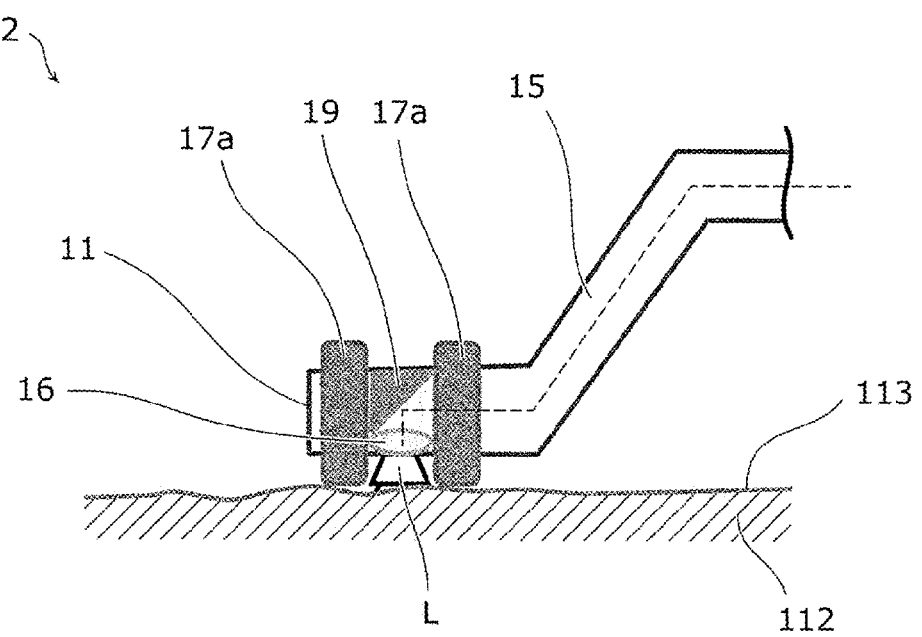

[Figure 21]
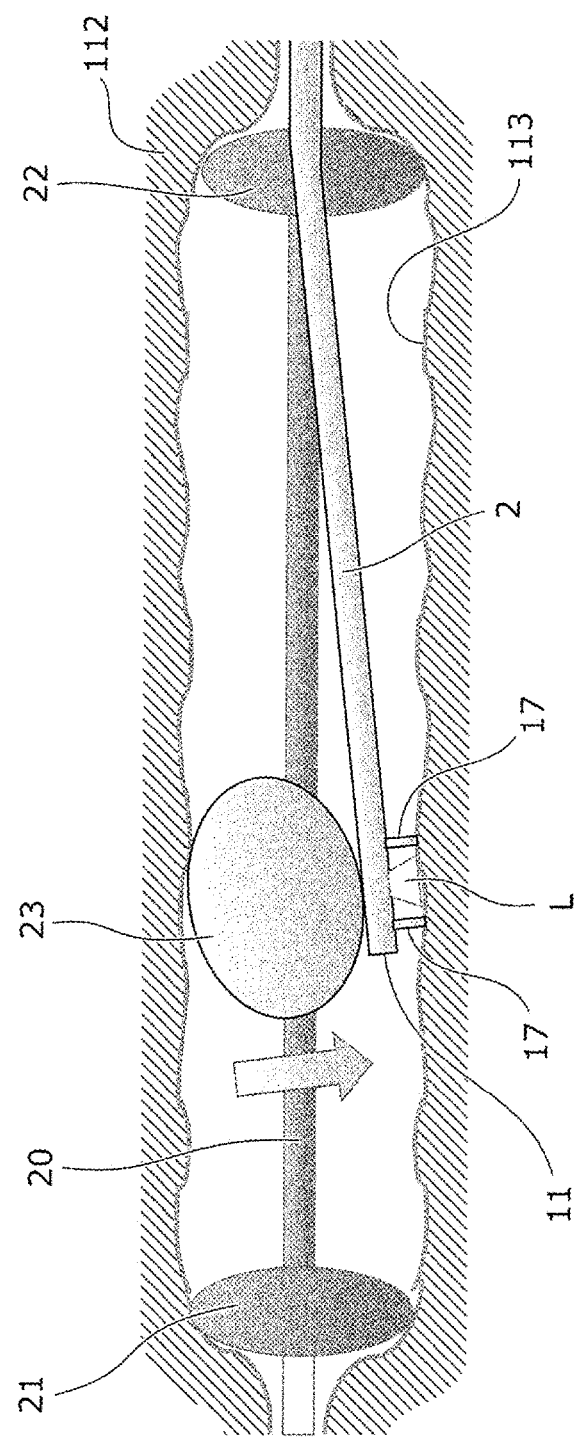

[Figure 22]
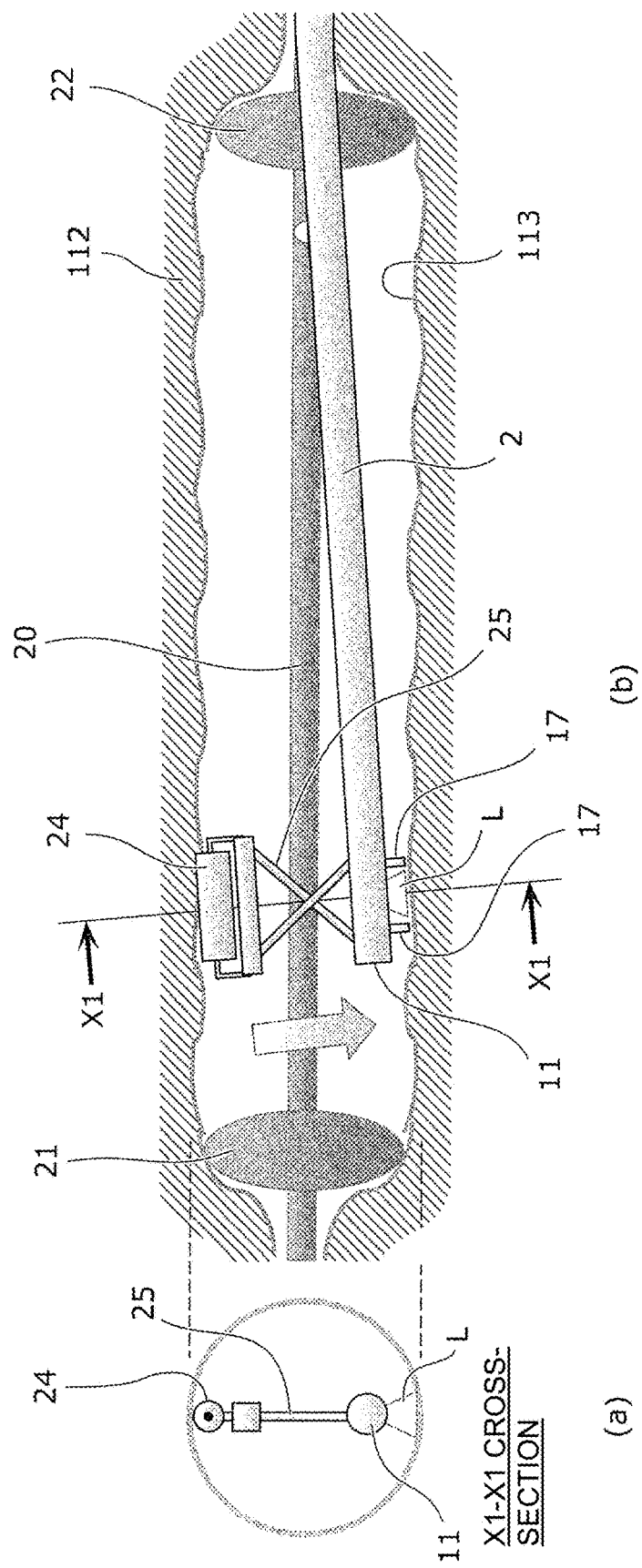

[Figure 23]
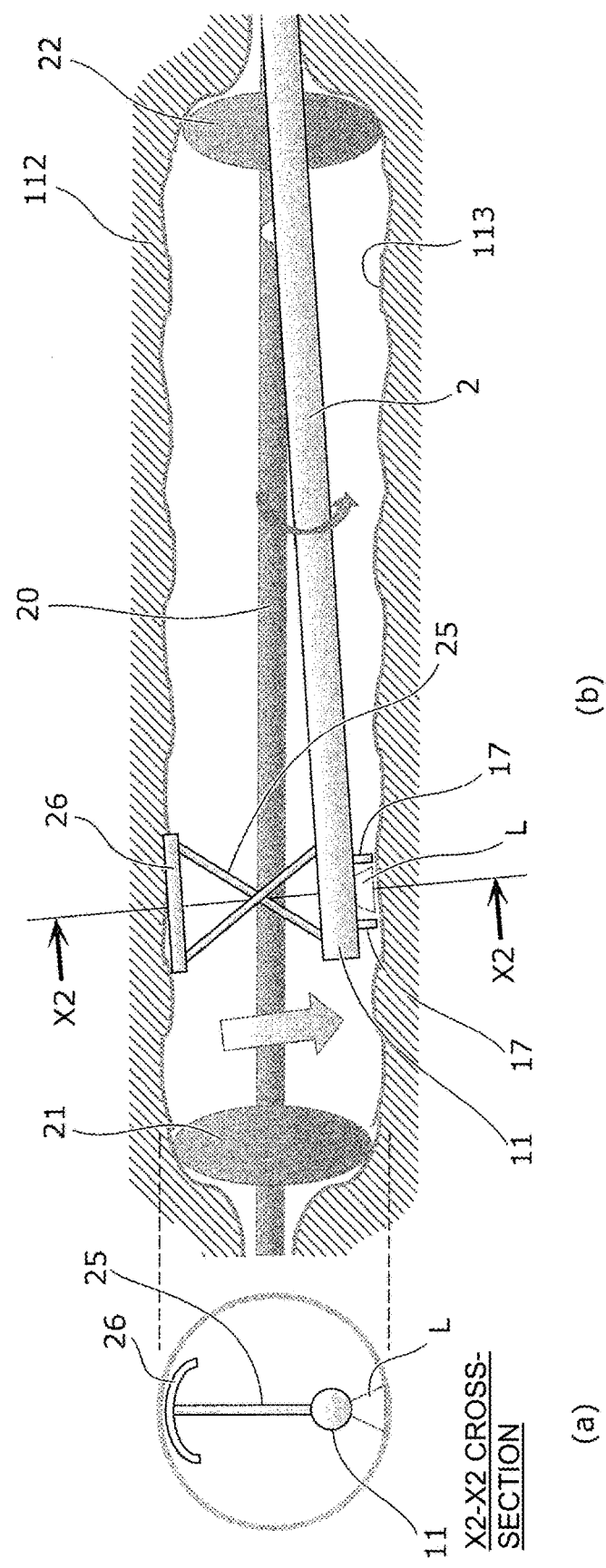

[Figure 24]
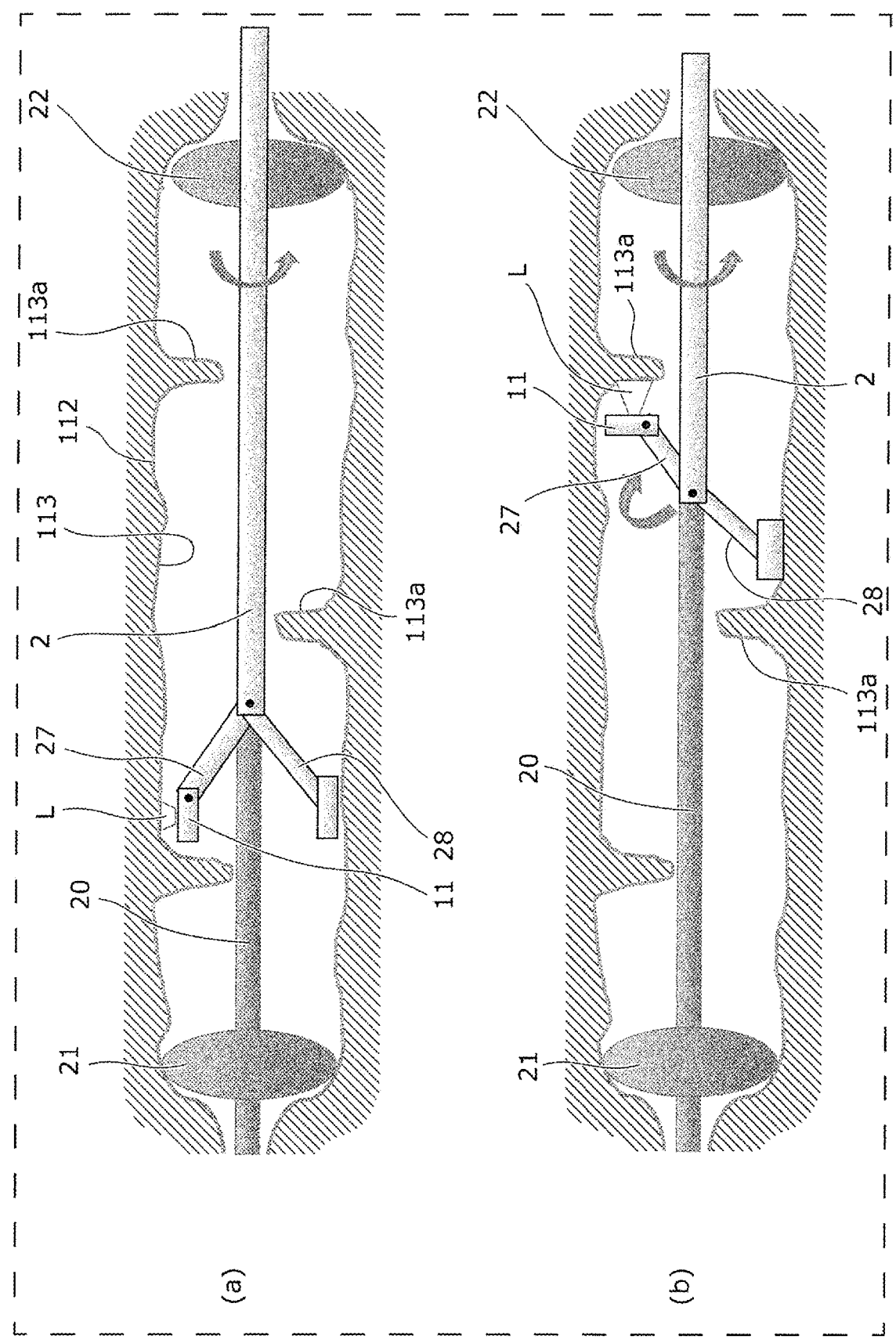

[Figure 25]
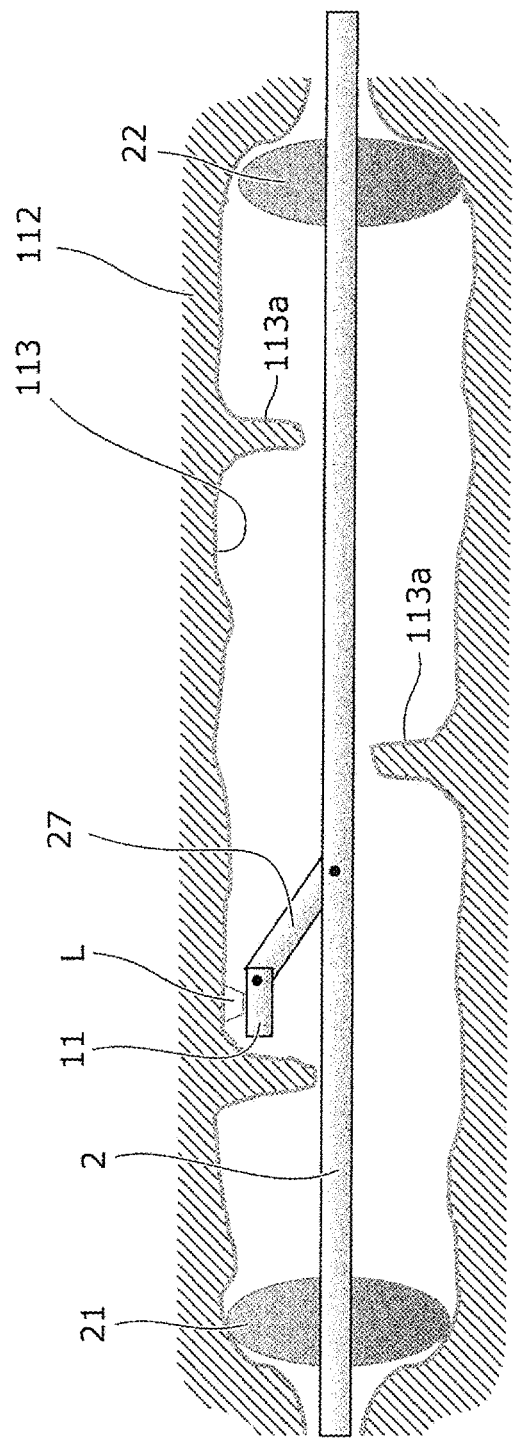

[Figure 26]
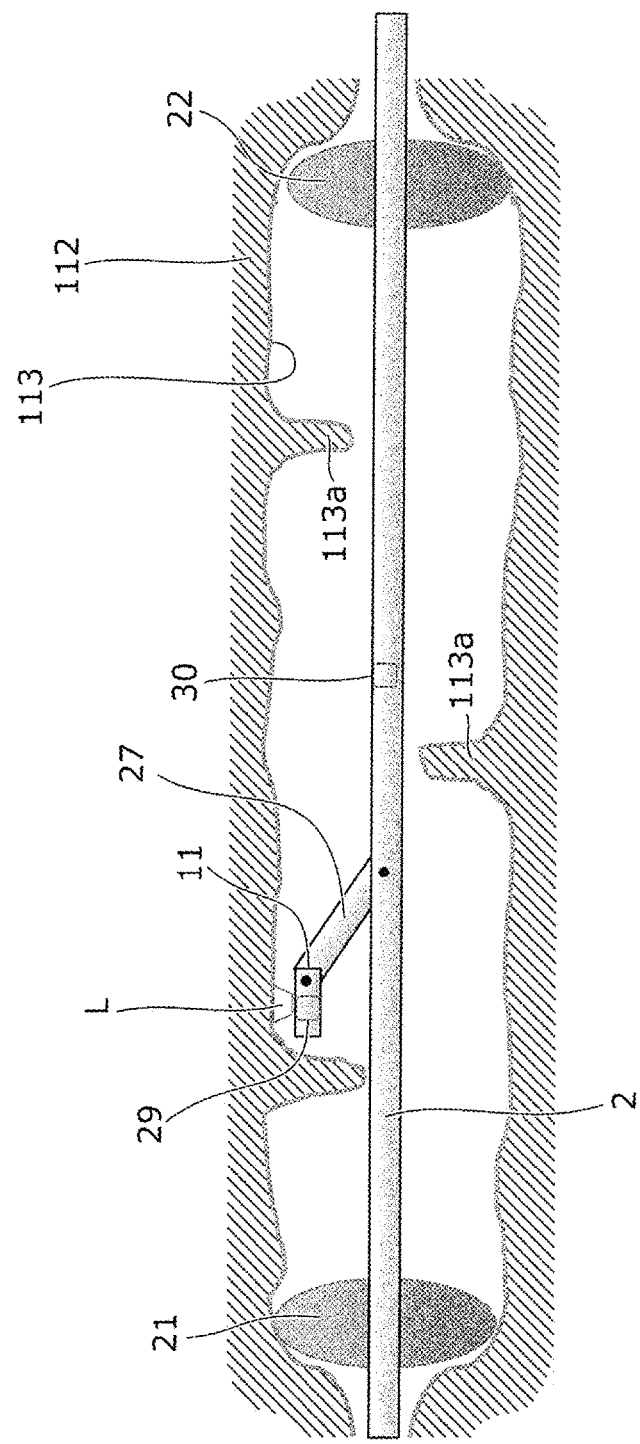

[Figure 27]
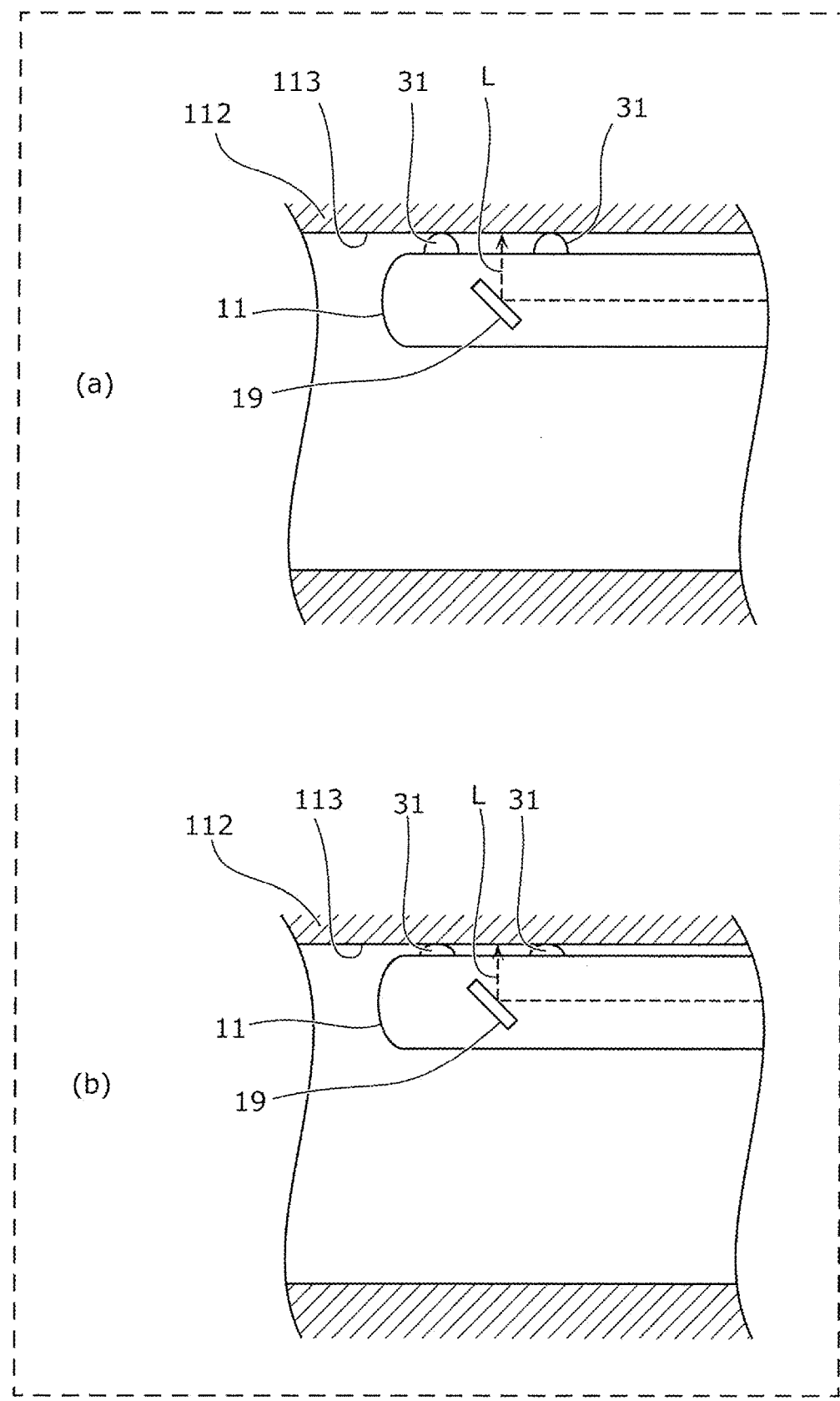

[Figure 28]
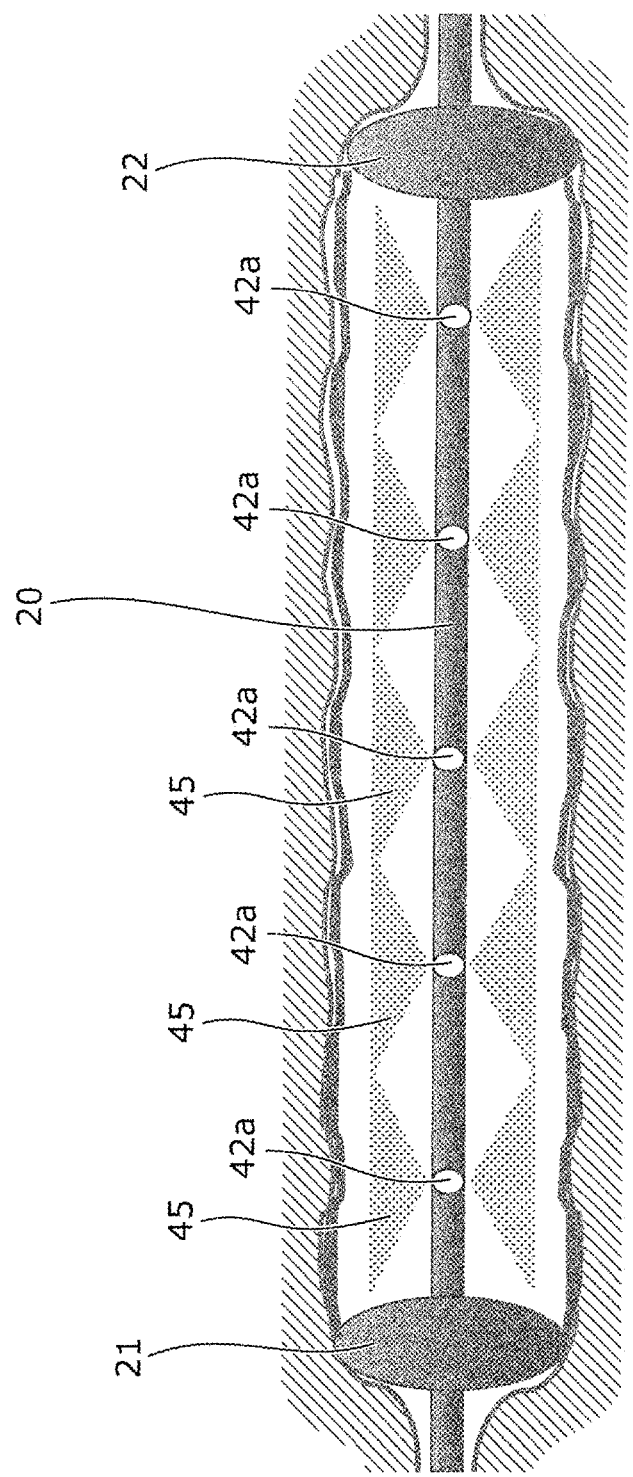

[Figure 29]
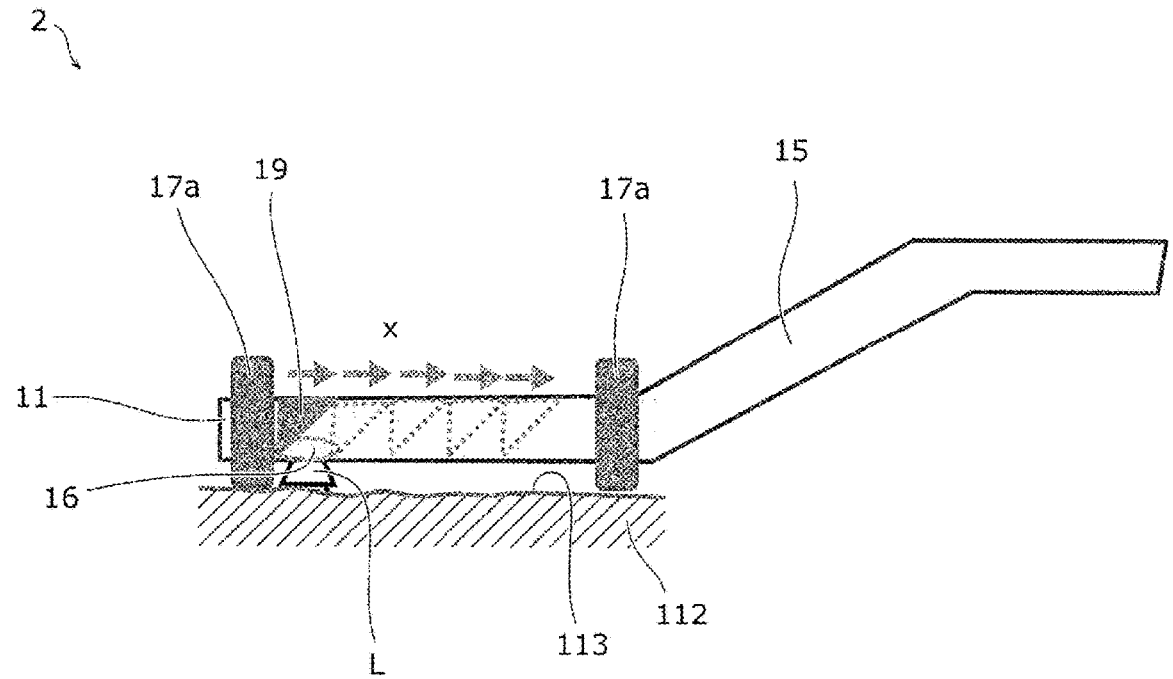
[Figure 30]
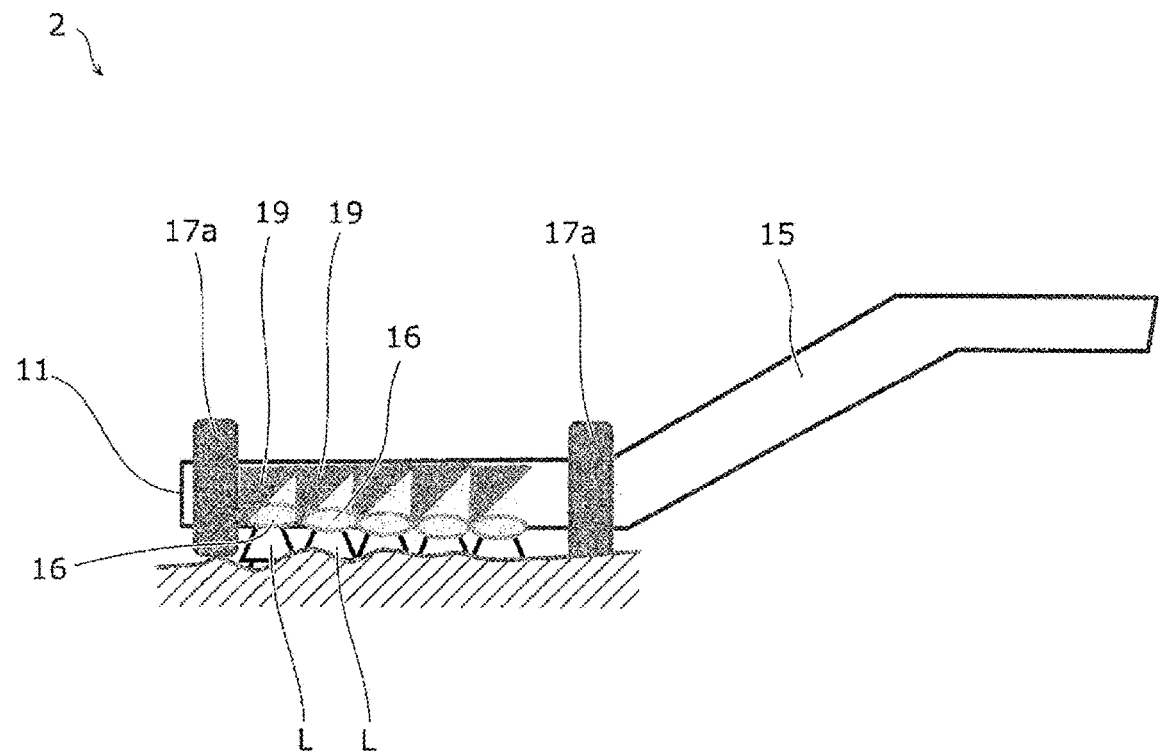

[Figure 31]
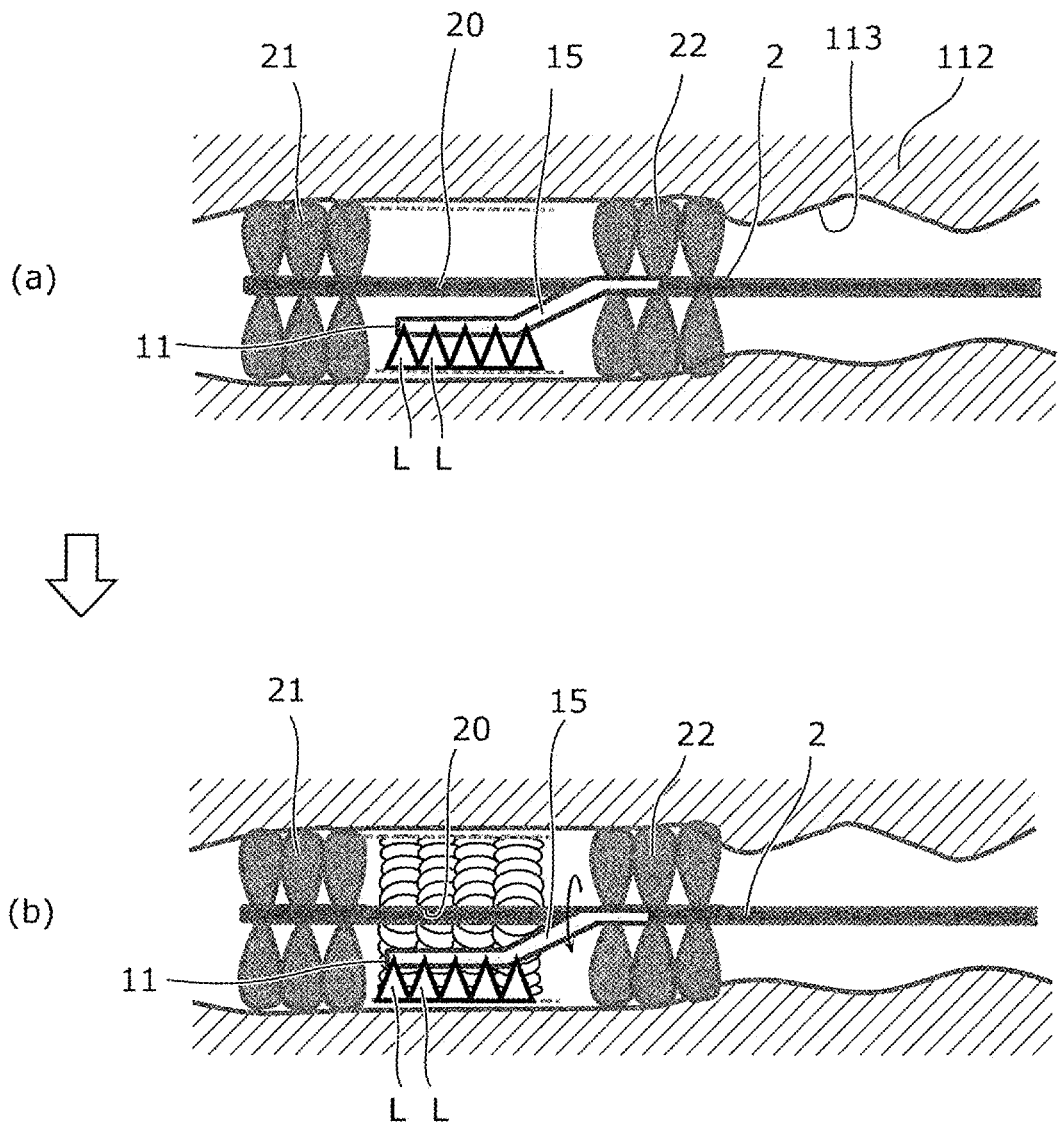

[Figure 32A]
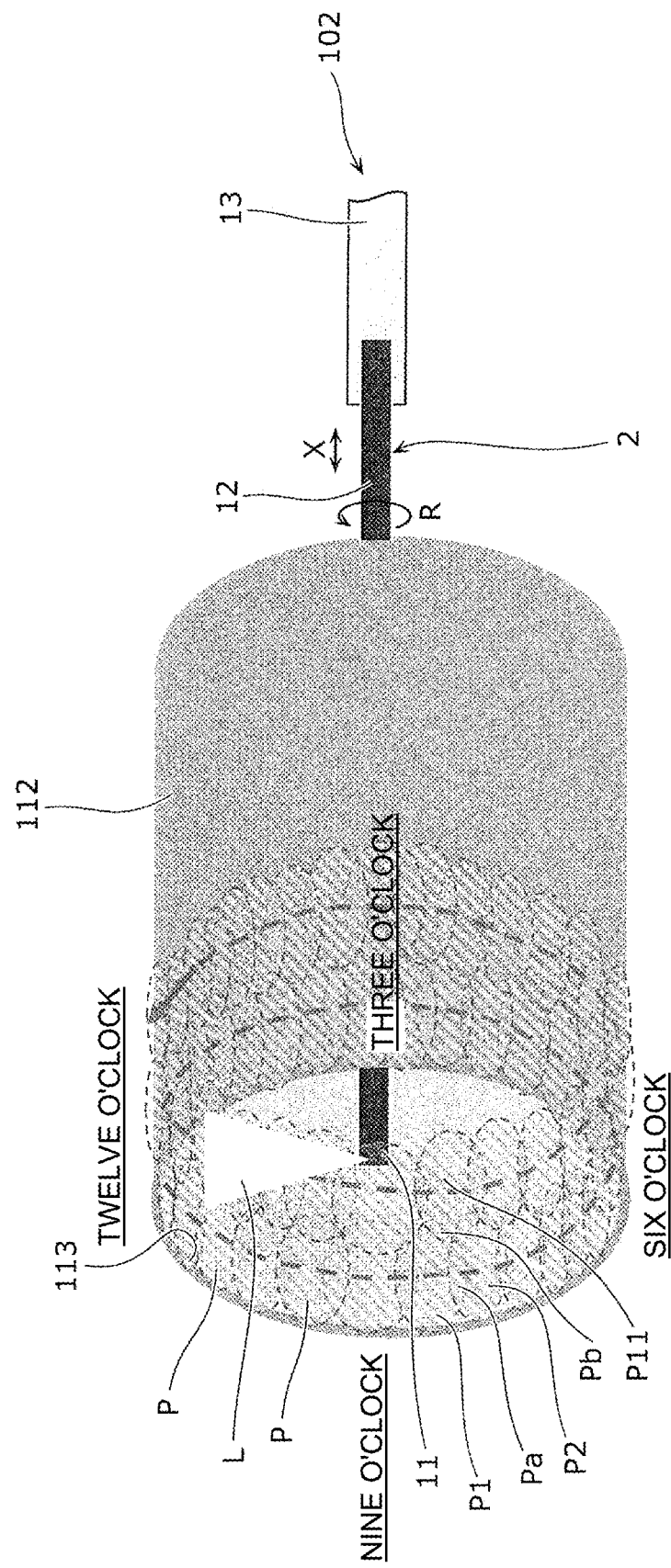

[Figure 32B]
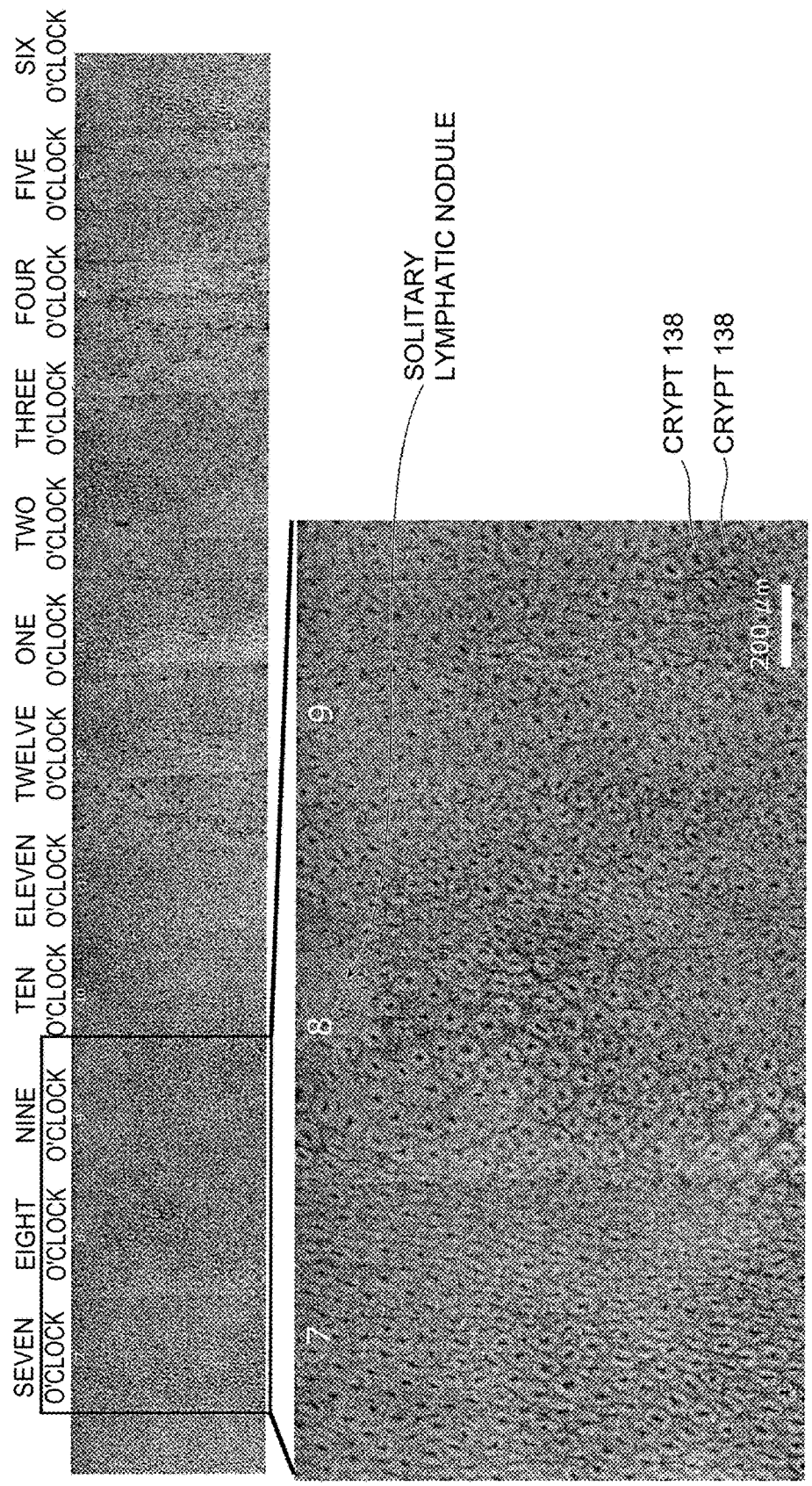

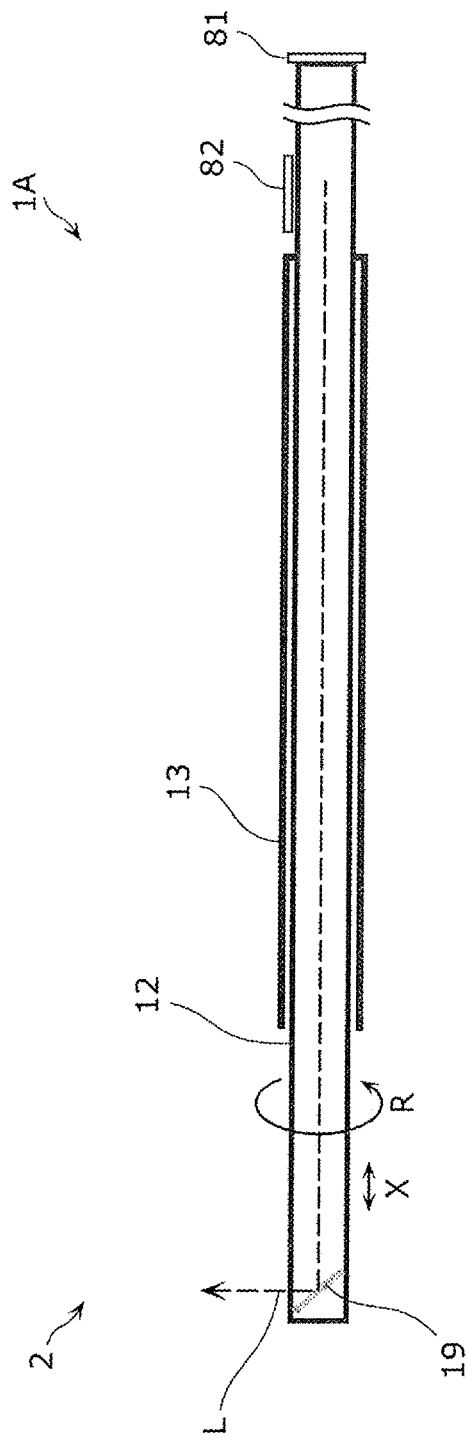
[Figure 33]

[Figure 34A]
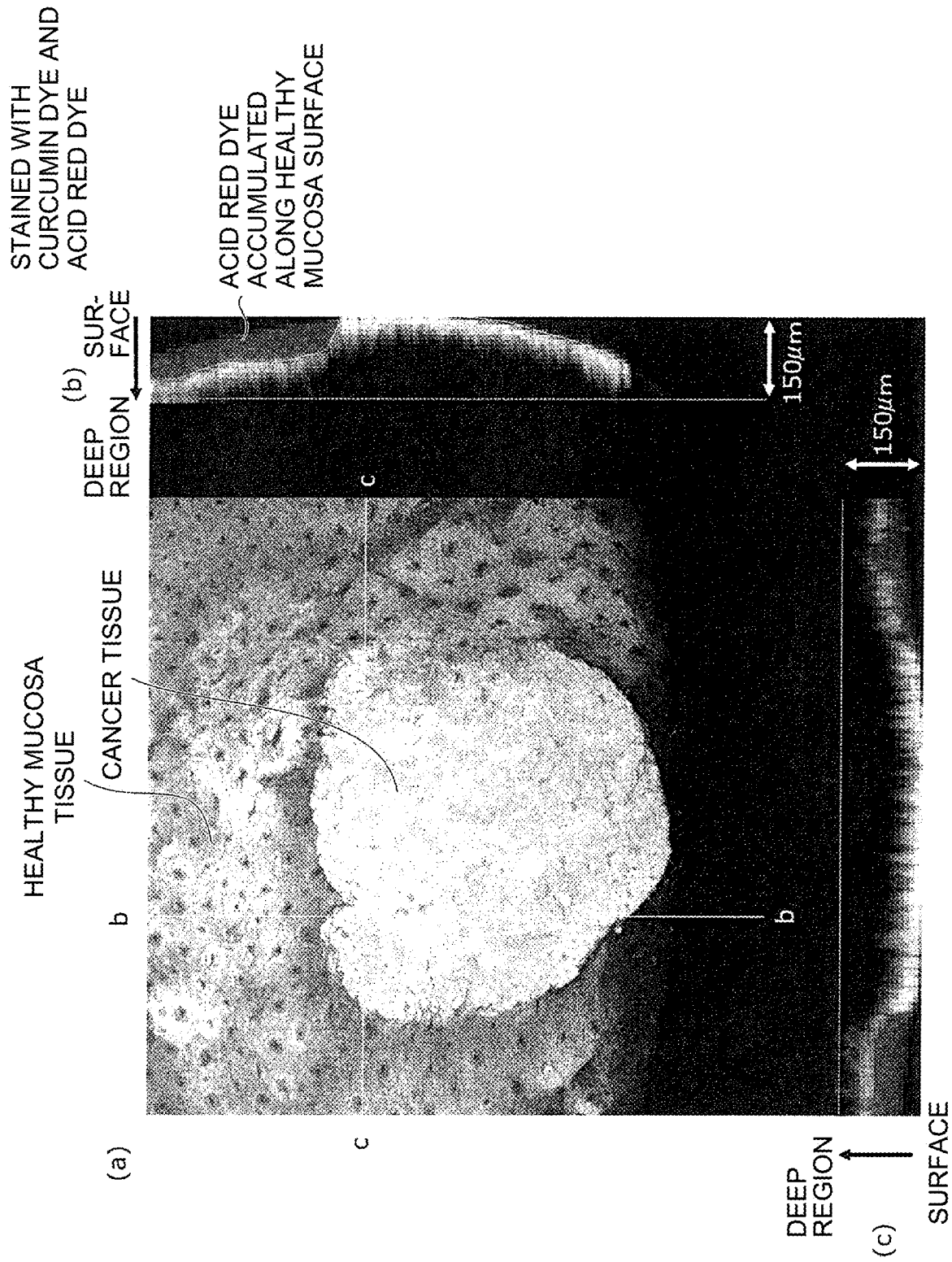

[Figure 34B]
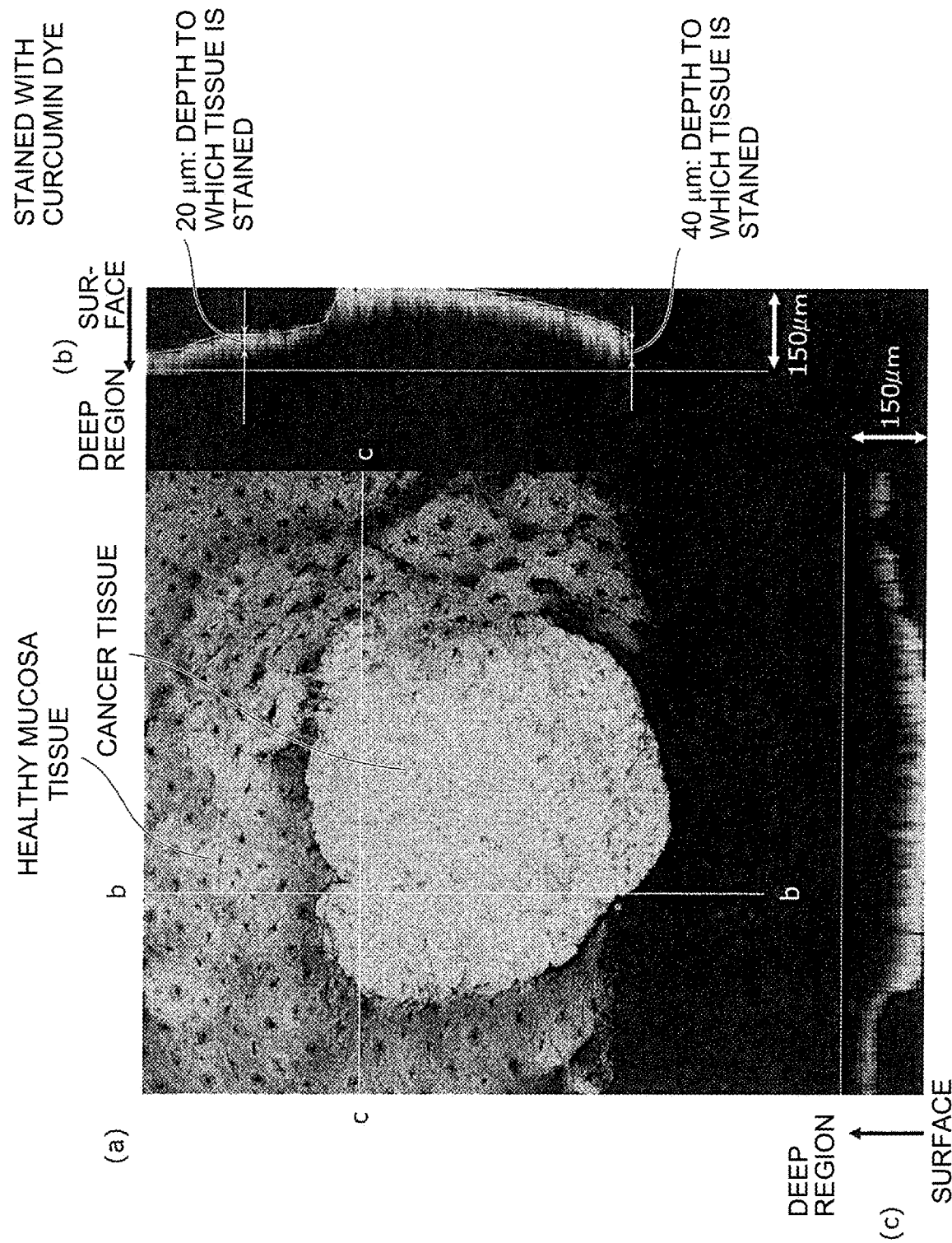

[Figure 34C]
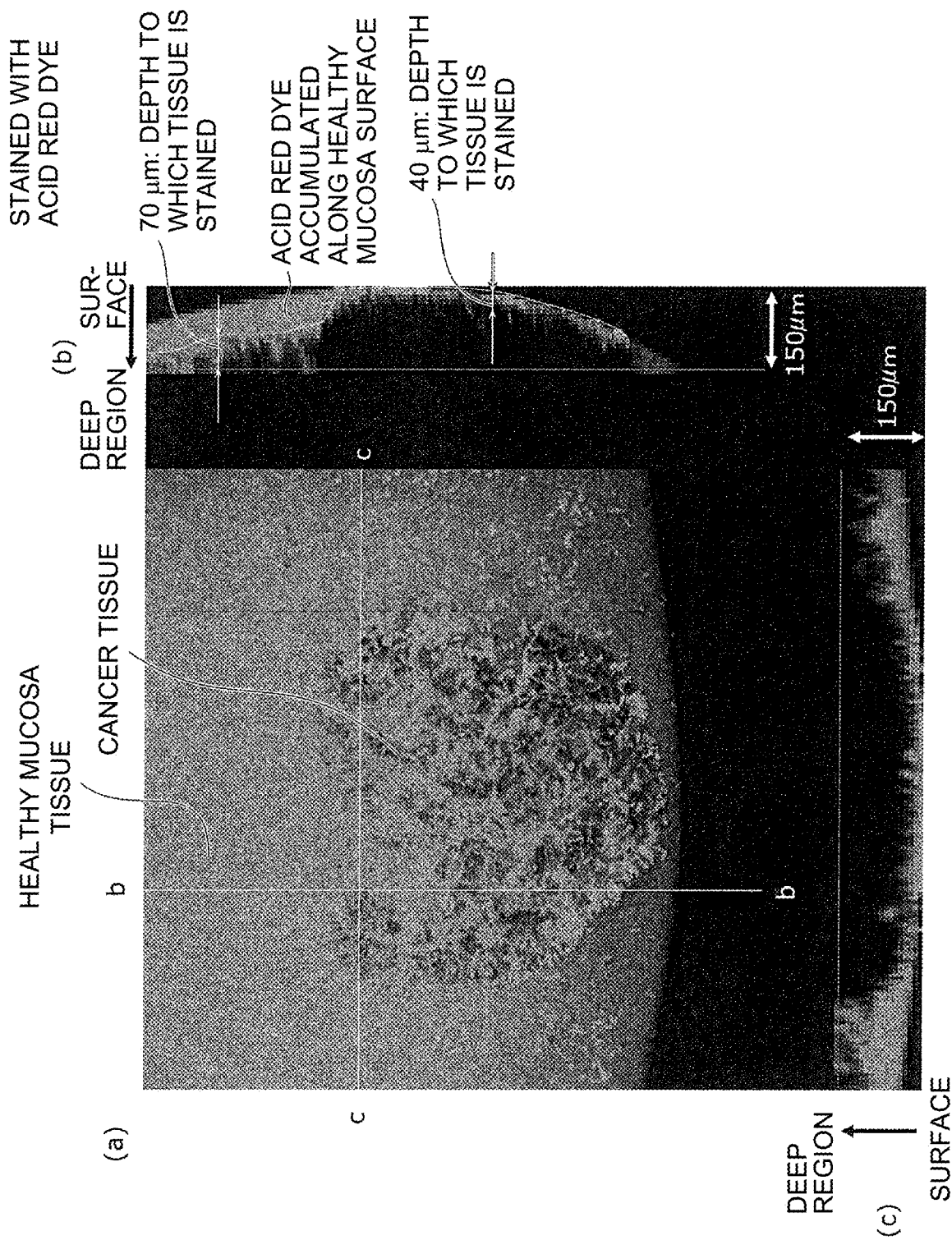

[Figure 35]
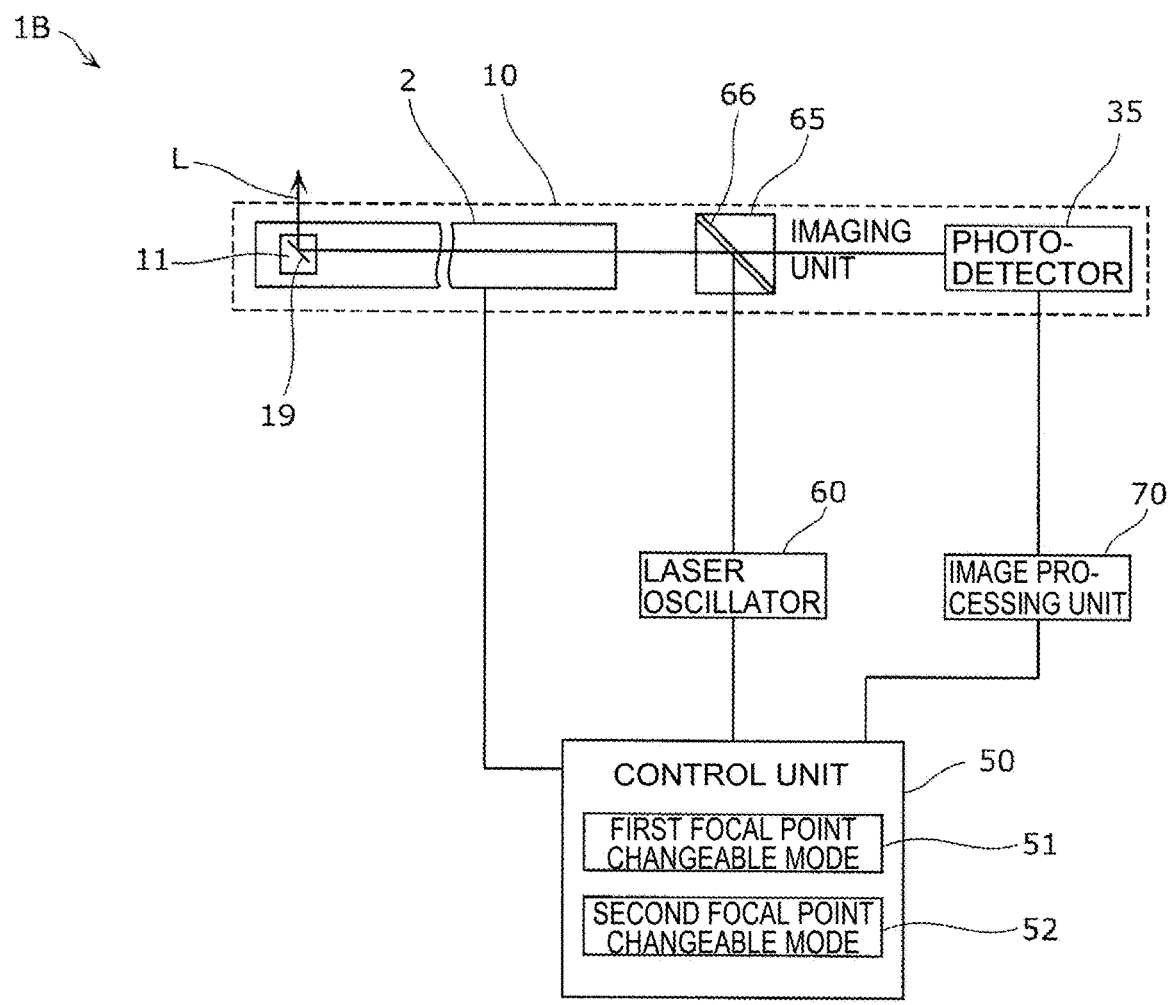

[Figure 36A]
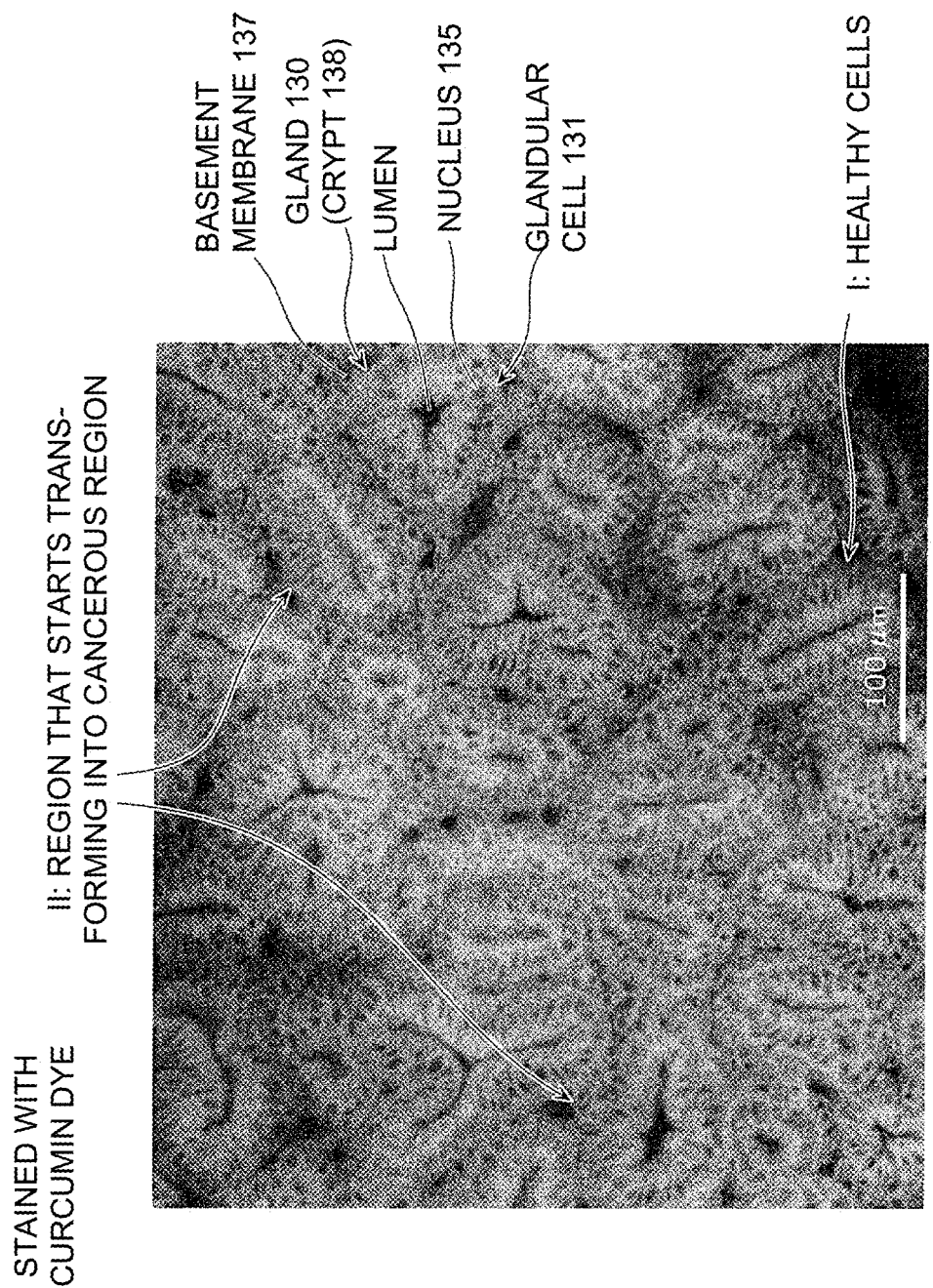

[Figure 36B]
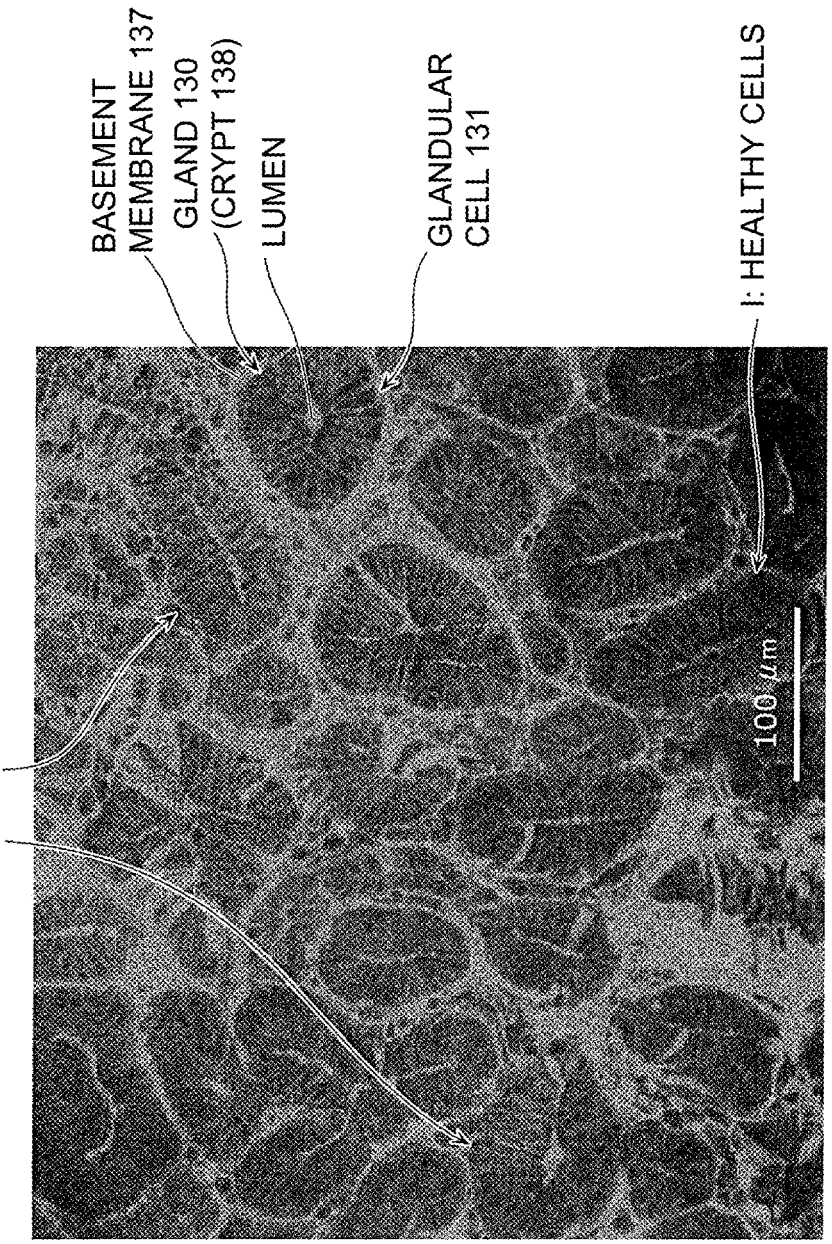

[Figure 36C]
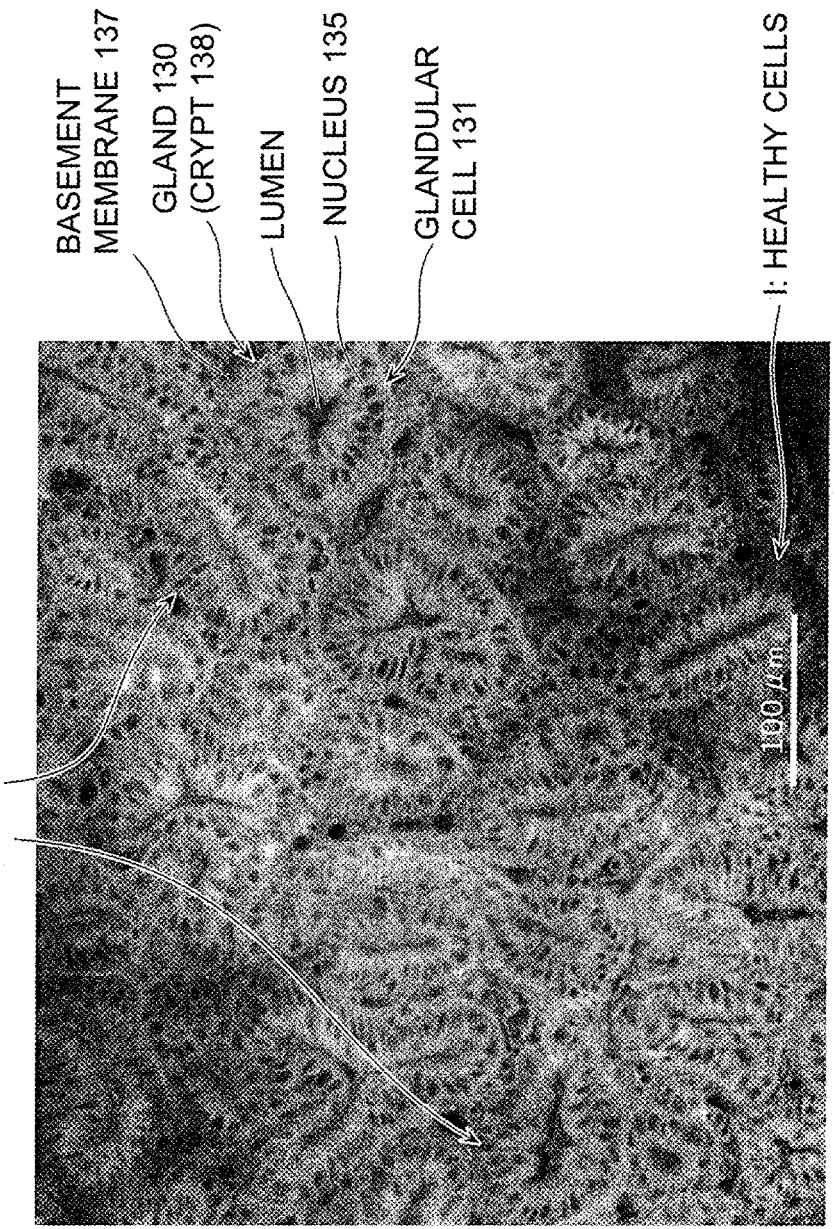

[Figure 37]
STAINED WITH CURCUMIN DYE
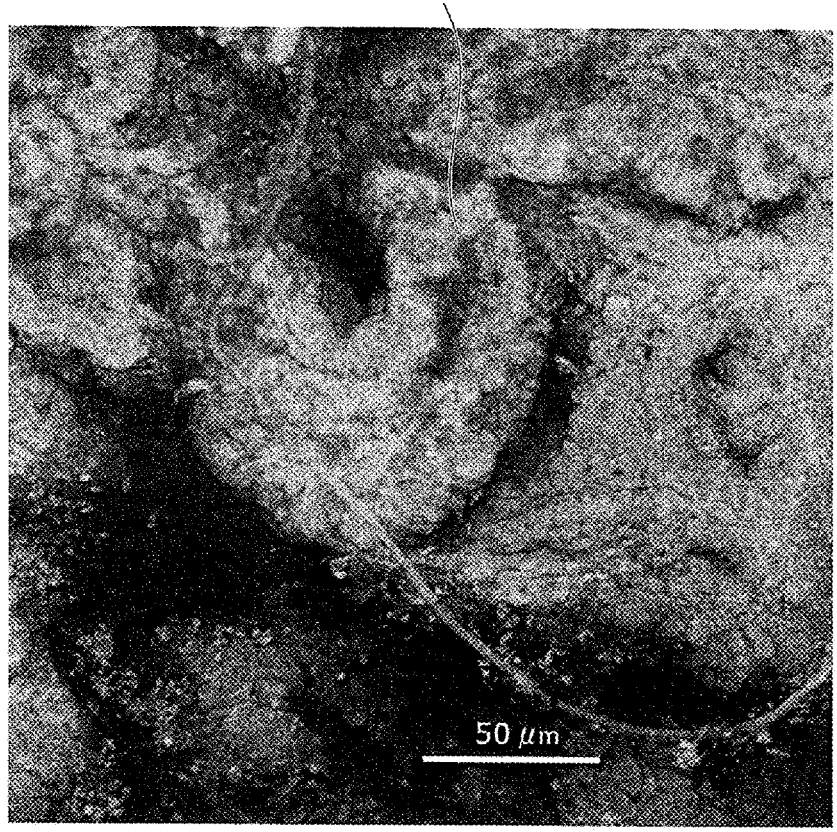

[Figure 38]
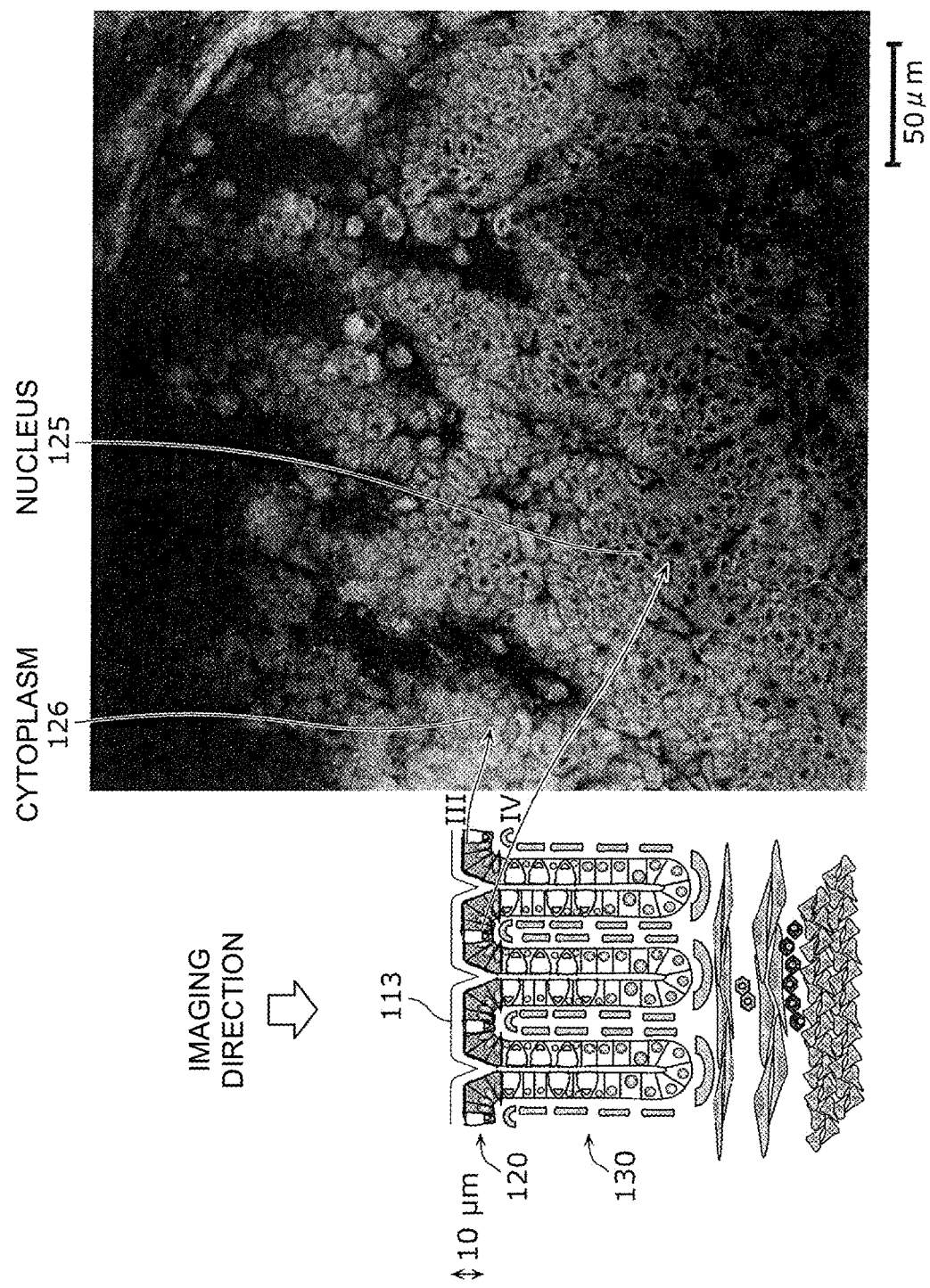

[Figure 39]
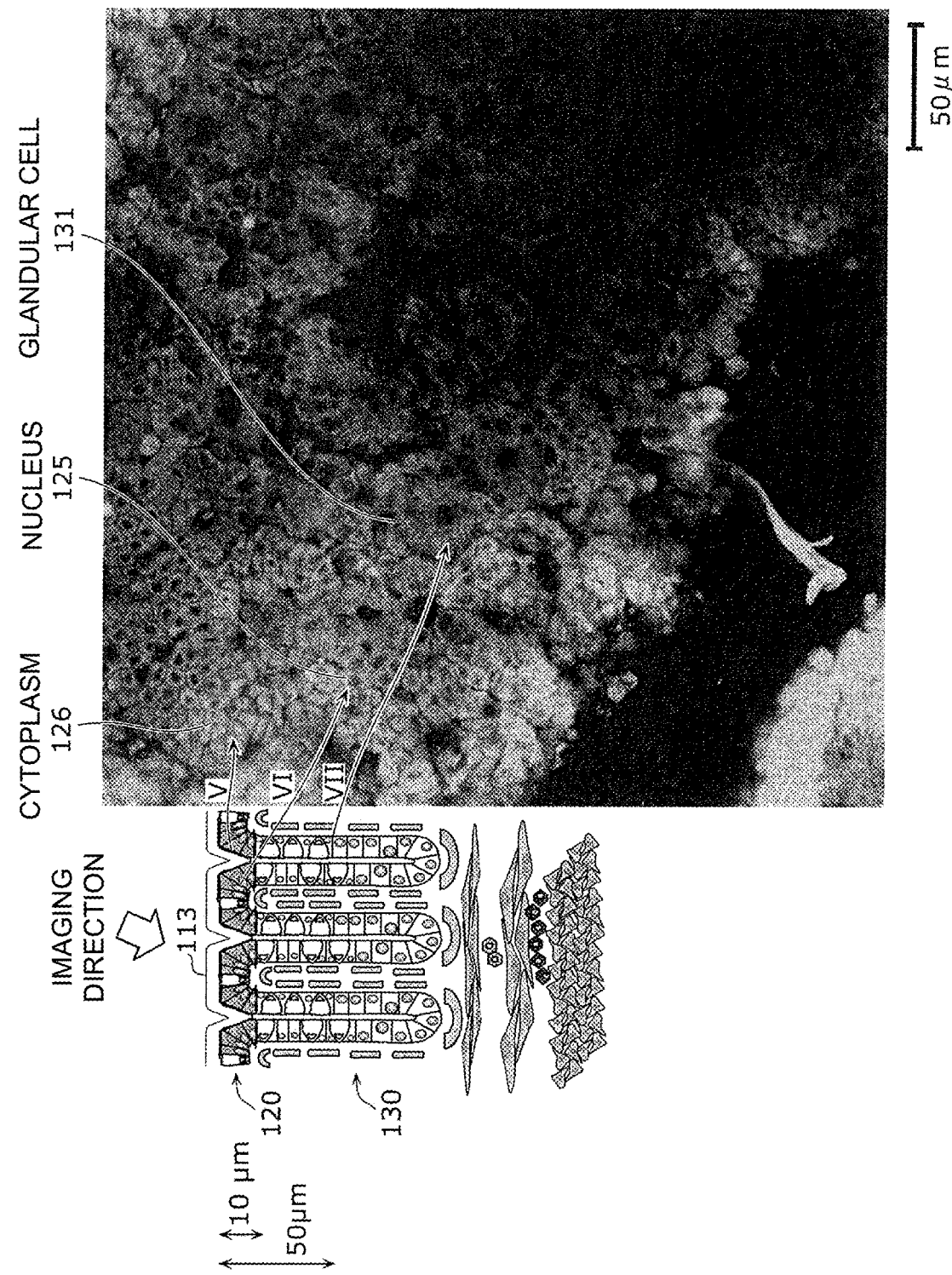

[Figure 40]
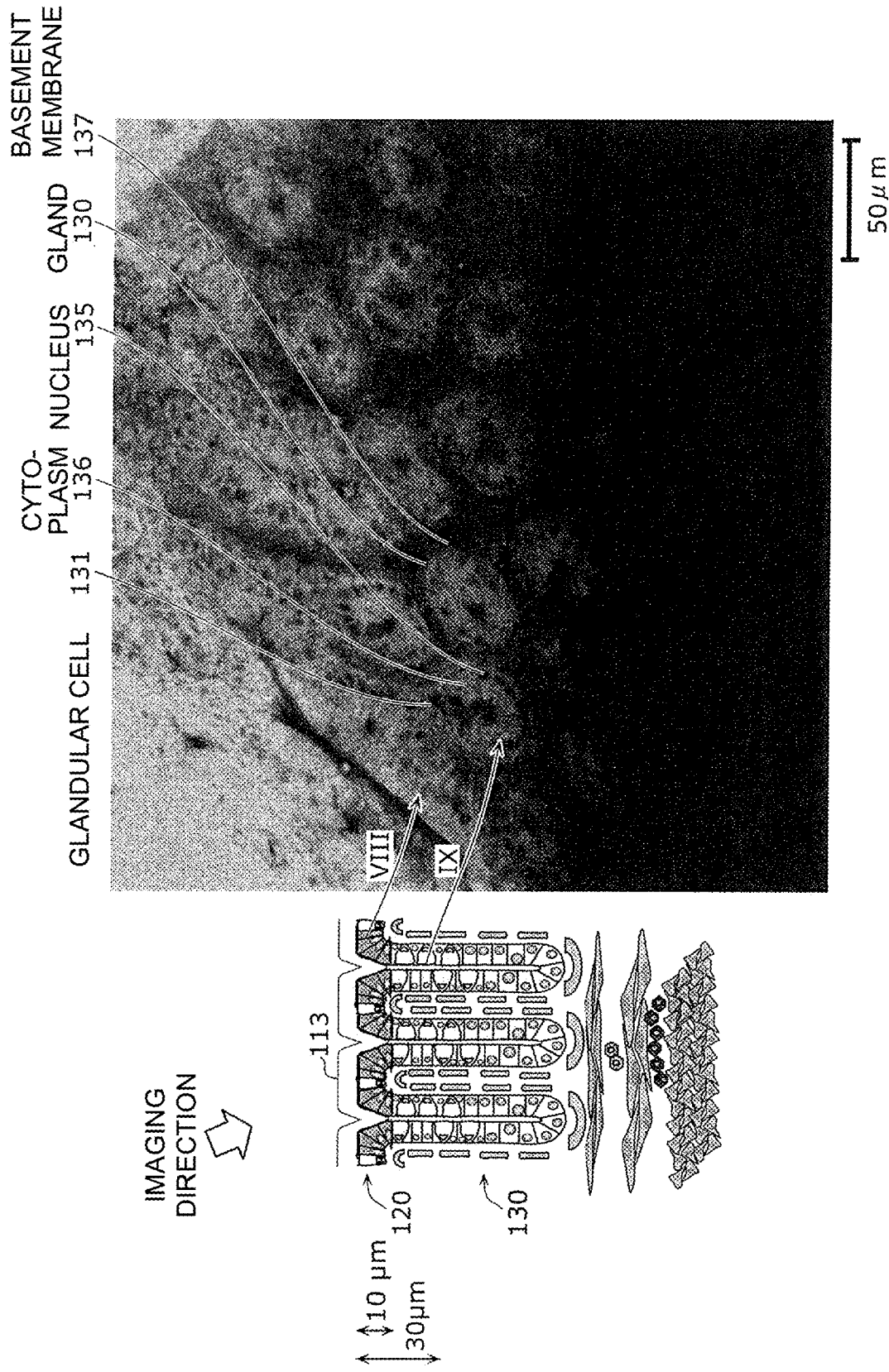

[Figure 41]
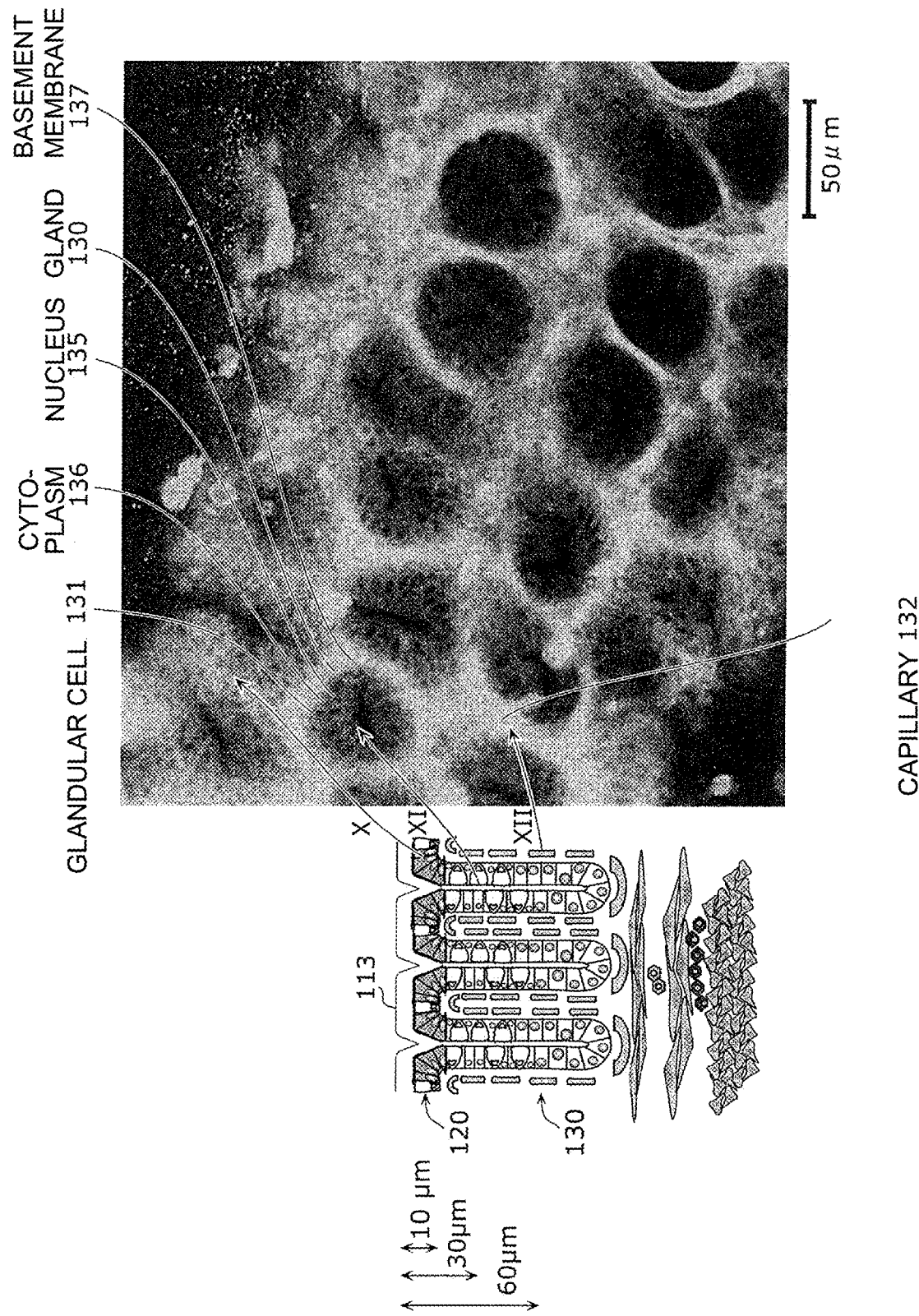

[Figure 42]
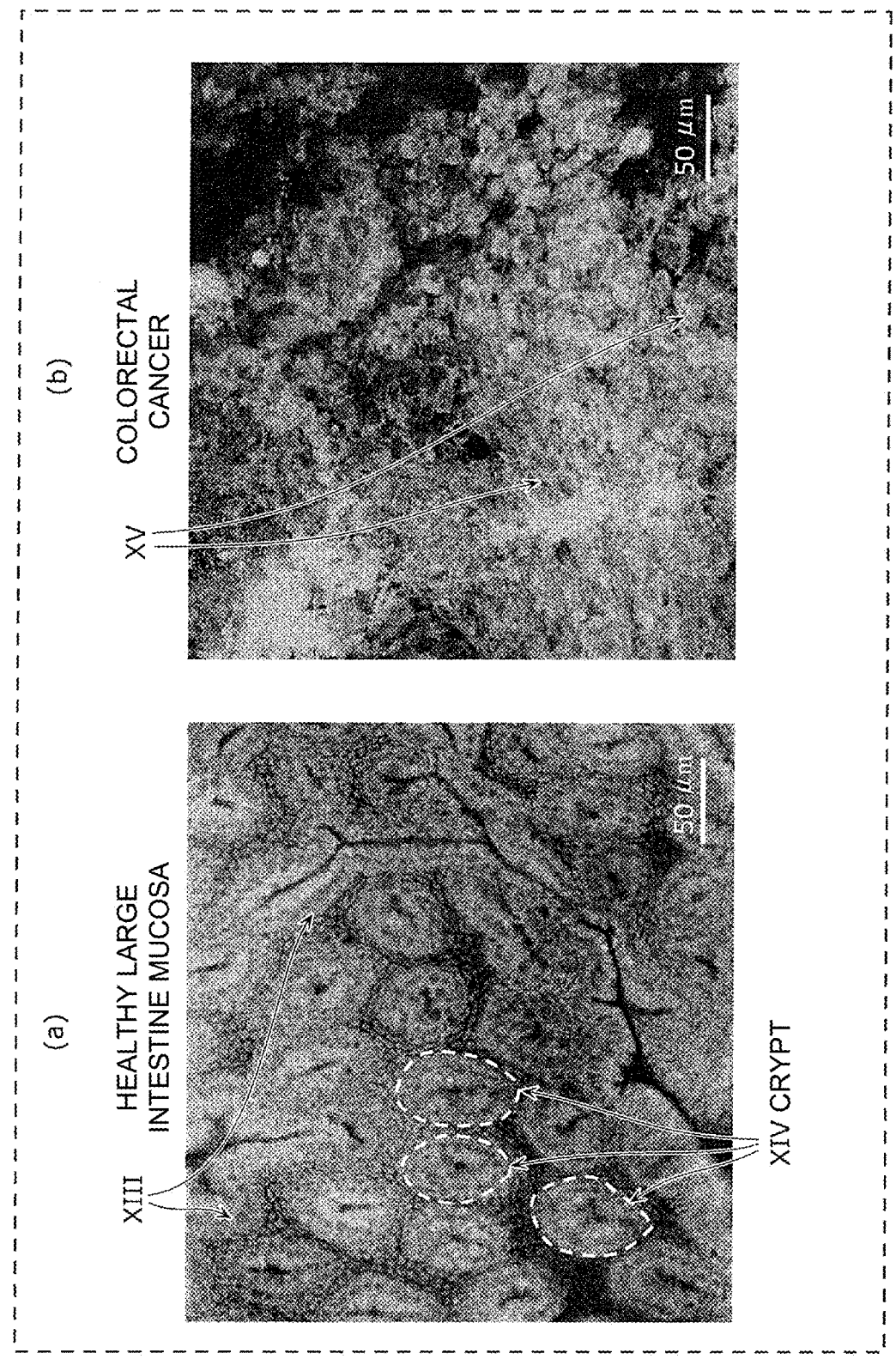

[Figure 43]
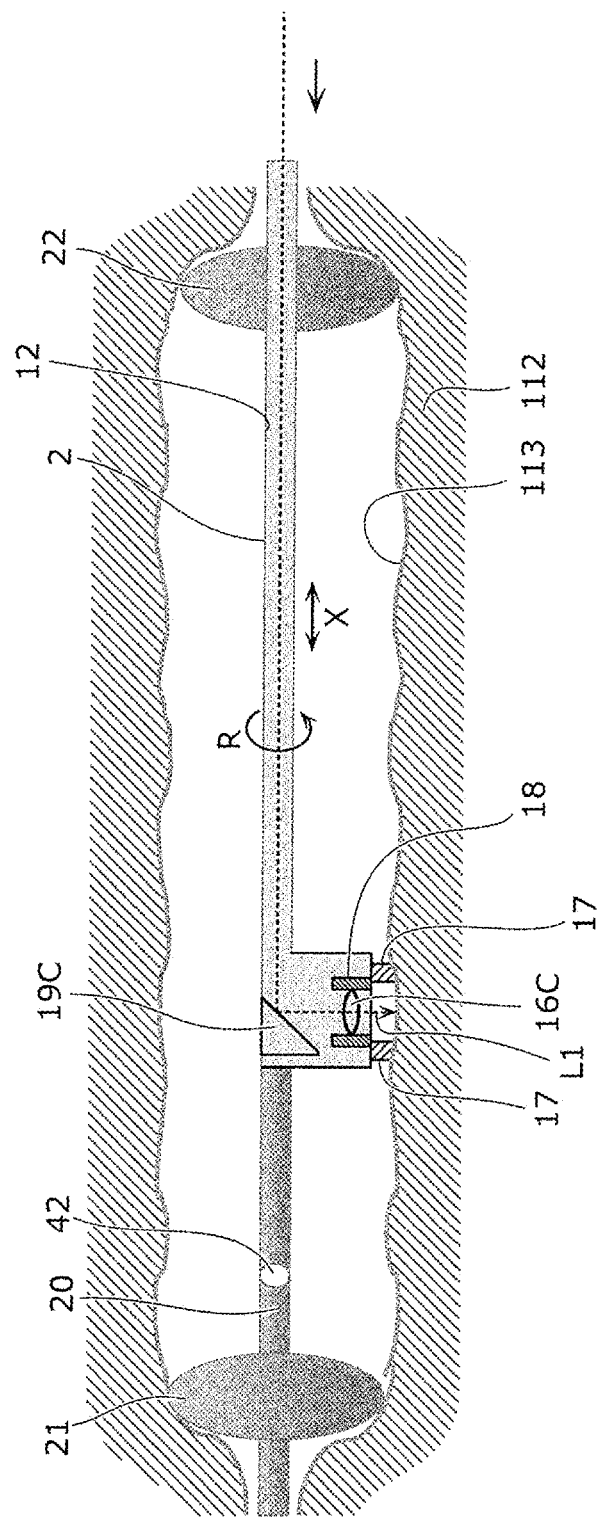

[Figure 44]
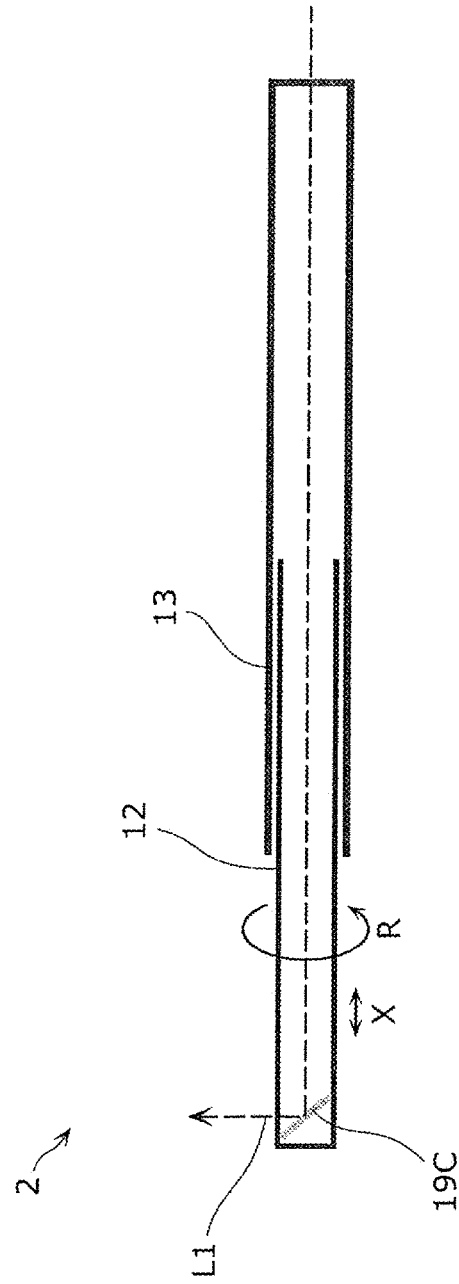

[Figure 45]
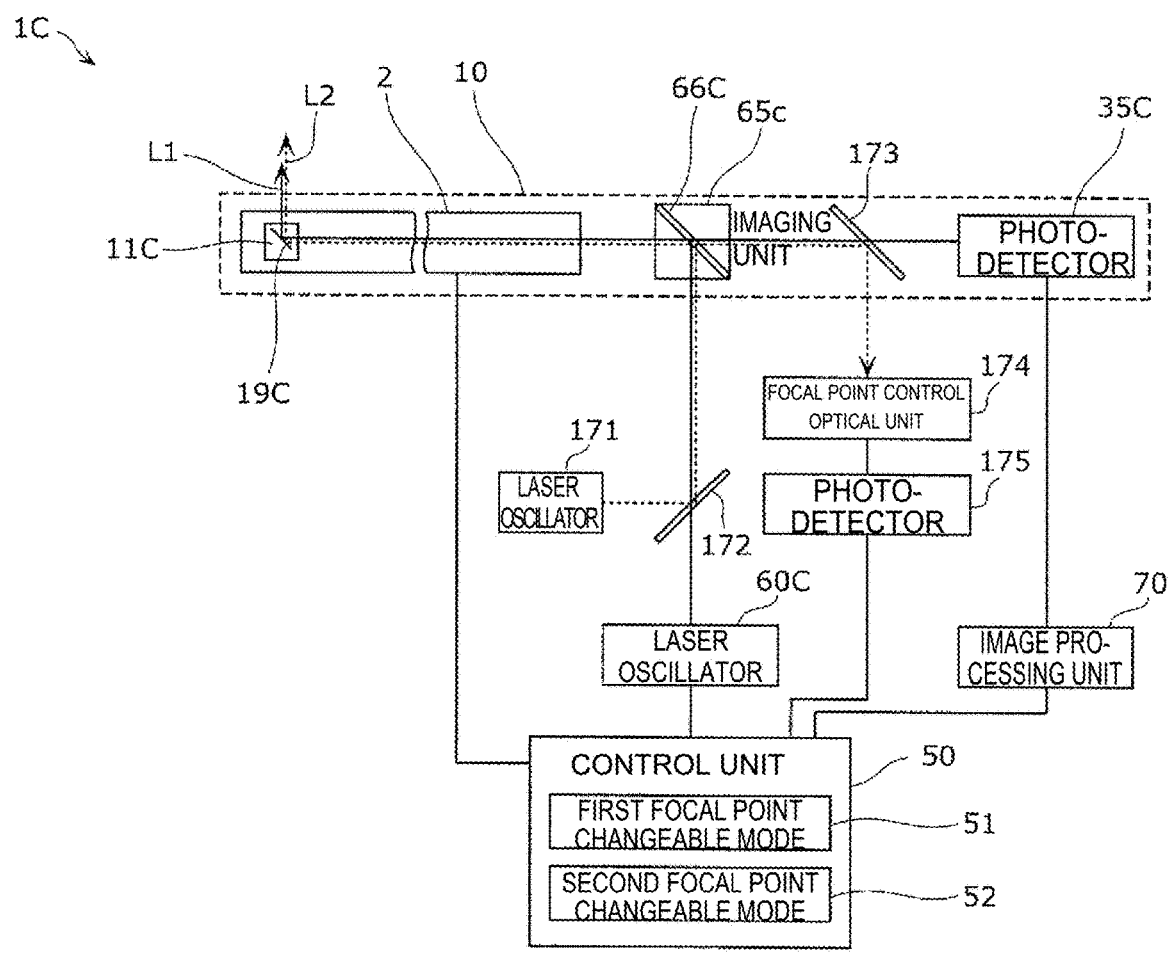

[Figure 46]
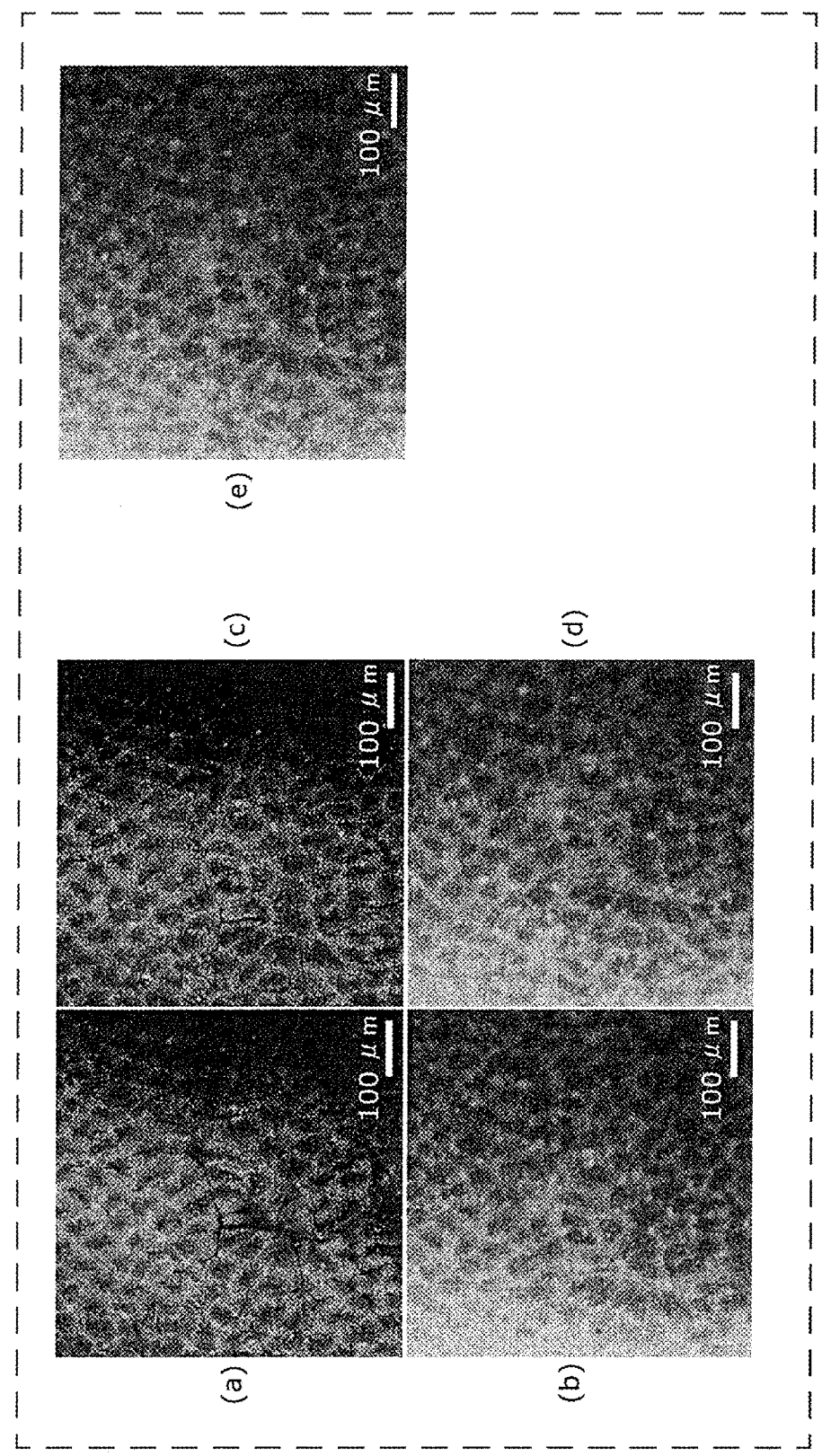

[Figure 47]
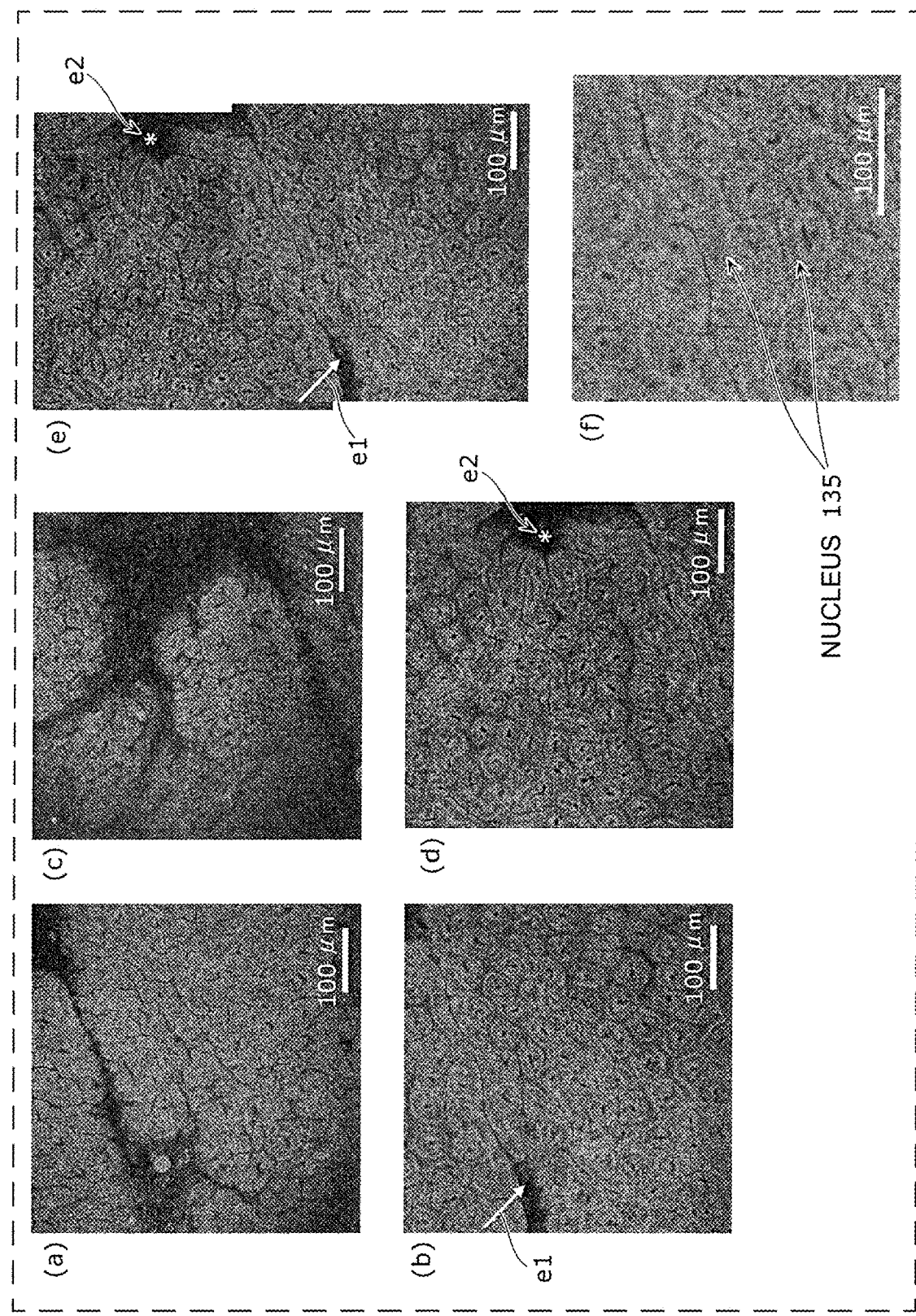

LASER ENDOSCOPE DEVICE

CROSS-REFERENCE TO RELATED APPLICATIONS

This application is a National Stage application of PCT/JP2017/006962, filed Feb. 23, 2017, which claims priority from Japanese application JP 2016-032520, filed Feb. 23, 2016.

TECHNICAL FIELD

The present invention relates to a laser endoscope device that images the interior of a living body.

BACKGROUND ART

In recent years, as a method for checking a lesion in a living body (digestive tract, for example), there is a known method for inserting an endoscope into the living body and checking whether or not a lesion, such as cancer cells, is present.

As an example of the method, Patent Literature 1 describes a method for staining a predetermined cell group in the living body and then applying multi-photon laser light to the stained cell group to image the cell morphology in the living body. According to the method described above, since the stained cell group emits fluorescence when the multi-photon laser light is applied thereto, a sharp image of the cell morphology in the living body can be obtained. Whether or not a lesion, such as cancer cells, is present can therefore be precisely checked.

CITATION LIST

Patent Literature

Patent Literature 1: International Publication No. WO 2014/157703

SUMMARY OF INVENTION

Technical Problem

However, the method described in Patent Literature 1, in which the obtained image is an image of a local region in the living body, only allows checking of whether or not a lesion is present in the imaged region. Further, from the standpoint of a patient who undergoes the examination, the patient cannot make sure whether or not a lesion is present in the region other than the imaged region and is therefore still anxious about his/her condition.

The present invention solves the problems described above, and an object of the present invention is to provide a laser endoscope device capable of imaging a cell morphology in a living body over a wide range with no missing part.

Solution to Problem

To achieve the object described above, a laser endoscope device according to an aspect of the present invention includes an imaging unit that includes an imaging head inserted into a living body and applies laser light to the living body via the imaging head to image the living body, a control unit that controls the imaging head in such a way that it scans while keeping a fixed distance from a cell surface of the living body, and an image processing unit that processes an image captured by the imaging unit, wherein the imaging unit images a plurality of imaging regions to be imaged as the imaging head moves in such a way that adjacent imaging regions have identical portions, and the image processing unit causes images of glands and/or crypts in the plurality of imaging regions to overlap with each other with the identical portions being aligned to generate a merged image.

In addition, to achieve the object described above, a laser endoscope device according to an aspect of the present invention includes an imaging unit that includes an imaging head inserted into a living body and applies laser light to the living body via the imaging head to image the living body, a control unit that controls the imaging head in such a way that it scans the entire inner circumference of the digestive tract while keeping a fixed distance from the inner wall surface of digestive tract of the living body and at the same time moves in the direction of circumference of the digestive tract, and an image processing unit that processes an image captured by the imaging unit, wherein the imaging unit images a plurality of imaging regions to be imaged as the imaging head moves in such a way that adjacent imaging regions have identical portions, and the image processing unit causes the plurality of imaging regions to overlap with each other with the identical portions being aligned to generate a merged panoramic image of entire inner circumference in the imaging range moved in the direction of the circumference of the digestive tract.

According to the present aspect, cell morphology n inside a living body can be imaged over a wide range with no missing part. In addition, according to the present aspect, the plurality of images obtained by the imaging have stable quality, whereby a merged image having a small amount of unevenness can be obtained when the plurality of images are merged with each other. Moreover, according to the present aspect, the state of inner wall of digestive tract can be grasped exhaustively based on panoramic images.

For example, the laser is multiphoton laser or confocal laser. The imaging head includes an objective lens and a focal point changer capable of changing a focal point position of the objective lens in a direction of depth from a cell surface of the living body. The control unit may change the focal point position by operating the focal point changer. The imaging unit may image the imaging regions at a predetermined depth out of depths deeper than or equal to 10 μm but shallower than or equal to 1000 μm below an inner wall surface inside the living body. Moreover, and the image processing unit may generate the merged image at the predetermined depth.

According to the present aspect, the cell morphology inside a living body at a predetermined depth out of the depths deeper than or equal to 10 μm but shallower than or equal to 1000 μm below an inner wall surface can be imaged over a wide range with no missing part.

For example, the control unit may control the movement of the imaging head in such a way that the imaging head scans the living body with a fixed distance from the imaging head to the living body maintained.

According to the present aspect, the plurality of images obtained by the imaging have stable quality, whereby a merged image having a small amount of unevenness can be obtained when the plurality of images are merged with each other.

For example, the imaging head may include an objective lens so disposed as to face the living body and a spacer provided around a space between the objective lens and the living body, and the control unit may control the movement of the imaging head in such a way that the spacer is in contact with the living body to maintain the fixed distance.

According to the present aspect, the distance between the living body and the objective lens is fixed, so that the living body can be precisely brought into focus through the lens, whereby a sharp image can be obtained.

For example, the living body may be a digestive tract, the control unit may control the imaging head in such a way that the imaging head moves along an inner circumference of the digestive tract, the imaging unit may image a plurality of imaging regions to be imaged as the imaging head moves in such a way that imaging regions adjacent to each other in the circumferential direction have identical portions, and the image processing unit may cause the plurality of imaging regions to overlap with each other with the identical portions being aligned to generate a panoramic image.

According to the present aspect, the panoramic image allows exhaustive grasp of the state of the inner wall of the digestive tract.

For example, a laser endoscope device may include a stain supplier that supplies a stain into the living body for selectively staining a cell group inside the living body in a chromatic color, wherein the control unit may control the imaging head in such a way that it revolves around an axis of digestive tract of the living body, the imaging unit may image a plurality of imaging regions to be imaged as the imaging head revolves in such a way that imaging regions adjacent to each other in the revolutional direction have identical portions, and the image processing unit may cause the plurality of imaging regions to overlap with each other with the identical portions being aligned to generate the merged image.

For example, a laser endoscope device may include a stain supplier that supplies a stain into the living body for selectively staining a cell group inside the living body in a chromatic color as well as first and second balloons which are disposed in front of and behind the imaging head in the axial direction of digestive tract of the living body and expand to form a closed space inside the digestive tract, wherein the stain supplier may include a supply port which supplies a fluid into the closed space and a recovery port which recovers the fluid flowing into the closed space, the control unit may control the imaging head in the closed space in such a way that it revolves around an axis of the digestive tract, the imaging unit may image a plurality of imaging regions to be imaged as the imaging head revolves in such a way that imaging regions adjacent to each other in the revolutional direction have identical portions, and the image processing unit may cause the plurality of imaging regions to overlap with each other with the identical portions being aligned using the gland, the crypt or solitary lymphatic nodule in the imaging regions as marks to generate the merged image.

According to the present aspect, sharp images of stained cell groups can be obtained. In addition, according to the present aspect, the state of inner wall of digestive tract can be grasped exhaustively.

For example, the control unit may control the imaging head in such a way that the imaging head orbits around an axis of the digestive tract.

According to the present aspect, the imaging can be performed with no missing part with each imaging region and the position on the inner wall of the digestive tract related to each other.

For example, the control unit may control the imaging head in such a way that the imaging head helically moves around the axis of the digestive tract.

According to the present aspect, the inner wall of the digestive tract can be continuously imaged in a short period.

For example, the control unit may control the imaging head in such a way that it moves along a tract longitudinal direction of the digestive tract. The imaging unit may image a plurality of imaging regions to be imaged as the imaging head moves in such a way that imaging regions adjacent to each other in the tract longitudinal direction have identical portions. Moreover, the image processing unit may cause the plurality of imaging regions to overlap with each other with the identical portions being aligned to generate a the merged image.

According to the present aspect, the position (coordinates) where a lesion is present in the tract longitudinal direction of the digestive tract can be grasped.

For example, the stain supplier may supply a stain that specifically stains cancer cells and a stain that specifically stains ordinary cells into the living body. The imaging unit may image a plurality of imaging regions at different depths as the focal point position is changed. The image processing unit may place the plurality of images obtained by the imaging performed by the imaging unit in correspondence with the focal point positions to generate a stereoscopic image of the interior of the living body or a cross-sectional image of the stereoscopic image. Moreover, the control unit may determine degrees of cancer development based on the stereoscopic image or the cross-sectional image by comparing the penetration depth of the stain that specifically stains cancer cells with that of the stain that specifically stains ordinary cells.

According to the present aspect, cell morphology inside a living body at a predetermined depth can be grasped and degrees of cancer development can be determined.

For example, the control unit may have a first focal point changeable mode in which the focal point position is changed by a first interval and a second focal point changeable mode in which the focal point position is changed by a second interval smaller than the first interval, and in a case where the imaging is performed in the first focal point changeable mode and an resultant image obtained by the imaging contains a portion suspicious of a lesion, the control unit may perform the imaging in the second focal point changeable mode in a vicinity of a focal point position where the image of the portion suspicious of a lesion has been captured.

According to the present aspect, the imaging can be performed exhaustively with the imaging period shortened.

For example, the control unit may store an image of healthy cells having no lesion in advance and compare any of the images obtained in the first focal point changeable mode with the image of healthy cells in terms of at least one of morphology and brightness to evaluate the suspicion of a lesion.

According to the present aspect, suspicion of a lesion can be objectively evaluated in a short period.

For example, in a case where the image obtained by the imaging unit contains cells having a lesion, the control unit may increase power of the laser light as compared with power in the imaging and applies the laser light having the increased power to the cells having a lesion to remove the cells having a lesion.

According to the present aspect, the cells having a lesion can be reliably removed in an early stage of the lesion.

For example, the laser light may be multi-photon laser light.

According to the present aspect, tissue cells below the surface of the living body at a depth of about 1 mm at the deepest can be reliably imaged.

For example, the laser endoscope device may further include a stain supplier that supplies a stain for selectively staining a cell group in the living body in a chromatic color into the living body, and the imaging unit may image the cell group stained with the stain supplied from the stain supplier.

According to the present aspect, a sharp image of the stained cell group can be obtained.

For example, the laser endoscope device may further include a stain supplier that supplies stains for staining a cell group in the living body in at least two selective chromatic colors different from each other in accordance with a cell type into the living body, and the imaging unit may image the cell group stained with the stains supplied from the stain supplier in the at least two colors.

According to the present aspect, a sharp image of the cell group stained in the at least two colors can be obtained. Further, for example, a plurality of types of tissue in the inner wall of the digestive tract can be simultaneously checked in a single image.

A laser endoscope device according to another aspect of the present invention includes a stain supplier that supplies stains for staining a cell group in a living body in at least two selective chromatic colors different from each other in accordance with a cell type into the living body and an imaging unit that images the cell group stained with the stains supplied from the stain supplier by applying laser light to the cell group.

According to the present aspect, a sharp image of the cell group stained in the at least two colors can be obtained. Further, for example, a plurality tissue cells in the inner wall of the digestive tract can be simultaneously checked in a single image.

For example, the stain may be a stain containing a curcumin-based compound and Acid Red or two stains formed of a stain containing a curcumin-based compound and a stain containing Acid Red.

According to the present aspect, the cell group in the living body can be reliably stained in two colors, whereby a sharp image can be obtained.

For example, the stain may be a stain containing a curcumin-based compound and FastGreen FCF or two stains formed of a stain containing a curcumin-based compound and a stain containing FastGreen FCF.

According to the present aspect, the cell group in the living body can be reliably stained in two colors, whereby a sharp image can be obtained.

A laser endoscope device according to another aspect of the present invention includes a stain supplier that supplies into a living body a stain for specifically staining in a chromatic color a cancer cell surrounding cell group other than cancer cells and located around the cancer cells in a cell group in the living body and an imaging unit that applies laser light to the cell group located in the living body and stained with the stain supplied from the stain supplier to capture an image that allows visual discrimination of the cancer cell surrounding cell group.

According to the present aspect, a sharp image of the cancer cell surrounding cell group located around the cancer cells can be obtained.

For example, the stain may be a stain containing Rose-Bengal that specifically stains a cancer cell surrounding cell group other than the cancer cells located around cancer cells among the cell groups inside the living body in a chromatic color.

According to the present aspect, a sharp image of the cancer cell surrounding cell group located around the cancer cells can be reliably obtained.

A laser endoscope device according to another aspect of the present invention includes an imaging unit that includes an imaging head inserted into a living body and applies laser light to the living body via the imaging head to image the living body and a control unit that controls operation of the imaging head. The imaging head includes an objective lens and a focal point changer capable of changing a focal point position of the objective lens in a depth direction from a cell surface of the living body. The control unit causes the focal point changer to operate to change the focal point position. The imaging unit images a plurality of imaging regions at different depths from a mucosa surface in the living body as the focal point position is changed.

According to the present aspect, the cell morphology in the living body at a predetermined depth can be grasped.

For example, the imaging unit may image the imaging regions over a predetermined depth range out of depths deeper than or equal to 0 μm but shallower than or equal to 1000 μm below the mucosa surface in the living body and stores each of the captured images and the depth information with the captured image and the depth information related to each other, the laser endoscope device may further include an image processing unit that processes the images captured by the imaging unit, and the image processing unit may place the plurality of images obtained by the imaging performed by the imaging unit in correspondence with the focal point positions to generate a stereoscopic image of the interior of the living body.

According to the present aspect, the cell morphology in the living body at the depths deeper than or equal to 0 μm but shallower than or equal to 1000 μm below the mucosa surface can be grasped.

The laser endoscope device may further include a stain supplier that supplies a stain for selectively staining a cell group in the living body in a chromatic color into the living body, and the imaging unit may image the cell group stained with the stain supplied from the stain supplier.

According to the present aspect, a sharp image of the stained cell group can be obtained.

The laser endoscope device may further include a stain supplier that supplies stains for staining a cell group in the living body in at least two selective chromatic colors different from each other in accordance with a cell type into the living body, and the imaging unit may image the cell group stained with the stains supplied from the stain supplier in the at least two colors.

According to the present aspect, a sharp image of the cell group stained in the at least two colors can be obtained. Further, for example, a plurality of types of tissue in the inner wall of the digestive tract can be simultaneously checked in a single image.

The laser endoscope device may further include a stain supplier that supplies into the living body a stain for specifically staining in a chromatic color a cancer cell surrounding cell group other than cancer cells and located around the cancer cells in a cell group in the living body, and the imaging unit may image the cancer cell surrounding cell group stained with the stain supplied from the stain supplier.

According to the present aspect, a sharp image of the cancer cell surrounding cell group located around the cancer cells can be obtained.

For example, the image processing unit may cut the plurality of images at a position containing the stained cell group to generate a cross-sectional image of the stained cell group, and the control unit may evaluate whether the cell group displayed in the cross-sectional image is suspicious of a lesion based on a depth to which the cell group has been stained.

According to the present aspect, suspicion of a lesion can be objectively evaluated.

Advantageous Effects of Invention

According to the present invention, there is provided a laser endoscope device capable of imaging a cell morphology in a living body over a wide range with no missing part.

Further, the primary configuration of the present invention allows non-coincidental wide-range exhaustive detection of a microscopic lesion, such as ultra-early-stage cancer (diameter ranging from 0.2 mm to 1 mm) the presence of which cannot be detected with an existing endoscope because the size of the lesion is too small.

BRIEF DESCRIPTION OF DRAWINGS

FIG. 1 is a diagrammatic view showing the arrangement of the cells of the large intestine, which is an example of the digestive tract.

FIG. 2 diagrammatically shows cancer cells that develop in the digestive tract.

FIG. 3 is a diagrammatic view showing that the inner wall of the digestive tract is imaged under a multiphoton laser microscope.

FIG. 4 shows images of epithelial cells, glandular cells, and other parts stained with a stain containing curcumin and then imaged under the multiphoton laser microscope.

FIG. 5 shows images of capillaries, connective tissue, and other parts stained with a stain containing Acid Red and then imaged under the multiphoton laser microscope.

FIG. 6 shows images of the inner wall of the digestive tract double-stained with a stain containing curcumin and a stain containing Acid Red and then imaged under the multiphoton laser microscope.

FIG. 7 shows images of the inner wall of the digestive tract stained with a stain containing Rose Bengal and then imaged under the multiphoton laser microscope.

FIG. 8 is a diagrammatic view showing that the inner wall of the digestive tract is imaged over the entire circumference thereof under the multiphoton laser microscope.

FIG. 9 is a merged image of the inner wall of the digestive tract stained with the stain containing Acid Red.

FIG. 10A is a merged image of the inner wall of the digestive tract stained with the stain containing curcumin and the stain containing Acid Red.

FIG. 10B shows an example of a stereoscopic image reconstructed from the panoramic image of the inner wall of the digestive tract.

FIG. 11 shows a state after an insertion tube is inserted into a digestive tract in a laser endoscope device according to a first embodiment.

FIG. 12 shows an example of a stain supplier for supplying a stain in the laser endoscope device according to the first embodiment.

FIG. 13 The section (a) of FIG. 13 shows that the inner wall of the digestive tract is planarized by using the laser endoscope device according to the first embodiment, and the section (b) of FIG. 13 is a diagrammatic view showing a front-end-side end portion of the laser endoscope device.

FIG. 14 is a schematic view showing the entirety of an endoscope in the laser endoscope device according to the first embodiment.

FIG. 15 is a block diagram showing the control configuration of the laser endoscope device according to the first embodiment.

FIG. 16 is a diagrammatic view showing that the inner wall of the digestive tract is imaged under the laser microscope according to the first embodiment.

FIG. 17A describes the action of the laser endoscope device according to the first embodiment.

FIG. 17B describes the action of the laser endoscope device according to the first embodiment.

FIG. 17C describes the action of the laser endoscope device according to the first embodiment.

FIG. 17D describes the action of the laser endoscope device according to the first embodiment.

FIG. 17E describes the action of the laser endoscope device according to the first embodiment.

FIG. 18 is a flowchart showing an example of the action of the laser endoscope device.

FIG. 19 is a diagrammatic view showing that a laser endoscope device according to Variation 1 of the first embodiment is used to generate a panoramic image.

FIG. 20 is a diagrammatic view showing that a laser endoscope device according to Variation 2 of the first embodiment is used to image the interior of a living body.

FIG. 21 is a diagrammatic view showing that a laser endoscope device according to Variation 3 of the first embodiment is used to image the interior of a living body.

FIG. 22 is a diagrammatic view showing that a laser endoscope device according to Variation 4 of the first embodiment is used to image the interior of a living body.

FIG. 23 is a diagrammatic view showing that a laser endoscope device according to Variation 5 of the first embodiment is used to image the interior of a living body.

FIG. 24 is a diagrammatic view showing that a laser endoscope device according to Variation 6 of the first embodiment is used to image the interior of a living body.

FIG. 25 is a diagrammatic view showing that a laser endoscope device according to Variation 7 of the first embodiment is used to image the interior of a living body.

FIG. 26 is a diagrammatic view showing that a laser endoscope device according to Variation 8 of the first embodiment is used to image the interior of a living body.

FIG. 27 is a diagrammatic view showing that a laser endoscope device according to Variation 9 of the first embodiment is used to image the interior of a living body.

FIG. 28 is a diagrammatic view showing that a laser endoscope device according to Variation 10 of the first embodiment is used to stain the interior of a living body.

FIG. 29 is a diagrammatic view showing that a laser endoscope device according to Variation 11 of the first embodiment is used to image the interior of a living body.

FIG. 30 is a diagrammatic view showing that a laser endoscope device according to Variation 12 of the first embodiment is used to image the interior of a living body.

FIG. 31 is a diagrammatic view showing that the laser endoscope device according to Variation 12 of the first embodiment is used to image the interior of a living body.

FIG. 32A is a diagrammatic view showing that the inner wall of the digestive tract is imaged over the entire circumference thereof under the multiphoton laser microscope.

FIG. 32B shows a panoramic image illustrating a cell morphology in a position below the inner wall surface (mucosa surface) at a depth of 50 μm.

FIG. 33 shows an endoscope of a laser endoscope device according to a second embodiment.

FIG. 34A shows three-dimensional data images showing not only a cell morphology over a predetermined depth range from an inner wall surface (mucosa surface) but an extracted color region stained with both a curcumin dye and an Acid Red dye.

FIG. 34B shows three-dimensional data images showing not only the cell morphology over the predetermined depth range from the inner wall surface (mucosa surface) but an extracted color region stained with the curcumin dye.

FIG. 34C shows three-dimensional data images showing not only the cell morphology over the predetermined depth range from the inner wall surface (mucosa surface) but an extracted color region stained with the Acid Red dye.

FIG. 35 is a block diagram showing the control configuration of a laser endoscope device according to a third embodiment.

FIG. 36A shows an image illustrating a cell morphology in a position below an inner wall surface (mucosa surface) at a depth of 50 μm and representing an extracted color region stained with the curcumin dye.

FIG. 36B shows an image illustrating the cell morphology in the position below the inner wall surface (mucosa surface) at the depth of 50 μm and representing an extracted color region stained with the Acid Red dye.

FIG. 36C shows an image illustrating the cell morphology in the position below the inner wall surface (mucosa surface) at the depth of 50 μm and representing an extracted color region stained with both the curcumin dye and the Acid Red dye.

FIG. 37 shows a stomach cancer cell group stained with the curcumin dye.

FIG. 38 is an image of a cell group in a living body captured along the direction perpendicular to an inner wall surface (mucosa surface) under a confocal laser microscope.

FIG. 39 is an image of a cell group in a living body captured obliquely left downward with respect to an inner wall surface (mucosa surface) under the confocal laser microscope.

FIG. 40 is an image of the cell group in the living body captured obliquely right downward with respect to the inner wall surface (mucosa surface) under the confocal laser microscope.

FIG. 41 is an image of the cell group in the living body captured obliquely left downward with respect to the inner wall surface (mucosa surface) under the confocal laser microscope.

FIG. 42 is an image of a living cell stained with a stain solved by using an optimized solving method and captured with the confocal laser microscope, the section (a) showing an image of healthy large intestine mucosa and the section (b) showing an image showing colorectal cancer.

FIG. 43 is a schematic view showing a front-end-side end portion of an endoscope of a laser endoscope device according to a fourth embodiment.

FIG. 44 is a schematic view showing the entire endoscope.

FIG. 45 is a block diagram showing the control configuration of the laser endoscope device.

FIG. 46 shows images of inner planes of an unstained colorectal mucosa captured under the confocal laser microscope.

FIG. 47 shows images of inner planes of the unstained colorectal mucosa captured under the multiphoton laser microscope.

DESCRIPTION OF EMBODIMENTS (Finding 1 on which Present Invention is Based)

The present invention is based on findings 1, 2, 3, 4, 5, and 6. Out of the findings, the finding 1 on which the present invention is based and a primary configuration of the invention associated with the finding 1 will first be described.

The relationship between the internal structure of a living body and cancer cells will first be described.

The interior of a living body contains the digestive tract, the respiratory system, the renal/urinary system, the utero-ovarian reproductive system, and other organs, the cerebrospinal nervous system, and other body sites. Examples of the digestive tract may include the esophagus, the stomach, the small intestine, and the large intestine.

FIG. 1 is a diagrammatic view showing the arrangement of the cells of the large intestine, which is an example of a digestive tract 112. For example, the inner wall of the large intestine is formed of a gland 130, which secretes mucus, and an epithelium 120, which is located in a portion closer to an inner wall surface (mucosa surface) 113 than the gland 130 and absorbs water when coming into contact with food. The epithelium 120 is formed of a plurality of epithelial cells 121 arranged along the inner wall surface 113. The epithelial cells 121 each have a nucleus 125 and cytoplasm 126. The gland 130 is so shaped that part of the epithelium 120 is recessed in the form of a pot. The gland 130 is formed of a plurality of glandular cells 131, and the glandular cells 131 each have a nucleus 135 and cytoplasm 136. The recessed portions of the gland 130 are called crypts of the gland 130. A basement membrane 137, capillaries 132, and connective tissue 133 are formed in the portion inside the epithelial cells 121 and the portion around the glandular cells 131. A thin layer of the mucus secreted from the gland 130 is formed on the surfaces of the epithelial cells 121, and the epithelial cells 121 are protected by the mucus layer.

The sizes of the nuclei 125 and 135, the arrangement of the nuclei 125 and 135, and the distances from the nuclei 135 to the basement membrane 137 in the internal structure of a living body are important evaluation factors in pathological diagnosis of cancer and other diseases.

FIG. 2 diagrammatically shows a cancer cell population 152, which develops in the digestive tract 112. The early-stage cancer cell population 152, which develops in the digestive tract 112, is generally believed to develop in a position below the inner wall surface (mucosa surface) 113 of the digestive tract 112 at a depth of about 1 mm or smaller. If the early-stage cancer cell population 152, which has not yet reached and penetrated a muscular layer of mucosa 160, can be found over a wide range with no missing cancer cell population, the number of conditions leading to an advanced cancer, which is a state in which the cancer cell population proliferates beyond the muscular layer of mucosa 160 and spreads to another organ, can be reduced.

As an attempt to grasp a lesion, such as the cancer cell population 152 as a representative example, in a living body the present inventors have imaged a cell morphology in the living body under a multiphoton laser microscope (FV1000MPE manufactured by Olympus Corporation). A multiphoton laser microscope is a fluorescence microscope using a multiphoton excitation process. A laboratory mouse was used as the living body.

FIG. 3 is a diagrammatic view showing that the inner wall of the digestive tract 112 is imaged under the multiphoton laser microscope. To irradiate the inner wall of the digestive tract 112, which is an imaging target, with laser light L, an objective lens 16 of the multiphoton laser microscope is so disposed as to face the inner wall surface 113 of the digestive tract 112, as shown in FIG. 3.

To primarily image the epithelial cells 121, the objective lens 16 is so disposed that the focal point of the objective lens 16 coincides with the inner wall surface (mucosa surface) 113. As a result, the epithelial cells 121 and other parts are imaged as shown in the section (a) of FIG. 3, which is a diagrammatic view taken along the line a-a in FIG. 3. On the other hand, to primarily image the glandular cells 131, the capillaries 132, and the connective tissue 133, the objective lens 16 is so disposed that the focal point of the objective lens 16 coincides with a position below the inner wall surface (mucosa surface) 113 at a depth of 10 µm or greater. As a result, the glandular cells 131, the capillaries 132, and the connective tissue 133 are imaged as shown in the section (b) of FIG. 3, which is a diagrammatic view taken along the line b-b in FIG. 3. Changing the position of the focal point of the objective lens 16 of the multiphoton laser microscope as described above allows the epithelial cells 121, the glandular cells 131, the capillaries 132, and the connective tissue 133 in the digestive tract 112 to be imaged.

To image a cell morphology in a living body under the multiphoton laser microscope, the present inventors stained the living body (laboratory mouse) in a chromatic color with a stain containing an edible dye before the imaging was performed. Using the stain allows selective staining of the epithelial cells 121, the glandular cells 131, the capillaries 132, and the connective tissue 133 of the digestive tract 112. An edible dye is a natural dye or an artificial dye that is allowed to be administered to a person (food coloring dye, for example).

The images shown in FIG. 4 show the epithelial cells 121, the glandular cells 131, and other parts stained with a stain containing curcumin and then imaged under the multiphoton laser microscope. The wavelength of the laser light was 780 nm, and the magnification of the objective lens was 10 times in the section (a) of FIGS. 4 and 25 times in the section (b) of FIG. 4. The images shown in FIG. 5 show the capillaries 132, the connective tissue 133, and other parts stained with a stain containing Acid Red (red #106) and then imaged under the multiphoton laser microscope. The wavelength of the laser light was 840 nm, and the magnification of the objective lens was 10 times in the section (a) of FIG. 5, 25 times in the section (b) of FIG. 5, and 75 times (optical magnification of 25 times and software zooming magnification of 3 times) in the section (c) of FIG. 5. The stain containing curcumin can be a curcumin solution (undiluted liquid 5%) diluted with a physiological saline solution at a ratio ranging from 1/5 to 1/5000, and the staining period ranges from about 2 to 5 minutes. FIG. 4 shows monochromatic images that are inherently color images, and the portions corresponding to the stained epithelium and gland can be displayed in a green fluorescent color, whereas the capillaries and the connective tissue can be displayed in non-fluorescent dark green. The fluorescent color is expressed by converting the color of the actual fluorescence into a visually recognizable color with the aid of image correction.

Sharp images of the cell groups can be obtained, as shown in FIGS. 4 and 5, by staining the cell groups in the living body with the stains.

To stain a living body with a stain, the present inventors have made a new attempt: That is, two types of stains were used to selectively stain the cell groups in at least two different chromatic colors in accordance with the type of cells in each cell group before the imaging was performed. Specifically, the living body was stained with the stain containing curcumin and the stain containing Acid Red. Selectively staining cell groups in the living body in at least two different chromatic colors with two types of stains in accordance with the type of cells is hereinafter referred to as "double staining."

The images shown in FIG. 6 show the inner wall of the digestive tract 112 double-stained with a stain containing curcumin and a stain containing Acid Red and then imaged under the multiphoton laser microscope. In FIG. 6, the section (a) shows an image of a healthy digestive tract 112, and the section (b) shows an image of the digestive tract 112 having the early-stage colorectal cancer cell population 152 formed therein. The magnification of the image shown in the section (a) is greater than the magnification of the image shown in the section (b) by a factor of 1.5.

The stain containing curcumin was a curcumin solution (5% undiluted liquid) diluted with a physiological saline solution at a ratio of 1/10. The stain containing Acid Red was an Acid Red solution (10 mg/mL of undiluted liquid) with no change. The staining period ranged from 2 to 5 minutes in both cases. Instead, the stain containing curcumin may be a curcumin solution (5% undiluted liquid) diluted with a physiological saline solution at a ratio ranging from 1/5 to 1/5000, and the stain containing Acid Red may be an Acid Red solution (10 mg/mL of undiluted liquid) with no change or having a concentration of 100% or diluted at a ratio of 1/1 to 1/1000.

Double-staining and then imaging the cell group in the living body allows a plurality of types of tissue, such as the epithelium, the gland, and the capillaries, or the connective tissue in the inner wall of the digestive tract 112 to be simultaneously checked in a single image, as shown in the section (a) of FIG. 6. FIG. 6 shows monochromatic images that are inherently color images, and the difference in the tendency of the staining performed by the stains causes the portions corresponding to the epithelium and the gland to be displayed in a green fluorescent color, and the capillaries and the connective tissue to be displayed in a pale red or near orange fluorescent color, whereby the portions corresponding to the epithelium and the gland are more clearly distinguished from the capillaries and the connective tissue, as compared with the single-stain staining. Since the fluorescent color achieved by the curcumin solution staining is displayed in green, and the fluorescent color achieved by the Acid Red solution staining is displayed in red, the actual fluorescence is converted into a visually recognizable color with the aid of image correction. Further, comparison of the shape and brightness of the cell group between the sections (a) and (b) allows checking whether the digestive tract 112 is healthy or a lesion, such as cancer, has developed in the digestive tract 112, as shown in the section (b) of FIG. 6.

The stains for double-staining are not limited to those described above and can be a stain containing curcumin and a stain containing FastGreen FCF. In this case, the stain containing curcumin may be a curcumin solution (5% undiluted liquid) diluted with a physiological saline solution at a ratio of 1/10, and the stain containing FastGreen FCF may be a FastGreen FCF solution (10 mg/mL of undiluted liquid) with no change. The staining period may range from 2 to 5 minutes in both cases. Instead, the stain containing curcumin may be a curcumin solution (5% undiluted liquid) diluted with a physiological saline solution at a ratio ranging from 1/5 to 1/5000, and the stain containing FastGreen FCF may be a FastGreen FCF solution (10 mg/mL of undiluted liquid) with no change or having a concentration of 100% or diluted at a ratio of 1/1 to 1/1000.

To stain a living body with a stain, the present inventors have used a stain that specifically stains a cancer cell surrounding cell group other than the cancer cells located around the cancer cell population 152 in a chromatic color to selectively stain the cell group in the living body and imaged the cancer cell surrounding cell group. Specifically, a stain containing RoseBengal was used to stain the living body.

The section (a) of FIG. 7 shows an image illustrating fluorescence emitted only from cancer cells imaged by using GFP, which is a green fluorescence protein. The section (b) of FIG. 7 shows an image of the inner wall of the digestive tract 112 stained with the stain containing RoseBengal and then imaged under the multiphoton laser microscope. The section (c) of FIG. 7 is the image shown in the section (a) and the image shown in the section (b) merged with each other and allows only the cancer cell surrounding cell group to be clearly identified because the actual image shown in the section (a) is displayed in the green fluorescent color and the actual image shown in the section (b) is displayed in the red fluorescent color.

Since the fluorescence from the cancer cell surrounding cell group, which is located around the cancer cell population 152 shown in the section (a) out of the cell groups in the living body, is obtained, as shown in the section (b) of FIG. 7, imaging the cell group around the cancer cell population 152 allows checking of whether cancer has developed in the digestive tract 112. Using the obtained image is effective in determining the range of treatment for preventing the cancer from developing again after the cancer cells are removed as well as the range over which the cancer cells are treated. For example, the patient can be treated in a safer manner by determining a treatment reference, for example, the cell group around the cancer cells shown in the section (b) of FIG. 7 is so treated that the cancer cells and the cell group around the cancer cells and over the half the length of the cell group from the cancer cells are removed.

The present inventors have still further attempted to image the cell morphology in the living body under the multiphoton laser microscope and overlap a plurality of captured images with each other to create a merged image.

FIG. 8 is a diagrammatic view showing that the inner wall of the digestive tract 112 is imaged over the entire circumference thereof under a multiphoton laser microscope 102. An imaging head 11 for radiating a laser light L is inserted along an inner wall surface 113 of the widened digestive tract 112, and the imaging head 11 can then be moved to image a plurality of imaging regions P, as shown in FIG. 8. In this process, the imaging can be so performed that imaging regions P1 and P2 adjacent to each other out of the plurality of imaging regions P partially have identical portions. Identical portions Ps, belonging to the adjacent imaging regions P1 and P2, are successively aligned with each other to create a merged image.

FIG. 9 is a merged image of the inner wall of the digestive tract 112 stained with the stain containing Acid Red. FIG. 10A is a merged image of the inner wall of the digestive tract 112 stained with the stain containing curcumin and the stain containing Acid Red. FIG. 10B shows an example of a stereoscopic image reconstructed from the panoramic image of the inner wall of the digestive tract 112.

Creating a merged image that is a plurality of overlapped images allows grasp of the cell morphology in the living body over a wide range with no missing part, as shown in FIGS. 9 and 10A. Still further, it is conceivable to create a panoramic image of the inner wall of the digestive tract 112 by moving the imaging head 11 along the inner circumference of the digestive tract 112 and performing imaging with the imaging head 11 revolving over 360°, as shown in FIG. 8. Moreover, stereoscopic reconstruction of the panoramic image into a tunnel-shaped image allows the position (coordinates) where a lesion is present in the digestive tract 112 to be readily visualized and grasped, as shown in FIG. 10B. The imaging described above allows exhaustive detection of a lesion in the living body.

That is, the primary configuration of the present invention allows non-coincidental wide-range exhaustive detection of a microscopic lesion, such as ultra-early-stage cancer (diameter ranging from 0.2 mm to 1 mm) the presence of which cannot be detected with an existing endoscope because the size of the lesion is too small.

First Embodiment

Embodiments of the present invention will be described below in detail with reference to the drawings.

The embodiments described below are each a preferable specific example of the present invention. Numerical values, shapes, materials, constituent elements, the positions where the constituent elements are arranged, the form in accordance with which the constituent elements are connected to each other, steps, the order of the steps, and other factors are presented by way of example and are not intended to limit the present invention. The present invention is specified by the claims. Therefore, out of the constituent elements in the following embodiments, a constituent element that is not described in any independent claim will be described as an arbitrary constituent element. Further, in the drawings, substantially the same configurations have the same reference character, and a duplicated description of such configurations will be omitted or simplified.

[1. Configuration of Laser Endoscope Device]

A laser endoscope device according to the present embodiment is a device capable of imaging a lesion having developed in the digestive tract, the respiratory system, the renal/urinary system, the utero-ovarian reproductive system, the cerebrospinal nervous system, and other body sites over a wide range with no missing part. The laser endoscope device can not only perform the imaging but treat the lesion having developed in the living body. The present embodiment will be described with reference to the digestive tract 112 in the living body.

[1.1 Configuration for Imaging Preparation]

The configuration of the laser endoscope device for imaging preparation will first be described.

Since the inner wall of the actual digestive tract 112 has irregularities, it is desirable to widen the digestive tract 112 to make the digestive tract 112 imageable before the inner wall is imaged by using the laser endoscope device. Further, to obtain a sharp image by using the laser endoscope device, it is desirable to stain a cell group in the inner wall of the digestive tract 112. To this end, the laser endoscope device according to the present embodiment includes an insertion tube that widens the digestive tract 112 and a stain supplier that supplies a stain to stain the cell group in the inner wall of the digestive tract 112.

The section (a) of FIG. 11 shows a state after an insertion tube 20 has been inserted into the digestive tract 112.

The insertion tube 20 has a supply port 42, through which fluid is supplied, and a recovery port 43, through which the supplied fluid is recovered, as shown in the section (a) of FIG. 11. The insertion tube 20 is further provided with a first balloon 21 and a second balloon 22. The first balloon 21 and the second balloon 22 bulge and shrink when the fluid (gas or liquid) is injected into and discharged from the balloons 21 and 22. The first balloon 21 is provided in a position shifted from the supply port 42 toward the front end of the insertion tube 20, and the second balloon 22 is provided in a position shifted from the recovery port 43 toward the rear side of the insertion tube 20 (opposite the front end). Causing the first balloon 21 and the second balloon 22 to bulge in the digestive tract 112 creates a closed space S sandwiched between the first balloon 21 and the second balloon 22 in the insertion tube 20.

The section (b) of FIG. 11 and FIG. 12 show an example of a stain supplier 40 for supplying a stain 45. The stain 45 is supplied into the space S, for example, from the stain supplier 40, which stores the stain 45, via the insertion tube 20 and the supply port 42, as shown in FIG. 12. The stain 45 may, for example, be a single stain formed of the stain containing a curcumin-based compound or the stain containing Acid Red. It is, however, desirable to use two stains, the stain containing a curcumin-based compound and the stain containing Acid Red. Staining the cell group in the living body in two colors by using the two stains 45 allows a sharper image to be obtained. Curcumin-based compounds include not only curcumin, of course, but highly water-soluble curcuminoid (mixture of several types of curcumin derivatives).

The stain 45 may instead be a single stain containing both a curcumin-based compound and Acid Red. Still instead, the stain 45 may be a single stain containing both a curcumin-based compound and FastGreen FCF or two stains formed of the stain containing a curcumin-based compound and the stain containing FastGreen FCF. The stain 45 is not necessarily formed of two stains and may be formed of a single-color stain. For example, the stain 45 may be a stain containing RoseBengal. Before the staining, the interior of the digestive tract 112 may be cleaned and the mucus in the digestive tract 112 may be removed via the supply port 42 and the recovery port 43.

Thereafter, gas is, for example, supplied via the supply port 42 to cause the digestive tract 112 to bulge, so that the inner wall of the digestive tract 112 is stretched and planarized, as shown in the section (a) of FIG. 13. It is desirable that the irregularities of the planarized inner wall surface 113 have a height difference, for example, smaller than or equal to 0.2 mm. The living body is now ready to be imaged with the laser endoscope device.

Planarizing the inner wall of the digestive tract 112 allows precise grasp of the states of the inner wall surface 113 and the cell group in a position below the inner wall surface 113 at a predetermined depth. Further, since the inner wall of the digestive tract 112 is imaged with the laser light L directly applied thereto instead of imaging via a bag-shaped element that bulges the digestive tract 112, the inner wall surface 113 and other parts can be precisely grasped.

The medium that causes the digestive tract 112 to bulge is not limited to gas and can instead be distilled water, a physiological saline solution, or any other liquid. In the case where liquid is used, the liquid needs to transmit the laser light to be used and light having a certain wavelength. Further, in the case where the medium is liquid, it is desirable to increase the concentration of the stain as compared with the case where the medium is gas. To adjust the inner pressure in the digestive tract 112, a pressure sensor may be provided in a position between the first balloon 21 and the second balloon. The pressure sensor is preferably formed of a plurality of pressure sensors provided at equal intervals.

[1.2 Basic Configuration of Laser Endoscope Device]

The basic configuration of a laser endoscope device 1 according to the first embodiment will next be described with reference to the section (b) of FIG. 13 and FIGS. 14 and 15.

The section (b) of FIG. 13 is a schematic view showing a front-end-side end portion of an endoscope 2 of the laser endoscope device 1 in FIG. 15. FIG. 14 is a schematic view showing the entire endoscope 2. FIG. 15 is a block diagram showing the control configuration of the laser endoscope device 1.

The laser endoscope device 1 includes an imaging unit 10, which includes the endoscope 2, a control unit 50, and an image processing unit 70, as shown in FIG. 15. The laser endoscope device 1 further includes a laser oscillator 60 and an optical part 65.

The laser light L emitted from the laser oscillator 60 is reflected off a dichroic mirror 66, which is the optical part 65, further reflected off a mirror 19 in the endoscope 2, and applied to the living body. Living cells irradiated with the laser light L produce fluorescence, and the fluorescence is reflected off the mirror 19, passes through the dichroic mirror 66, and is detected with a photodetector 35. The light detected with the photodetector 35 is converted into an electric signal, and the image processing unit 70 forms an image according to the electric signal. Since the color of the fluorescence changes in accordance with the stain, the photodetector 35 is formed of a plurality of photodetectors, and a color separation optical filter is disposed in a position on the upstream side of the photodetector 35 for color separation.

The laser oscillator 60 to be used is configured to have a pulse width ranging from several tens to several hundreds of femtosecond and a pulse frequency ranging from several tens to several hundreds of megahertz. The laser light L in the present embodiment is two-photon laser light, which is a kind of multiphoton laser light, and the laser oscillator 60 uses, for example, a pulse laser capable of emitting light having a wavelength of 800 nm and a power of 3.2 W at the maximum. In the imaging operation, the laser outputs laser light having a power ranging from 0.16 to 0.32 W. Setting the wavelength at 800 nm or longer can prevent photons that belong to the ultraviolet region (wavelength shorter than 400 nm) from being produced in the half-wavelength light produced in the multiphoton excitation process. The laser oscillator 60 can adjust the intensity of the laser light L.

The dichroic mirror 66, which is the optical part 65, reflects light having the same wavelength as that of the laser light L and transmits light having the other wavelengths. The laser light L emitted from the laser oscillator 60 is therefore reflected off the dichroic mirror 66 toward the mirror 19. On the other hand, the fluorescence produced in the living cells is reflected off the mirror 19, then passes through the dichroic mirror 66, and reaches the photodetector 35. The optical part 65 can instead be formed, for example, of a prism or a 4/λ plate.

The imaging unit 10 includes the endoscope 2 and the photodetector 35 and images the cell morphology in the living body with the laser light L applied to the interior of the living body.

The photodetector 35 detects the fluorescence produced when the laser light L is applied and converts the fluorescence into an electric signal according to the intensity of the fluorescence. The photodetector 35 can, for example, be a photomultiplier or a CCD semiconductor image sensor.

The endoscope 2 includes an inner tube 12 and an outer tube 13, which surrounds part of the outer surface of the inner tube 12, as shown in FIG. 14. The inner tube 12 and part of the outer tube 13 are inserted into the living body. The inner tube 12 has a length, for example, of 50 mm and an outer diameter ranging from, for example, 3 to 10 mm. A linear-motion actuator is attached to the inner tube 12, and the inner tube 12 is movable relative to the outer tube 13 in the axial direction X by about 25 mm. An ultrasonic motor is further attached to the inner tube 12, and the inner tube 12 is revolvable relative to the outer tube 13 over 360°. The action of the inner tube 12 in the axial direction X or the revolutional direction R is controlled by the control unit 50.

The imaging head 11 is provided at a front-end-side end portion of the inner tube 12 of the endoscope 2. The imaging head 11 is inserted along with the inner tube 12 into the living body in such a way that the imaging head 11 passes by the insertion tube 20, as shown in the section (b) of FIG. 13. The imaging head 11 is so controlled as to move in the living body based on the actions in the axial direction X and the revolutional direction R of the inner tube 12.

The imaging head 11 includes the objective lens 16, a focal point changer 18, a spacer 17, and the mirror 19.

The mirror 19 is a part that redirects the laser light L outputted from the laser oscillator 60 toward the objective lens 16 or redirects the fluorescence emitted from the living cells toward the photodetector 35, as described above.

The objective lens 16 is so provided as to face the inner wall surface 113 of the living body. The objective lens 16 has, for example, a diameter of 10 mm, a magnification of 10 times, a resolution of 5 µm, and an imaging field of view of 3 mm×3 mm. The objective lens 16 instead has a diameter of 12 mm, a magnification of 40 times, a resolution of 10 µm, and a field of view of 7.5 mm×7.5 mm. The wider the imaging field of view, the better. The objective lens 16 may still instead be so configured that part of a lens having either of the diameters described above is cut or the diameter of the objective lens 16 is reduced to a value ranging from 3 mm to 5 mm so that the objective lens is readily inserted into the living body with the same resolution maintained.

The focal point changer 18 is, for example, a piezoelectric actuator or an electromagnetic actuator and moves the objective lens 16 in the optical axis direction to change the position of the focal point of the objective lens 16. The focal point changer 18 operates under the control of the control unit 50 and can adjust the focal point over a depth range from 0 to 1000 µm below the inner wall surface (mucosa surface) 113. Changing the position of the focal point allows imaging of the state of the living body at a predetermined depth below the cell surface of the digestive tract 112. In a case where the multiphoton laser light is replaced with confocal laser light, the focal point below the inner wall surface (mucosa surface) 113 may be adjusted over a depth range from 0 to 75 µm.

The spacer 17 has, for example, an annular shape and is provided around the space between the objective lens 16 and the inner wall surface 113. The spacer 17 is a part not only for preventing the objective lens 16 from coming into contact with the inner wall of the living body but for maintaining a fixed distance between the objective lens 16 and the inner wall surface 113. The distance between the objective lens 16 and the inner wall surface (mucosa surface) 113 is set at an appropriate value, for example, a value greater than or equal to 1 mm but smaller than or equal to 10 mm by exchanging the spacer 17 to another before the imaging starts or adding a distance changeable mechanism using an actuator or any other device. The control unit 50 controls the movement of the imaging head 11 (inner tube 12) with the spacer 17 being in contact with the inner wall surface 113 and maintains the fixed distance from the objective lens 16 to the inner wall surface 113.

The control unit 50 is formed, for example, of a CPU, a ROM, and a RAM. The control unit 50 controls the action of the imaging head 11 via the inner tube 12. Specifically, the control unit 50 controls the movement of the imaging head 11 not only in the circumferential direction along the inner circumference of the inner wall of the digestive tract 112 but in the tract longitudinal direction of the digestive tract 112 (along axis of digestive tract). The control unit 50 further changes the position of the objective lens 16 in the optical axis direction by controlling the action of the focal point changer 18 to control the position where the focus is achieved in the living body. The control unit 50 can further adjust the laser output by controlling the laser oscillator 60.

The image processing unit 70 stores the converted electric signal (fluorescence intensity) from the photodetector 35 and the coordinate position of the imaging unit 10 sent from the control unit 50 with the electric signal and the coordinate position related to each other and processes the data on the fluorescence intensity and the coordinate position to generate a digital image. The generated digital image is, for example, displayed on a monitor, printed out, or recorded on a storage device. The coordinate position of the imaging unit 10 may be expressed, for example, in the form of the distance from a reference location on the patient (throat or anus, for example) and the angle of revolution of the imaging head 11.

In the laser endoscope device 1 according to the present embodiment, the control unit 50 controls the movement of the imaging head 11 in such a way that the imaging head 11 scans the inner wall surface 113 of the living body with the fixed distance from the imaging head 11 to the inner wall surface 113 maintained. The imaging unit 10 images a plurality of imaging regions P, which are imaged as the imaging head 11 moves, in such a way that adjacent imaging regions P1 and P2 partially overlap with each other, as shown in FIG. 16. The image processing unit 70 successively overlaps the region Pa, where the adjacent imaging regions P1 and P2 overlap with each other, with another region Pa to generate a merged image. The cell morphology in the living body can thus be imaged over a wide range with no missing part.

Further, using the laser endoscope device 1 allows generation of a panoramic image. For example, the control unit 50 controls the imaging head 11 in such a way that the imaging head 11 moves over 360° along the inner circumference of the digestive tract 112 (or orbits around axis of digestive tract 112), as shown in FIG. 16. The imaging unit 10 then images a plurality of imaging regions P, which are imaged as the imaging head 11 moves, in such a way that adjacent imaging regions P1 and P2 have identical portions in the circumferential direction. The image processing unit 70 successively causes the identical portions Pa, belonging to the adjacent imaging regions P1 and P2, to be aligned with each other to generate a panoramic image. The state of the inner wall of the digestive tract 112 can thus be exhaustively grasped.

Further, using the laser endoscope device 1 allows generation of images along the tract longitudinal direction of the digestive tract 112. For example, after the inner circumference of the digestive tract 112 is imaged over 360°, the control unit 50 moves the imaging head 11 by a predetermined distance along the tract longitudinal direction of the digestive tract 112, and the imaging unit 10 performs imaging in such a way that an imaging region P11 to be imaged after the movement and the imaging region P1 adjacent to the imaging region P11 in the tract longitudinal direction have identical portions. The image processing unit 70 then successively causes identical portions Pb, belonging to the two imaging regions P1 and P11 to be aligned with each other. The imaging unit 10 then performs the imaging over 360° along the inner circumference of the digestive tract 112, and the image processing unit 70 overlaps the regions that overlap with each other in the circumferential and tract longitudinal directions to generate a panoramic image extending in the tract longitudinal direction. The state of the inner wall of the digestive tract 112 can thus be exhaustively grasped also in the tract longitudinal direction.

Using the laser endoscope device 1 further allows generation of a stereoscopic image of the living body. For example, the control unit 50 controls the operation of the focal point changer 18 of the imaging head 11 to change the position of the focal point of the objective lens 16, and the imaging unit 10 images a plurality of imaging regions at different depths as the position of the focal point is changed. The image processing unit 70 then places the plurality of images obtained by the imaging in correspondence with the position of the focal point to generate a stereoscopic image of the cell morphology in the living body. The cell morphology in the living body over a predetermined depth range can thus be imaged as well as the inner wall surface 113 of the living body.

[2.1 Action 1 of Laser Endoscope Device]

The action of the laser endoscope device 1 in the case where the cell morphology in the digestive tract 112 is imaged will next be described.

Since the inner wall of the digestive tract 112 typically has irregularities, the inner wall of the digestive tract 112 is planarized, as shown in the section (a) of FIG. 17A.

The insertion tube 20 is first inserted into the digestive tract 112, as shown in the section (b) of FIG. 17A.

Thereafter, at the front end of the insertion tube 20, the first balloon 21 is so bulged as to come into contact with the inner wall surface 113 of the digestive tract 112, as shown in the section (c) of FIG. 17A. To improve airtightness achieved by the first balloon 21, the first balloon 21 is formed of three balloons.

The second balloon 22, which is located on the rear side of the insertion tube 20, is then so bulged as to come into contact with the inner wall surface 113 of the digestive tract 112, as shown in the section (d) of FIG. 17A. The second balloon 22 is also formed of three balloons. The action described above forms the closed space S between the first balloon 21 and the second balloon 22. Air is then blown out of the supply port 42 into the closed space S to bulge the interior of the digestive tract 112. Wrinkles and other irregularities present on the inner wall of the digestive tract 112 are thus stretched and planarized. The step of planarizing the inner wall may be carried out after a staining step, which will be descried later.

A cleaning liquid is then supplied into the closed space S via the supply port 42, as shown in the section (e) of FIG. 17B. The inner wall surface 113 of the digestive tract 112 is thus cleaned. The cleaning liquid is then sucked and recovered via the recovery port 43.

A pronase liquid is then supplied via the supply port 42 into the closed space S, as shown in the section (f) of FIG. 17B. Excess of the mucus having adhered to the inner wall surface 113 of the digestive tract 112 is thus removed. The pronase liquid is then sucked and recovered via the recovery port 43.

A stain A (stain containing a curcumin-based compound, for example) is then supplied via the supply port 42 into the closed space S to fill the closed space S with the stain A, as shown in the section (g) of FIG. 17B. The stain A is then left for 2 to 5 minutes, and the space S is then cleaned with the cleaning liquid. A predetermined cell group in the inner wall of the digestive tract 112 is thus stained with the stain A. The predetermined cell group refers to a plurality of cells contained in the epithelial cells 121, the glandular cells 131, the capillaries 132, or the connective tissue 133.

A stain B (stain containing Acid Red, for example) is then supplied via the supply port 42 into the closed space S to fill the closed space S with the stain B, as shown in the section (h) of FIG. 17B. The stain B is then left for 2 to 5 minutes, and the space S is then cleaned with the cleaning liquid. The predetermined cell group in the inner wall of the digestive tract 112 is thus stained with the stain B, so that the inner wall of the digestive tract 112 is double stained. As described above, employing the method for filling the space S with the stain A or B allows the inner wall of the digestive tract 112 to be double stained with only a small amount of staining unevenness.

The endoscope 2 is then inserted into the closed space S, as shown in the section (i) of FIG. 17C. The imaging head 11 provided at the front end of the endoscope 2 performs the imaging with the fixed distance between the inner wall surface 113 and the objective lens 16 maintained by changing the position of the focal point of the objective lens 16 to the depth of 0 µm, 30 µm, 60 µm, 90 µm, 120 µm, and 150 µm below the inner wall surface (mucosa surface) 113. The position corresponding to the depth of 0 µm can be determined with the aid of an autofocus function with which the endoscope 2 is equipped. In the case where confocal laser light is used in place of the multiphoton laser light, the imaging is performed by changing the position of the focal point of the objective lens 16 to the depth of 0 µm, 25 µm, 50 µm, and 75 µm below the inner wall surface (mucosa surface) 113. The depth intervals that change as described above are presented only by way of example, and finer or coarser intervals may be employed.

Imaging is then performed with the imaging head 11 caused to revolve over 360° along the inner wall surface 113, as shown in the section (j) of FIG. 17C. In this process, the imaging is so performed that the imaging regions P1 and P2 adjacent to each other in the circumferential direction have identical portions. The imaging of the identical portions allows acquisition of a first panoramic image. When the imaging over 360° along the inner circumference is completed, the imaging head 11 is moved by a predetermined distance along the tract longitudinal direction of the digestive tract 112. The imaging head 11 is then caused to revolve over 360° again to acquire a second panoramic image. The first and second panoramic images are so imaged that the imaging regions P1 and P11, which are adjacent to each other in the tract longitudinal direction of the insertion tube 20, have identical portions, and the identical portions in the circumferential and longitudinal directions of the digestive tract are accurately aligned with each other with the aid of image processing into a seamless merged image. The actions described above are repeated multiple times (5 times in the present embodiment).

When the imaging described above is temporarily completed, the endoscope 2 including the imaging head 11 is moved to a point behind the second balloon 22, as shown in the section (k) of FIG. 17C.

Thereafter, to change the imaging region and perform the imaging again, the first balloon 21 is caused to shrink, as shown in the section (1) of FIG. 17D. The insertion tube 20 is then pulled rearward with the position of the second balloon 22 maintained, as shown in the section (m) of FIG. 17D. The first balloon 21 is then caused to bulge, as shown in the section (n) of FIG. 17D. The second balloon 22 is caused to shrink, as shown in the section (o) of FIG. 17E, and the insertion tube 20 is then pulled rearward with the position of the first balloon 21 maintained, as shown in the section (p) of FIG. 17E. The second balloon 22 is then caused to bulge, as shown in the section (q) of FIG. 17E. Another closed space S1 adjacent to the previously formed closed space S in the tract longitudinal direction is thus formed. The actions shown in the section (d) of FIG. 17A to the section (k) of FIG. 17C are performed again for the closed space S1.

Repeating the actions described above allows the imaging to be performed over the length, for example, of 300 mm in the tract longitudinal direction. In a case where the digestive tract 112 is the large intestine, the overall length of the large intestine may be imaged in four separate sets of imaging operation.

The action of the laser endoscope device 1 described above allows exhaustive, efficient imaging of the state of the inner wall of the digestive tract 112 in the inner circumferential direction and the tract longitudinal direction of the digestive tract 112.

[2.2 Action 2 of Laser Endoscope Device]

The laser endoscope device 1 is further configured to efficiently detect a lesion, such as cancer cells, in the depth direction.

To this end, the control unit 50 has the following two focal point changeable modes (see FIG. 15). Specifically, the control unit 50 has a first focal point changeable mode 51, in which the focal point position is changed by a first interval, and a second focal point changeable mode 52, in which the focal point position is changed by a second interval, which is smaller than the first interval. The first focal point changeable mode 51 is a mode for changing the focal point position in such a way that the laser light L is focused, for example, in the positions below the inner wall surface (mucosa surface) 113 of the living body at the depth of 0 μm, 30 μm, 60 μm, 90 μm, and 120 μm. The second focal point changeable mode 52 is a mode for changing the focal point position by a narrower interval, for example, a 5-μm interval. The intervals are variable and can be changed by rewriting a program.

To quickly evaluate whether or not a lesion is present, the control unit 50 stores a reference image of a lesion-free healthy cell for each internal organ. Since the reference image of a healthy cells varies in accordance with the type of laser light with which the cell is irradiated (multiphoton laser light or confocal laser light) and the depth from the surface of the cell membrane of an organ and further varies, in the case where a stain is used, in accordance with the type of the stain, it is preferable to prepare in advance reference images according to imaging conditions.

FIG. 18 is a flowchart showing an example of the action of the laser endoscope device 1. The control unit 50 first causes the imaging unit 10 to perform imaging in the depth direction in the first focal point changeable mode 51 over a certain depth range, in which the imaging is performed at the coarse imaging intervals (S11). In this process, the magnification is set at a small value (lower than or equal to 10 times, for example), and a trial image is acquired for evaluation. The image to be evaluated may be an image captured only at a fixed depth in non-depth-changing imaging or may be an image of the mucosa surface.

The control unit 50 then compares the image obtained in the first focal point changeable mode 51 with the reference image of healthy cells stored in advance in terms of at least one of the shape and the brightness and evaluates suspicion of a lesion (S12). In a case where there is no suspicion of a lesion, the examination is terminated (S13).

In a case where the image obtained by the imaging contains a portion suspicious of a lesion, the control unit 50 causes the imaging unit 10 to perform imaging in the second focal point changeable mode 52 in the vicinity of the focal point position where the image containing the portion suspicious of a lesion was captured (S14). In this process, the magnification is set at a large value (40 times, for example). Also in this case, the image to be evaluated may be an image captured only at a fixed depth in non-depth-changing imaging or may be an image of the surface as along as the image allows diagnosis of the examination target.

The control unit 50 then compares the image obtained in the first focal point changeable mode 51 with the reference image of healthy cells stored in advance in terms of at least one of the shape and the brightness and evaluates suspicion of a lesion (S15). In a case where there is no suspicion of a lesion, the examination is terminated (S16).

In a case where the image obtained by the imaging unit 10 contains cells having a lesion, the control unit 50 increases the power of the laser light L as compared with the power in the imaging and applies the laser light L having the increased power to the cells having a lesion to remove (evaporate) the cells having a lesion (S17). Although not shown, after the cells having a lesion are removed, it is preferable to image the same location again and check again if the cells having a lesion are still present or not. The power of the laser light used to remove the cells is 10 to 20 times the power in the imaging or ranges from 2 to 3 W.

In the evaluation described above, the comparison in terms of shape, brightness, or any other factor may be automatically made with a computer. In a case where the evaluation made by the computer shows a location suspicious of a lesion, the result of the evaluation is preferably checked by a medical doctor.

The tomographic imaging described above allows exhaustive imaging with the imaging period shortened. Further, a cell having a lesion can be reliably removed in an early stage of the lesion. In the removal treatment described above, the diagnosis and removal may be performed before the shift of the imaging space S described with reference to FIGS. 17A to 17E, or the lesion may be removed after the imaging of the target organ and in another opportunity by forming a series of imaging spaces S based on the coordinates of the resultant images. The timing when the lesion is removed can be determined based, for example, on the physical strength of the patient, the condition of the diseased site, and the performance of the laser endoscope device 1.

(Variation 1)

FIG. 19 is a diagrammatic view showing an example in which a laser endoscope device 1 according to Variation 1 of the first embodiment is used to generate a panoramic image.

The control unit 50 in the Variation 1 controls the imaging head 11 attached to an arm 15 in such a way that the imaging head 11 helically revolves around the axis of the digestive tract 112. The imaging unit 10 images a plurality of imaging regions P to be imaged as the imaging head 11 revolves in such a way that imaging regions P1 and P2 adjacent to each other partially overlap with each other in the direction of revolution R. The image processing unit 70 successively overlaps a region Pa, where the adjacent imaging regions P1 and P2 overlap with each other, with another region Pa to generate a panoramic image. The state of the inner wall of the digestive tract 112 can thus be exhaustively imaged.

(Variation 2)

FIG. 20 is a diagrammatic view showing an example in which a laser endoscope device 1 according to Variation 2 of the first embodiment is used to image the interior of a living body.

In Variation 2, to maintain a fixed distance between the inner wall surface 113 of the digestive tract 112 and the objective lens 16, a pair of wheels 17a are attached to the arm 15 on the front end side of the endoscope 2 in place of the spacer 17. To move the imaging head 11 in the inner circumferential direction, rolling the pair of wheels 17a with the wheels 17a being in contact with the inner wall surface 113 allows the objective lens 16 to be moved with a fixed distance from the objective lens 16 to the inner wall surface 113 maintained. As a result, an imaging target, such as the epithelial cells 121, the glandular cells 131, the capillaries 132, and the connective tissue 133, can be precisely brought into focus.

(Variation 3)

FIG. 21 is a diagrammatic view showing an example in which a laser endoscope device 1 according to Variation 3 of the first embodiment is used to image the interior of a living body.

In Variation 3, a pressing member 23 is provided at the rear of the imaging head 11 (side opposite the side via which the imaging head 11 radiates the laser light L), Fluid is introduced into the pressing member 23 so that the pressing member bulges, and the pressing member 23 presses the inner wall on the side opposite the imaging region, whereby the spacer 17 is in contact with the inner wall of the imaging region. The fixed distance between the objective lens 16 and the inner wall surface 113 can thus be maintained, whereby an imaging target can be precisely brought into focus.

(Variation 4)

FIG. 22 is a diagrammatic view showing an example in which a laser endoscope device 1 according to Variation 4 of the first embodiment is used to image the interior of a living body.

In Variation 4, a support roller 24 is provided at the rear of the imaging head 11 in place of the pressing member 23 shown in Variation 3. An extension mechanism 25 is then used to press the support roller 24 against the inner wall on the side opposite the imaging region to cause the spacer 17 to be in contact with the inner wall of the imaging region. The fixed distance between the objective lens 16 and the inner wall surface 113 can thus be maintained, whereby an imaging target can be precisely brought into focus.

(Variation 5)

FIG. 23 is a diagrammatic view showing an example in which a laser endoscope device 1 according to Variation 5 of the first embodiment is used to image the interior of a living body.

In Variation 5, a sliding member 26 is provided at the rear of the imaging head 11 in place of the support roller 24 shown in Variation 4. The extension mechanism 25 is then used to press the sliding member 26 against the inner wall on the side opposite the imaging region to cause the spacer 17 to be in contact with the inner wall of the imaging region. The fixed distance between the objective lens 16 and the inner wall surface 113 can thus be maintained, whereby an imaging target can be precisely brought into focus.

(Variation 6)

FIG. 24 is a diagrammatic view showing an example in which a laser endoscope device 1 according to Variation 6 of the first embodiment is used to image the interior of a living body.

In Variation 6, the imaging head 11 is supported by a joint mechanism 27, which flexibly moves, as shown in the section (a) of FIG. 24. Further, another joint mechanism 28 is provided at the rear of the imaging head 11 and supports the imaging head 11. According to the structure described above, protruding or recessed sites 113a, such as colorectal semilunar folds present in the digestive tract 112, can be imaged, as shown in the section (b) of FIG. 24. Further, using the autofocus function allows the fixed distance between the objective lens 16 and the inner wall surface 113 to be maintained.

(Variation 7)

FIG. 25 is a diagrammatic view showing an example in which a laser endoscope device 1 according to Variation 7 of the first embodiment is used to image the interior of a living body.

In Variation 7, the front end of the endoscope 2 is inserted into the first balloon 21, and the imaging head 11 is supported by a joint mechanism 27, which is provided in a halfway position on the inner tube 12 of the endoscope 2 (between first balloon 21 and second balloon 22). As a result, the joint mechanism 28 shown in Variation 6 is not necessary, whereby the structure of the endoscope 2 can be simplified as compared with the structure in Variation 6.

(Variation 8)

FIG. 26 is a diagrammatic view showing an example in which a laser endoscope device 1 according to Variation 8 of the first embodiment is used to image the interior of a living body.

In Variation 8, the imaging head 11 is provided with a gyro sensor 29. Information on the position and attitude of the imaging head 11 in the imaging operation can therefore be acquired. Further, captured image data can be displayed in a 3D form. Moreover, according to the structure described above, after the coarse-interval imaging is performed by using the first focal point changeable mode 51 described above, the imaging head 11 can quickly and accurately return to the portion suspicious of a lesion and can perform the imaging in the second focal point changeable mode 52, in which the imaging is performed at the fine imaging intervals. A GPS function may be added in place of the gyro sensor 29.

Further, in Variation 8, the inner tube 12 of the endoscope 2 is provided with a pressure sensor 30. Measuring the pressure in the closed space S with the pressure sensor 30 and feeding the measured pressure back allows appropriate adjustment of the pressure in the space S.

(Variation 9)

FIG. 27 is a diagrammatic view showing an example in which a laser endoscope device 1 according to Variation 9 of the first embodiment is used to image the interior of a living body.

In Variation 9, the imaging head 11 is provided with an extendable/shrinkable spacer 31 for adjusting the distance between the objective lens 16 and the inner wall surface 113. The section (a) of FIG. 27 shows a state in which the extendable/shrinkable spacer 31 is extended, and the section (b) of FIG. 27 shows a state in which the extendable/shrinkable spacer 31 is shrunk. The expansion and shrinkage of the extendable/shrinkable spacer 31 allows precise adjustment of the distance between the objective lens 16 and the inner wall surface 113. The extendable/shrinkable spacer 31 can be formed, for example, of an actuator.

(Variation 10)

FIG. 28 is a diagrammatic view showing an example in which a laser endoscope device 1 according to Variation 10 of the first embodiment is used to stain the interior of a living body.

In Variation 10, the insertion tube 20 is provided with a plurality of discharge ports 42a. Spraying a stain via the discharge ports 42a toward the inner wall so that the stain is applied onto the inner wall allows the inner wall to be stained. As a result, the amount of the stain to be used can be reduced as compared with the method in which the space S is filled with the stain. Even a stain using a dye that a living body tolerates by a small amount can therefore be used with no anxiety.

(Variation 11)

FIG. 29 is a diagrammatic view showing an example in which a laser endoscope device 1 according to Variation 11 of the first embodiment is used to image the interior of a living body.

In Variation 11, the gap between the pair of wheels 17a of the imaging head 11 shown in Variation 2 is increased so that an actuator or any other component that is not shown can move the mirror 19 and the objective lens 16 in the axial direction X of the endoscope 2. As a result, the interior of the living body can be imaged without unnecessarily long movement of the inner tube 12 of the endoscope 2.

(Variation 12)

FIGS. 30 and 31 are diagrammatic views showing an example in which a laser endoscope device 1 according to Variation 1 of the first embodiment is used to image the interior of a living body.

In Variation 12, the gap between the pair of wheels 17a of the imaging head 11 shown in Variation 2 is increased so that a plurality of (in the present variation, 5 sets of) mirrors 19 and objective lenses 16 are provided between the pair of wheels 17a. The imaging head 11 is so configured that the region between the first balloon 21 and the second balloon 22 can be imaged in a single 360°-revolution action, as shown in the sections (a) and (b) of FIG. 31. The interior of the living body can therefore be efficiently imaged.

In the embodiment described above, the endoscope 2, the insertion tube 20, the inner tube 12, the outer tube 13, and other components are each drawn in a linear shape. To allow the components described above to be so smoothly inserted as to follow the shape of, for example, the large intestine, it is preferable that the endoscope 2, the insertion tube 20, the inner tube 12, the outer tube 13, and other components are each flexible, and that an optical fiber or any other component is used as a laser light guide. Further, to allow the arm 15 or any other component of the imaging head 11 to have an L-letter-shaped structure or to have a linear shape so that the imaging head 11 can be accommodated in the inner tube 12, the imaging head 11 or any other component only needs to have an appropriate joint structure and a structure that fixes the arm 15 or any other component in the L-letter shape or any other shape, for example, with a wire.

The endoscope 2, the insertion tube 20, the arm 15, the spacer 17, the balloons 21 and 22, and other components are each made of a metal, resin, or rubber material. Since these components directly come into contact with a living organ, such as the large intestine and the stomach, the surface of each of the components is processed with extreme care and finished with extreme precision.

(Finding 2 on which Present Invention is Based)

The finding 2, on which the present invention is based, and a primary configuration of the invention associated with the finding 2 will next be described.

The finding 2 will be described with reference to a case where a cell morphology in a living body is imaged under the multiphoton laser microscope (FV1000MPE manufactured by Olympus Corporation) and a plurality of captured images are overlapped with each other to create a panoramic image. A laboratory mouse was used as the living body.

FIG. 32A is a diagrammatic view showing that the inner wall of the digestive tract 112 is imaged over the entire circumference thereof under the multiphoton laser microscope 102. The method for creating a panoramic image is roughly the same as the method for creating the image shown in FIG. 10A, which is related to the finding 1. That is, the imaging head 11 performs imaging while moving along the inner circumference of the digestive tract 112 and revolving over 360°, and the resultant images are merged with one another to obtain a panoramic image.

FIG. 32B shows a panoramic image illustrating the cell morphology in a position below the inner wall surface (mucosa surface) 113 at a depth of 50 µm. As the slain for staining the cell group, both the stain containing curcumin and the stain containing Acid Red (red #106) were used. FIG. 32B indicates that a plurality of crypts 138 (or glands 130) are arranged at roughly regular intervals.

Further, in FIG. 32B, the imaging regions P are arranged in correspondence with the direction of the hour hand of a timepiece shown in FIG. 32A, and a solitary lymphatic nodule, in which a plurality of lymphocytes gather, is formed in the 8-o'clock direction. The solitary lymphatic nodule is not at present as bad as a lesion, such as cancer, but FIG. 32B shows that the crypts 138 in the glands 130 disappear in the region where the solitary lymphatic nodule is formed. In view of the fact described above, the present inventors have assumed that the region where the solitary lymphatic nodule is formed is used as a coordinate mark in the panoramic image, and that when a lesion is found, the position of the lesion can be identified by the mark. The present inventors have further assumed that even if no solitary lymphatic nodule is present, the position where a lesion is present can be clearly identified with respect to a predetermined position in the panoramic image. An embodiment based on the finding 2 will be described below.

Second Embodiment

The configuration of a laser endoscope device 1A according to a second embodiment will be described with reference to FIG. 33. FIG. 33 shows an endoscope 2 of the laser endoscope device 1A.

The endoscope 2 of the laser endoscope device 1A has roughly the same configuration as that of the endoscope 2 shown in the first embodiment and includes the inner tube 12 and the outer tube 13, which surrounds part of the outer surface of the inner tube 12. A linear-motion actuator is attached to the inner tube 12, and the inner tube 12 is movable relative to the outer tube 13 in the axial direction X. An ultrasonic motor is further attached to the inner tube 12, and the inner tube 12 is revolvable relative to the outer tube 13 over 360°. The action of the inner tube 12 in the axial direction X or the revolutional direction R is controlled by the control unit 50.

The endoscope of the laser endoscope device 1A according to the present embodiment further includes an angle detector 81, which detects the angle of the inner tube 12 in the revolutional direction R, and a linear scale 82, which detects the position of the inner tube 12 in the axial direction X. Since the endoscope 2 includes the angle detector 81 and the linear scale 82, the distance from a solitary lymphatic nodule to a lesion in the axial direction X and the angle between the solitary lymphatic nodule and the lesion in the revolutional direction R can be grasped with respect, for example, to the position of the solitary lymphatic nodule, so that the position of the lesion can be identified. Even in a case where no solitary lymphatic nodule is present, the position where the lesion is present can be characterized with respect to a predetermined position, for example, the anus in the case of the large intestine, and the mouse in the case of the stomach.

As described above, according to the laser endoscope device 1A, a coordinate reference can be provided in a panoramic image, whereby the position where a lesion is present in the digestive tract 112 can be visualized and grasped. Further, the coordinate reference can show evidence that the 360°-revolution imaging has been performed, whereby the fact that the acquired image is a full-circumference image with no missing part can be presented to the patient.

(Finding 3 on which Present Invention is Based)

The finding 3, on which the present invention is based, and a primary configuration of the invention associated with the finding 3 will next be described.

The finding 3 will be described with reference to a case where a cell morphology in a living body is imaged under the multiphoton laser microscope (FV1000MPE manufactured by Olympus Corporation) while changing the focal point position and a plurality of captured images are cut in a predetermined position to create a cross-sectional image (tomographic image). A laboratory mouse was used as the living body.

FIGS. 34A, 34B, and 34C show images illustrating the cell morphology over a predetermined depth range from the inner wall surface (mucosa surface), specifically, three-dimensional data images obtained by performing imaging at 2-μm intervals from the mucosa surface (depth 0) to a depth of 150 μm and layering the captured 75 images in total on each other. In each of FIGS. 34A to 34C, the section (a) shows an image of the cell group in a plan view viewed in the direction perpendicular to the inner wall surface 113, the section (b) shows a cross-sectional image of the section (a) taken along the line b-b, and the section (c) shows a cross-sectional image of the section (a) taken along the line c-c.

As the stain for staining the cell group, both the stain containing curcumin and the stain containing Acid Red (red #106) were used. The staining period was set at 5 minutes. The staining period is the period for which the stain is caused to be in contact with the cell group and the dye of the stain is allowed to penetrate into the cells themselves or the gaps between the cells.

FIGS. 34A to 34C show images obtained by imaging the same cell group at the same time and filtering the images to extract different colors (wavelengths). FIG. 34A shows images representing the extracted color region stained both with the curcumin dye and the Acid Red dye. FIG. 34B shows images representing the extracted color region stained with the curcumin dye. FIG. 34C shows images representing the extracted color region stained with the Acid Red dye. FIGS. 34A to 34C show monochromatic images that are inherently color images, and the difference in the tendency of the staining performed by the stains causes the region stained with the curcumin dye to be displayed in a green fluorescent color and the region stained with the Acid Red dye to be displayed in a pale red or near orange fluorescent color, whereby the difference in color is more distinctively expressed.

FIGS. 34A to 34C show cancer tissue and healthy mucosa tissue and indicate that the dyes differ from each other in terms of permeability.

The curcumin dye shows higher permeability in the cancer tissue than in the healthy mucosa tissue, as shown in FIG. 34B. Specifically, in the case of the curcumin dye, the depth to which the tissue is stained is about 40 μm in the cancer tissue, whereas the depth is about 20 μm in the healthy mucosa tissue.

The Acid Red dye shows lower permeability in the cancer tissue than in the healthy mucosa tissue, as shown in FIG. 34C. Specifically, in the case of the Acid Red dye, the depth to which the tissue is stained is about 40 μm in the cancer tissue, whereas the depth is about 70 μm in the healthy mucosa tissue.

As described above, the permeability of a dye varies depending on whether the cell morphology is cancer tissue or healthy mucosa tissue. It is believed based on the characteristic described above that measurement of the depth to which a cell group displayed in a cross-sectional image is stained allows identification of the cell group, a healthy cell group or a cancer cell group. A third embodiment based on the finding 3 will be described below.

Third Embodiment

The configuration of a laser endoscope device 1B according to the third embodiment will be described with reference to FIG. 35. FIG. 35 is a block diagram showing the control configuration of the laser endoscope device 1B.

The laser endoscope device 1B has roughly the same configuration as that of the laser endoscope device 1 shown in the first embodiment and includes the imaging unit 10, which includes the endoscope 2, and the control unit 50, the image processing unit 70, the laser oscillator 60, and the optical part 65.

The laser endoscope device 1B further includes the stain supplier 40 (see FIG. 12), which supplies a stain into a living body. In the present embodiment, double staining, in which cell groups in a living body are selectively stained in at least two different chromatic colors in accordance with the type of cells, is employed.

The imaging unit 10 applies laser light to a stained cell group and changes the focal point position (from 0 to 1000 μm, for example) to image a plurality of imaging regions P at different depths. The image processing unit 70 places the plurality of images obtained by the imaging performed by the imaging unit 10 in correspondence with the focal point position to generate a stereoscopic image. The generated stereoscopic image is cut at a predetermined on-image position containing the stained cell group to generate a cross-sectional image of the stained cell groups.

The control unit 50 evaluates whether the cell group displayed in the cross-sectional image is suspicious of a lesion based on the depth to which the cell group has been stained. For example, when the depth to which the cell group has been stained with the curcumin dye is (at least 1.5 times, for example) greater than the depth to which the healthy mucosa tissue has been stained, the control unit 50 determines that cancer cells have developed, whereas when the two depths are similar to each other (difference is smaller than 1.5 times, for example), the control unit 50 determines that no cancer cells have developed. Further, when the depth to which the cell group has been stained with the Acid Red dye is (at least 0.6 times, for example) smaller than the depth to which the healthy mucosa tissue has been stained, the control unit 50 determines that cancer cells have developed, whereas when the two depths are similar to each other (difference is at least 0.6 times, for example), the control unit 50 determines that no cancer cells have developed. It is noted that after whether or not cancer cells are present is evaluated based, for example, on single or double staining, the evaluation described above based on a cross-sectional image increase the reliability of the overall evaluation.

The laser endoscope device 1B according to the present embodiment includes the imaging unit 10, which includes the imaging head 11, which is inserted into a living body, and images the living body by applying the laser light to the living body via the imaging head 11, the control unit 50, which controls the operation of the imaging head 11, and the image processing unit 70, which processes an image captured by the imaging unit 10. The imaging head 11 includes the objective lens 16 and the focal point changer 18 capable of changing the focal point position of the objective lens 16 in the depth direction of the living body. The control unit 50 causes the focal point changer 18 to operate to change the focal point position, and the imaging unit 10 images a plurality of imaging regions P at different depths as the focal point position is changed. The image processing unit 70 then cuts the plurality of images obtained by the imaging performed by the imaging unit 10 at a predetermined position to generate a cross-sectional image of the interior of the living body.

Generation of a cross-sectional image by using the laser endoscope device 1B allows evaluation of whether or not tissue is cancerous also in the depth direction in the living body. In a case where the examination and diagnosis are performed in separate opportunities, the image processing unit only needs to display a currently captured image and relies on another device in terms of generation of a panoramic image and a stereoscopic image, whereby the burden on the endoscope device can be reduced.

(Findings 4, 5, and 6 on which Present Invention is Based)

The findings 4, 5, and 6, on which the present invention is based, and a primary configuration of the invention associated with the findings 4, 5, and 6 will next be described.

The finding 4 will first be described with reference to a case where living cells are placed in a tray and imaged under the multiphoton laser microscope (FV1000MPE manufactured by Olympus Corporation). Living tissue extracted from the interior of a human body was used as the living cells.

FIGS. 36A, 36B, and 36C show images illustrating a cell morphology in a position below the inner wall surface (mucosa surface) 113 at a depth of 50 μm.

As the stain for staining the cell group, both the stain containing curcumin and the stain containing Acid Red (red #106) were used. The staining period was set at 5 minutes. In the imaging, the living cells to be imaged were set at a temperature roughly equal to the body temperature (37° C.)

FIGS. 36A to 36C show images obtained by imaging the same cell group at the same time and filtering the images to extract different colors (wavelengths). FIG. 36A shows an image representing the extracted color region stained with the curcumin dye. FIG. 36B shows an image representing the extracted color region stained with the Acid Red dye. FIG. 36C shows an image representing the extracted color region stained with both the curcumin dye and the Acid Red dye. FIGS. 36A to 36C show monochromatic images that are inherently color images, and the difference in the tendency of the staining performed by the stains causes the region stained with the curcumin dye to be displayed in a green fluorescent color and the region stained with the Acid Red dye to be displayed in a pale red or near orange fluorescent color, whereby the difference in color is more distinctively expressed.

In FIGS. 36A to 36C, the region indicated with the arrow I is a region where the nuclei 135 of the glandular cells 131 are arranged in one row along the basement membrane 137, which means that the glandular cells 131 are healthy cells. In contrast, the regions indicated with the arrows II are each a region where two nuclei 135 are present between the center (lumen) of the gland 130 and the basement membrane 137. The regions indicated with the arrows II are not malignant tumor but are regions that each starts transforming into a cancerous region.

FIG. 37 shows a stomach cancer cell group stained with the curcumin dye. In the cancer cell group, the glands 130 or the nuclei 135 in the glandular cells 131 cannot be identified, as shown in FIG. 37.

As described above, imaging the stained cell group under the multiphoton laser microscope allows clear grasp of the forms of the glands 130, the basement membranes 137, the glandular cells 131, and the nuclei 135 below the inner wall surface (mucosa surface) 113 at depths greater than or equal to 10 μm but smaller than or equal to 1000 μm. Grasp of the arrangement of the nuclei 135 in the glandular cells 131, the distances between the basement membrane 137 and the nuclei 135, the shape and size of the nuclei 135, and other factors allows accurate pathological diagnosis of whether or not cancerous tissue is developing.

On the other hand, a multiphoton laser microscope is typically expensive, and it is desirable to develop a method that allows pathological diagnosis reasonably priced for a patient. To this end, the present inventors have attempted to grasp the cell morphology under a confocal laser microscope. In the case of living body staining in which living body dye is applied on a mucosa surface, an example in which the tissue of the inner wall surface (mucosa surface) itself is imaged under a confocal laser microscope has been reported, but there is no case in the past where a cell group below the inner wall surface 113 at a depth of 20 μm or deeper is imageable.

The finding 5 will be described with reference to a case where a cell morphology in a living body is imaged under the confocal laser microscope (FV1000 manufactured by Olympus Corporation). A laboratory mouse, was used as the living body.

As the stain for staining the cell group, the stain containing curcumin was used. The staining period was set at 5 minutes, which is longer than the staining period in related art. The staining period is desirably longer than or equal to 3 minutes but shorter than or equal to 20 minutes. The reason for this is that a staining period shorter than 3 minutes does not allow the stain to penetrate into the cell tissue, and that a staining period linger than 20 minutes causes the entire cells to be stained, resulting in a difficulty in distinction between a cancer cell group and a healthy cell group.

FIG. 38 shows an image of a cell group in a living body captured along the direction perpendicular to the inner wall surface (mucosa surface) 113 under a confocal laser microscope. The depth of the imaging region P from the inner wall surface (mucosa surface) 113 is about 5 μm in the region indicated by the arrow III and about 10 μm in the region indicated by the arrow IV. In the region indicated by the arrow III, the cytoplasm 126 of each of the epithelial cells 121 is stained with the curcumin dye (green in actual color image). In the region indicated by the arrow IV, the cytoplasm 126 is stained with the curcumin dye, and the nuclei 125 of the epithelial cells 121 are expressed in black. Since the nuclei 125 have roughly the same size as that of the nuclei 125 in the other region, and the shapes of the nuclei 125 in the two regions do not differ from each other, it is shown that the region indicated by the arrow IV contains healthy cells.

FIG. 39 shows an image of a cell group in a living body captured obliquely left downward with respect to the inner wall surface (mucosa surface) 113 under the confocal laser microscope. The depth of the imaging region P is about 5 μm in the region indicated by the arrow V, about 10 μm in the region indicated by the arrow VI, and about 50 μm in the region indicated by the arrow VII. In the region indicated by the arrow V, the cytoplasm 126 of each of the epithelial cells 121 is stained with the curcumin dye (green in actual color image). In the region indicated by the arrow VI, the cytoplasm 126 is stained with the curcumin dye, and the nuclei 125 of the epithelial cells 121 are expressed in black. Since the nuclei 125 have roughly the same size as that of the nuclei 125 in the other region, and the shapes of the nuclei 125 in the two regions do not differ from each other, it is shown that the region indicated by the arrow VI contains healthy cells. In the region indicated by the arrow VII, the glandular cells 131 are stained with the curcumin dye and can therefore be visually recognized.

FIG. 40 shows an image of the cell group in the living body captured obliquely right downward with respect to the inner wall surface (mucosa surface) 113 under the confocal laser microscope. The depth of the imaging region P is about 5 μm in the region indicated by the arrow VIII, and about 30 μm in the region indicated by the arrow IX. In the region indicated by the arrow IX, the cytoplasm 136 of each of the glandular cells 131 is stained with the curcumin dye (green in actual color image), whereby the positions of the outer circumference of the gland 130 and the basement membrane 137 can be visually recognized. Further, the nuclei 135 of each of the glandular cells 131 are expressed in black. The plurality of nuclei 135 are arranged along the outer circumference of the basement membrane 137 with a roughly fixed distance to the outer circumference maintained. The fact that the nuclei 135 are regularly arranged in each of the glands 130 as described above shows that the region indicated by the arrow IX contains healthy cells.

FIG. 41 shows an image of the cell group in the living body captured obliquely left downward with respect to the inner wall surface (mucosa surface) 113 under the confocal laser microscope. The depth of the imaging region P is about 5 μm in the region indicated by the arrow X, about 30 μm in the region indicated by the arrow XI, and about 60 μm in the region indicated by the arrow XII. In the region indicated by the arrow XI, the cytoplasm 126 of each of the glandular cells 131 is stained with the curcumin dye (green in actual color image), whereby the positions of the outer circumference of the gland 130 and the basement membrane 137 can be visually recognized. The plurality of arrowed nuclei 135 are arranged along the outer circumference of the basement membrane 137 with a roughly fixed distance to the outer circumference maintained. The fact that the nuclei 135 are regularly arranged in each of the glands 130 as described above shows that the region indicated by the arrow XI contains healthy cells. In the region indicated by the arrow XII, the capillaries 132 are heavily stained with the curcumin dye.

As described above, even a confocal laser microscope allows evaluation of whether an examination target is suspicious of a lesion by appropriately adjusting the focal point position and setting the staining period and based on the sizes of the nuclei 125 and 135, the state of the arrangement of the nuclei 125 and 135, and whether the distances between the nuclei 135 and the basement membrane 137 are uniform.

The finding 6 will be described with reference to another case where a cell morphology in a living body is imaged under the confocal laser microscope (FV1000 manufactured by Olympus Corporation). A laboratory mouse was used as the living body. The staining period for which the living cells are stained with a stain was set at 5 minutes.

Further, as a stain for staining a cell group, a stain containing curcumin solved in an optimized method was used.

First of all, even when a cell group can be stained, staining unevenness occurs, and it is therefore difficult to acquire an image of a uniformly stained living body. The present inventors have studied whether there are solvents that can replace water and found that curcumin is readily solvable in glycerol, which is tertiary alcohol, and ethanol, which is primary alcohol. Curcumin, in particular, is solved by about 5% in a 100% glycerol liquid or a 50%-glycerol and 50%-ethanol mixture liquid. Therefore, the 5%-curcumin solution is diluted and used in the living body staining. Specifically, the 5% solution was stored as a stock liquid, and the stock liquid was diluted with a physiological saline solution by a factor ranging from 10 to 1000, and the resultant liquid was used to stain a living body. The optimized solving method allowed a high-definition cell image shown below to be obtained.

FIG. 42 is an image of living cells stained with a stain solved by using the optimized solving method and captured with the confocal laser microscope. In FIG. 42, the section (a) shows an image of healthy large intestine mucosa, and the section (b) shows an image showing colorectal cancer. The depth of the imaging region is about 50 jam below the mucosa surface.

In the healthy large intestine mucosa shown in the section (a) of FIG. 42, the shape, size and arrangement of the nuclei 135 are roughly uniform, and the distances between the nuclei 135 and the basement membrane 137 are also roughly fixed, such as those in the regions indicated by the arrows XIII. The nuclei are each drawn in the form of a sesame-seed-shaped dark portion. The distribution pattern of the structure (crypts) of the glands 130 is roughly uniform, such as the structure in the regions indicated by the arrows XIV. The crypts are each expressed in the form of a dark portion in the vicinity of the center of the broken-line circle. The capillaries 132 show a regular traveling pattern around the crypts.

On the other hand, in the large intestine shown in the section (b) of FIG. 42, the shape, size, and the arrangement of the nuclei of the glandular cells are non-uniform, and the distances between the nuclei of the glandular cells and the basement membrane are also non-uniform. Further, no gland structure (crypts) is recognized, and the capillaries are poor in traveling regularity because no crypt is present. The on-image analysis of the regularity of the nuclei and crypts allows tremendous improvement in the cancer pathological diagnosis accuracy and speed. For example, a rough center of each of the nuclei or the crypts are determined based on an image, the determined centers are connected to each other with line segments, and the lengths of the line segments are compared with each other for detection of disorder of the regularity. Further, the disorder of the regularity can also be detected by determining the areas of the regions surrounded by the line segments. The detected disorders of the regularity may be grouped, or the distribution of the disorders may be graphed to help final diagnosis performed by a medical doctor by indicating a group that does not fall within a certain range as a group suspicious of cancer. These tasks can be done in a short period.

Optimizing the solving method in living body staining using curcumin increased the loadability of the stain into cells and permeability of the stain into tissue and allowed cells to be stained with no unevenness, and the cell structure was successfully visualized even with the confocal laser microscope.

To determine the centers from images of the nuclei and crypts each having fixed-area out of those described above, the major and minor diameters are determined in a bitmap, the major and minor diameters are drawn in the form of line segments, and the intersections of the line segments can be used as the centers. A crypt having a shape close to a line segment can be so handled in the bitmap that the center of the line segment is the center of the crypt. Further, the regular arrangement of the nuclei around a crypt can be used to reduce the image area handled as the nuclei. The length of the line segment that connects centers adjacent to each other can be determined in the bitmap. Although the figures described above show monochromatic images, in an actual image, the fluorescence emitted from a stain can be used, and the dark portion can be determined also by using the color information. Further, since the glands shown in FIG. 10A can each be handled as a roughly circular image when the gland contains healthy cells, disorder in the regularity of the line segments that connect the centers of the glands with each other can be used to digitally determine disorder in the regularity. The calculation of the disorder of the regularity is processing a tremendous amount of data, but a computer can be used to detect the disorder in the regularity in a short period.

Embodiments based on the findings 4, 5, and 6 will be described below.

Fourth Embodiment

The basic configuration of a laser endoscope device 1C according to a fourth embodiment will next be described with reference to FIGS. 43, 44, and 45.

FIG. 43 is a schematic view showing a front-end-side end portion of the endoscope 2 of the laser endoscope device 1C in FIG. 45. FIG. 44 is a schematic view showing the entire endoscope 2. FIG. 45 is a block diagram showing the control configuration of the laser endoscope device 1C.

The laser endoscope device 1C includes the imaging unit 10, which includes the endoscope 2, the control unit 50, and the image processing unit 70, as shown in FIG. 45. The laser endoscope device 1C further includes the laser oscillator 60 and the optical part 65.

The laser endoscope device 1C further includes the stain supplier 40 (see FIG. 12), which supplies a stain into a living body. In the present embodiment, the stain described in the finding 5 or 6 described above is used.

Laser light L1 emitted from the laser oscillator 60C is reflected off a dichroic mirror 66C, which is an optical part 65C, further reflected off a mirror 19C in the endoscope 2, and applied to the living body. Living cells irradiated with the laser light L1 produce fluorescence, and the fluorescence is reflected off the mirror 19C, passes through the dichroic mirror 66C, and is detected with a photodetector 35C. The light detected with the photodetector 35C is converted into an electric signal, and the image processing unit 70 forms an image according to the electric signal. Since the color of the fluorescence changes in accordance with the stain, the photodetector 35C is formed of a plurality of photodetectors, and a color separation optical filter is disposed in a position on the upstream side of the photodetector 35C for color separation. The actions of the components described above and the functions and roles of each part are roughly the same as those shown in FIG. 15 but are distinguished therefrom by adding "C" to the numbers of the components of the confocal laser device because a confocal laser device differs in principle from a multiphoton laser device.

The laser oscillator 60C includes a plurality of types of wavelength changeable laser each capable of changing the wavelength stepwise over a wavelength range of 405 to 980 nm, and the wavelength is selected in accordance with the characteristics of a fluorescence reaction that occurs in a measurement target. The lasers may each operate in pulses or continuous oscillation. In the case of pulse operation, the operation frequency is at least several tens of kilohertz, and the duty ranges from 5% to 50%, and the frequency and duty ranges are so selected in consideration of the imaging sweep frequency that a sharp image is obtained. The laser light L1 in the present embodiment is confocal laser light, and the laser oscillator 60C uses, for example, a laser capable of emitting light having a wavelength of 405 nm and a power of 30 mW at the maximum. The power of the laser light emitted from the laser in the imaging operation ranges from 5 to 10 mW, but not necessarily. The laser oscillator 60C can adjust the intensity of the laser light L1 in accordance with the degree of staining and the degree of fluorescence.

A dichroic mirror 66C, which is the optical part 65, reflects light having the same wavelength as that of the laser light L1 and transmits light having the other wavelengths. The laser light L1 emitted from the laser oscillator 60C is therefore reflected off the dichroic mirror 66C toward the mirror 19C. On the other hand, the fluorescence produced in the living cells is reflected off the mirror 19C, then passes through the dichroic mirror 66C, and reaches the photodetector 35C. The optical part 65C can instead be formed, for example, of a prism or a 4/λ plate.

The imaging unit 10 includes the endoscope 2 and the photodetector 35C and images the cell morphology in the living body with the laser light L1 applied to the interior of the living body.

The photodetector 35C detects the fluorescence produced when the laser light L1 is applied and converts the fluorescence into an electric signal according to the intensity of the fluorescence. The photodetector 35C can, for example, be a photomultiplier or a CCD semiconductor image sensor. A pinhole or any other component is provided as a part that provides the confocal laser function.

The endoscope 2 includes the inner tube 12 and the outer tube 13, which surrounds part of the outer surface of the inner tube 12, as shown in FIG. 44. The inner tube 12 and part of the outer tube 13 are inserted into the living body. The inner tube 12 has a length, for example, of 50 mm and an outer diameter ranging from, for example, 3 to 10 mm. A linear-motion actuator is attached to the inner tube 12, and the inner tube 12 is movable relative to the outer tube 13 in the axial direction X by about 25 mm. An ultrasonic motor is further attached to the inner tube 12, and the inner tube 12 is revolvable relative to the outer tube 13 over 360°. The action of the inner tube 12 in the axial direction X or the revolutional direction R is controlled by the control unit 50.

The imaging head 11 is provided at a front-end-side end portion of the inner tube 12 of the endoscope 2. The imaging head 11 is inserted along with the inner tube 12 into the living body in such a way that the imaging head 11 passes by the insertion tube 20, as shown in FIG. 43. The imaging head 11 is so controlled as to move in the living body based on the actions in the axial direction X and the revolutional direction R of the inner tube 12.

The imaging head 11 includes an objective lens 16C, the focal point changer 18, the spacer 17, and the mirror 19C.

The mirror 19C is a part that redirects the laser light L1 outputted from the laser oscillator 60C toward the objective lens 16C or redirects the fluorescence emitted from the living cells toward the photodetector 35C, as described above.

The objective lens 16C is so provided as to face the inner wall surface 113 of the living body. The objective lens 16 has, for example, a diameter of 10 mm, a magnification of 10 times, a resolution of 5 μm, and an imaging field of view of 3 mm×3 mm. The objective lens 16 instead has a diameter of 12 mm, a magnification of 40 times, a resolution of 10 μm, and a field of view of 7.5 mm×7.5 mm. The wider the imaging field of view, the better. The objective lens 16C may still instead be so configured that part of a lens having either of the diameters described above is cut or the diameter of the objective lens 16C is reduced to a value ranging from 3 mm to 5 mm so that the objective lens is readily inserted into the living body with the same resolution maintained.

The objective lens 16C may be so disposed as to incline with respect to the inner wall surface 113. Performing the imaging with the objective lens 16C inclining allows the cell morphology of the epithelium 120 and the gland 130 to be simultaneously imaged.

The focal point changer 18 is, for example, a piezoelectric actuator or an electromagnetic actuator and moves the objective lens 16C in the optical axis direction to change the position of the focal point of the objective lens 16C. The focal point changer 1R operates under the control of the control unit 50 and can adjust the focal point over a depth range from 0 to 75 μm below the inner wall surface (mucosa surface) 113. Changing the position of the focal point allows imaging of the state of the living body at a predetermined depth below the inner wall surface 113 of the digestive tract 112.

The spacer 17 has, for example, an annular shape and is provided around the space between the objective lens 16C and the inner wall surface 113. The spacer 17 is a part not only for preventing the objective lens 16C from coming into contact with the inner wall of the living body but for maintaining a fixed distance between the objective lens 16C and the inner wall surface 113. The distance between the objective lens 16C and the inner wall surface (mucosa surface) 113 is set at an appropriate value, for example, a value greater than or equal to 1 mm but smaller than or equal to 10 mm by exchanging the spacer 17 to another before the imaging starts or adding a distance changeable mechanism using an actuator or any other device. The control unit 50 controls the movement of the imaging head 11 (inner tube 12) with the spacer 17 being in contact with the inner wall surface 113 and maintains the fixed distance from the objective lens 16C to the inner wall surface 113.

The control unit 50 is formed, for example, of a CPU, a ROM, and a RAM. The control unit 50 controls the action of the imaging head 11 via the inner tube 12. Specifically, the control unit 50 controls the movement of the imaging head 11 not only in the circumferential direction along the inner circumference of the inner wall of the digestive tract 112 but in the tract longitudinal direction of the digestive tract 112 (along axis of digestive tract). The control unit 50 further changes the position of the objective lens 16C in the optical axis direction by controlling the action of the focal point changer 18 to control the position where the focus is achieved in the living body. The control unit 50 can further adjust the laser output by controlling the laser oscillator 60C.

The image processing unit 70 stores the converted electric signal (fluorescence intensity) from the photodetector 35C and the coordinate position of the imaging unit 10 sent from the control unit 50 with the electric signal and the coordinate position related to each other and processes the data on the fluorescence intensity and the coordinate position to generate a digital image. The generated digital image is, for example, displayed on a monitor, printed out, or recorded on a storage device. The coordinate position of the imaging unit 10 may be expressed, for example, in the form of the distance from a reference location on the patient (throat or anus, for example) and the angle of revolution of the imaging head 11.

The confocal laser endoscope device 1C according to the present embodiment includes the imaging unit 10, which includes the imaging head 11, which is inserted into a living body, and images the living body by applying the laser light to the living body via the imaging head 11, and the control unit 50, which controls the operation of the imaging head 11. The imaging head includes 10, the objective lens 16C, and the focal point changer 18, which is capable of changing the focal point position of the objective lens 10C in the depth direction of the living body, and the control unit 50 causes the focal point changer 18 to operate in such a way that the focal point position has a predetermined depth deeper than or equal to 10 μm but shallower than or equal to 100 μm (desirably deeper than or equal to 10 μm but shallower than or equal to 70 μm) below the surface of the mucosa in the living body. The imaging unit 10 applies the laser light to a cell group located in the living body and exposed to and stained with a stain that selectively stains the cell group in a chromatic color for at least 2 minutes, preferably 5 minutes or longer, and the imaging unit 10 images the stained cell group at a predetermined depth. A method for controlling the focal point with a fixed positional relationship between the objective lens 16C and the mucosa surface maintained will be described. Reference character 171 in FIG. 45 denotes a second laser oscillator, which emits continuous parallelized light as reference light, for example, having a wavelength of 680 nm and a power of about 5 mW. A beam splitter, a half-silvered mirror, or any other component causes the light from the second laser oscillator 171 to travel along the optical path of the light from the laser oscillator 60C. In FIG. 45, the optical path L2 of the light from the second laser oscillator 171 is drawn with a broken line slightly shifted from the optical path of the light from the laser oscillator 60C for ease of understanding. The reference light L2 described above travels roughly the same path as that of the laser light L1 for examination but travels along a different optical path beyond a beam splitter 173 and enters a focal point control optical unit 174. In a case where a cylindrical lens, a beam splitter, and other components change the focal point position of the objective lens 16C, the focal point control optical unit 174 has an optical part configuration capable of detecting the amount of change in the focal point position. Reference character 175 denotes a photodetector that is typically divided into 2 or 4 blocks. The light detected with the thus configured photodetector is converted, for example, with a differential amplifier into an electric signal proportional to a change in the positional relationship between the objective lens 16C and the mucosa surface. The control of the position of the objective lens described above is used, for example, in an optical disk device and is fully applicable to an endoscope device. To apply the control to an endoscope device, a point to be aware of is that the laser light L1 for imaging and the reference light L2 preferably have different wavelengths so that the two light beams are readily separated from each other. Separating the wavelengths of the two light beams by at least 100 nm achieves optical characteristics of the imaging system and the focal point control system that allow the two light beams to be satisfactorily separate from each other. In the case where the focal point control system described above is provided, applying bias voltage to the control system allows fine adjustment of the focal point position. Changing the bias voltage stepwise allows automatic control of the position where the laser light L1 is focused in the depth direction.

The transmittance or reflectance of the optical parts 11C, 35C; 65C, 66C, 172, 173, and 174 greatly depends on the wavelength of the laser light beams L1 and L2. Modularizing the optical parts in accordance with the wavelengths of the laser light beams and preparing a plurality of types of modules can therefore readily handle a situation in which the wavelengths of the laser light beams are changed in accordance with the stain to be used or a body site to be examined.

As described above, even when the confocal laser endoscope device 1C is used, a sufficient staining period allows acquisition of images at the depths deeper than or equal to 10 μm but shallower than or equal to 70 μm below the inner wall surface (mucosa surface) 113 of the living body. As a result, a lesion can be readily found, and selecting the wavelengths and the intensities of the laser light beams allows acquisition of images without load of the laser light on the patient.

OTHER EXAMPLES

The laser endoscope devices 1 to 1C according to the embodiments of the present invention have been described, but the present invention is not limited to the embodiments described above and variations thereof. For example, aspects in which the embodiments described above and variations thereof are changed as follows also fall within the scope of the present invention.

The above-mentioned embodiments have been described with reference to the case where the staining is performed with a stain, such as curcumin. On the other hand, visualization of a cell morphology over a depth range from 10 μm to 1000 μm below the mucosa surface and detection of cancer with no missing part based on a full-circumference panoramic image of the digestive tract are also achieved from an unstained digestive tract mucosa. Examples of the cell morphology may include the cytoplasm of individual cells, the shapes of nuclei, the pattern in accordance with which crypts of glands are arranged, and a capillary traveling pattern. The detection described above is achievable by the fact that a certain amount of fluorescence is emitted from flavin adenine dinucleotide (FAD), nicotinamide adenine dinucleotide (NAD), or any other chemical substance in a cell excited with laser light. This fact applies both to observation under a confocal laser microscope and to observation under a multiphoton laser microscope. A problem with the unstained digestive tract mucosa is, however, requirement of radiation of a large amount of excitation laser light, which is about 20 times greater than or equal to the amount of light necessary for imaging of a living body stained with curcumin or any other stain, and the large amount of excitation laser light could greatly damage the living cells. The damage can, however, be reduced by increasing the sensitivity of the detection system.

As another embodiment, FIG. 46 shows observation under the confocal laser microscope.

FIG. 46 shows images of inner planes of an unstained laboratory mouse colorectal mucosa captured under the confocal laser microscope. An image of the surface at an arbitrary location (a) and an image of the interior 10 μm below the surface at the location (b) are shown in the upper and lower sections in the left column. Further, an image of the surface at a location shifted by about 100 μm from the location described above (c) and an image of the interior 10 μm below the surface at the location (d) are shown in the upper and lower sections. An image (d), which is the combination of the images (b) and (d) of the interior 10 μm below the surface aligned with each other with the aid of the crypt arrangement pattern as an alignment mark, is further shown. The scale bars each represent 100 μm.

FIG. 47 shows observation under the multiphoton laser microscope.

FIG. 47 shows images of inner planes of the unstained laboratory mouse colorectal mucosa captured under the multiphoton laser microscope. An image of the surface at an arbitrary location (a) and an image of the interior 25 μm below the surface at the location (b) are shown in the left column. Further, an image of the surface at a location shifted by about 400 μm from the location described above (c) and an image of the interior 25 μm below the surface at the location (d) are shown in the right column. An image (e), which is the combination of the images (b) and (d) of the interior 25 μm below the surface aligned with each other with the aid of the crypt arrangement pattern as an alignment mark, is further shown. The operation described above can be continuously performed to generate a panoramic image. The arrow e1 in the image (b) and the star mark e2 in the image (d) correspond to the arrow e1 and the star mark e2 in the merged image (e), respectively. The scale bars each represent 100 μm. Further, in an image (f), which is the image (e) but captured at a zoom magnification of 2, the epithelial cells and the cytoplasm of the glandular cells appear bright. On the other hand, the nuclei 135 indicated by the arrows appear dark. The scale bar in the image (f) represents 100 μm.

As shown in FIG. 47, even in the case of unstained cells, the cancer detection method described in the embodiments in which cells are stained with curcumin or any other stain can be used as long as nuclei or crypts can be grasped in an image. The detection may be based on comparison in terms of shape and brightness of the cells or may be comparison in terms of line segments created by using the nuclei or crypts in the image or the area surrounded by the line segments.

For example, in the embodiments of the present invention, to perform double staining, two types of stain are sequentially used for the double staining, but not necessarily. A plurality of dyes may be mixed with one another in advance to produce a mixed stain containing the plurality of dyes, and the mixed stain may be used to perform simultaneous staining.

In the embodiments of the present invention, a living body is stained in double staining using stains of two colors before the imaging, but not necessarily. A living body may be stained in a multi-staining using stains of at least two colors before the imaging.

For example, in a case where a cell group in a living body is stained in multi-staining using stains of at least three colors, the following method may be used. First, a stain A containing a dye A1 is used to stain the cell group, and the stain A is then recovered. A stain B containing a dye B1 is then used to stain the cell group, and the stain B is then recovered. A stain C1 containing a dye C1 is then used to stain the cell group, and the stain C1 is then recovered. The cell group can thus be stained in multi-staining. In this case, each of the stains reliably comes into contact with the cell group, whereby the cells are stained with improved reliability.

Another method for performing multi-staining may include producing a mixture liquid ABC, which is a mixture of a plurality of dyes A1, B1, and C1 mixed with one another in advance and staining cells with the mixture liquid ABC. In this case, the staining can be performed in a short period.

Further, performing simplified staining before the examination using the laser endoscope device also falls within the scope of the present invention. The simplified staining is staining using a prescribed oral cleaning liquid containing a mucosa cleaning agent, a stain, or any other substance.

For example, in the embodiments of the present invention, multi-photon laser light is used as the laser light of the laser endoscope device 1, but not necessarily, and the confocal laser light 1C may be used.

The spacer 17 in the imaging head 11 in the embodiments of the present invention is not limited to an annular spacer. The spacer 17 may instead be a plurality of members so provided as to surround the space between the objective lens 16 and the inner wall surface 113 or may be a pair of members that sandwich the space between the objective lens 16 and the inner wall surface 113.

In a case where a living body undesirably moves when the interior of the living body is imaged, the control unit 50 may be used to control the focal point changer 18 to cause it to control the focal point, for example, by using the reference laser light described above for imaging with the focus maintained. Instead, the control unit 50 may use a wobble signal that drives the objective lens in a fixed cycle in accordance with a sinusoidal wave or a sawtooth wave with the wobble signal related to obtained images for imaging with the imaging position aligned with a desired position.

In the embodiments of the present invention, the imaging is performed while identifying the depth position below the inner wall surface (mucosa surface) 113 of the digestive tract 112, the depth information and the image information are stored with the two types of information related to each other, and the images captured at the same depth position are merged with each other to generate a merged image, but not necessarily. For example, a plurality of images different from one another in terms of depth position and imaging region P may be acquired without recognition of the depth position, and similar images or related images may be extracted from the plurality of images and merged with one another to generate a merged image.

In the embodiments of the present invention, cells in a living body are stained with a stain and then imaged by using the laser endoscope device 1, but not necessarily, and using the laser endoscope device based on multiphoton laser light allows imaging of the cell morphology in the living body with no staining of the cells with a stain. For example, when the cells are irradiated with the multiphoton laser light, a compound generally present in the cells (NAD: nicotinamide adenine dinucleotide, for example) or any other compound produces light having a wavelength half the wavelength of the multiphoton laser light in the cells, and the produced light impinges on the NAD or any other compound, which then produces autologous fluorescence, whereby an image of the cell morphology in the living body can be acquired with no exogeneous staining.

The tract longitudinal direction (axial direction) of the digestive tract is not limited to a linear direction, and the present invention is applicable to a case where the tract longitudinal direction is a curved direction.

The laser endoscope devices 1 to 1C according to the embodiments of the present invention can also visualize luminal organs (such as bronchus, urinary bladder, and urinary duct) other than digestive tracts, and can further visualize the kidney, the liver, the brain, the retina, and other cell structures although there is a restriction on the visualized range of 1 mm or smaller in depth below the surface.

In the embodiments described above, the terms of laser microscope and laser endoscope are used. In a case where the epithelium or any other site is imaged and diagnosed, the laser microscope and laser endoscope are handled as an endoscope having a microscope function, and in a case where the digestive tract or any other internal organ is imaged and diagnosed, the laser microscope and laser endoscope are handled as an endoscope having a microscope function.

INDUSTRIAL APPLICABILITY

The laser endoscope devices according to the embodiments of the present invention are used to image or treat a lesion having developed in the digestive tract, the respiratory system, the renal/urinary system, the utero-ovarian reproductive system, the cerebrospinal nervous system, and other body sites over a wide range with no missing part.

REFERENCE SINGS LIST 1, 1A, 1B, 1C: Laser endoscope device
2: Endoscope
10: Imaging unit
11: Imaging head
12: Inner tube
13: Outer tube
15: Arm
16, 16C: Objective lens
17: Spacer
17a: Wheel
18: Focal point changer
19, 19C: Mirror
20: Insertion tube
21: First balloon
22: Second balloon
23: Pressing member
24: Support roller
25: Extension mechanism
26: Sliding member
27, 28: Joint mechanism
29: Gyro sensor
30: Pressure sensor
31: Extendable/shrinkable spacer
35, 35C: Photodetector
40: Stain supplier
42: Supply port
42a: Discharge port
43: Recovery port
45: Stain
50: Control unit
51: First focal point changeable mode
52: Second focal point changeable mode
60, 60C: Laser oscillator
65, 65C: Optical part
66, 66C: Dichroic mirror
70: Image processing unit
81: Angle detector 82: Linear scale
102: Multiphoton laser microscope
112: Digestive tract
113: Inner wall surface of digestive tract (mucosa surface)
113a: Protruding or recessed site
114: Axis of digestive tract
120: Epithelium
121: Epithelial cell
125: Nucleus of epithelial cell
126: Cytoplasm of epithelial cell
130: Gland
131: Glandular cell
132: Capillary
133: Connective tissue
135: Nucleus of glandular cell
136: Cytoplasm of glandular cell
137: Basement membrane
138: Crypt
152: Cancer cell population
160: Muscular layer of mucosa
A, B: Stain
P, P1, P2, P3: Imaging region
Pa, Pb: Region where imaging region overlap with each other
L: Laser light
R: Circumferential direction (revolutional direction)
S: Closed space
X: Axial direction

The invention claimed is:

1. A laser endoscope device comprising:
an imaging unit that includes an imaging head inserted into a living body and applies laser light to the living body via the imaging head to image the living body,
a control unit that controls the imaging head in such a way that it scans while keeping a fixed distance from a cell surface of the living body, and
an image processing unit that processes an image captured by the imaging unit,
wherein the imaging unit images a plurality of imaging regions to be imaged as the imaging head moves in such a way that adjacent imaging regions have identical portions, and
the image processing unit causes images of glands and/or crypts in the plurality of imaging regions to overlap with each other with the identical portions being aligned to generate a merged image.

2. A laser endoscope device comprising:
an imaging unit that includes an imaging head inserted into a living body and applies laser light to the living body via the imaging head to image the living body,
a control unit that controls the imaging head in such a way that it scans the entire inner circumference of the digestive tract while keeping a fixed distance from the inner wall surface of digestive tract of the living body and at the same time moves in the direction of circumference of the digestive tract, and
an image processing unit that processes an image captured by the imaging unit,
wherein the imaging unit images a plurality of imaging regions to be imaged as the imaging head moves in such a way that adjacent imaging regions have identical portions, and
the image processing unit causes the plurality of imaging regions to overlap with each other with the identical portions being aligned to generate a merged panoramic image of entire inner circumference in the imaging range moved in the direction of the circumference of the digestive tract.

3. The laser endoscope device according to claim 1, wherein the laser is multiphoton laser or confocal laser, the imaging head includes an objective lens and a focal point changer capable of changing a focal point position of the objective lens in a direction of depth from a cell surface of the living body,
the control unit changes the focal point position by operating the focal point changer,
the imaging unit images the imaging regions at a predetermined depth out of depths deeper than or equal to 10 μm but shallower than or equal to 1000 μm below an inner wall surface inside the living body, and
the image processing unit generates the merged image at the predetermined depth.

4. The laser endoscope device according to claim 1, wherein the imaging head includes
an objective lens so disposed as to face the living body, and
a spacer provided around a space between the objective lens and the living body, and
the control unit controls the movement of the imaging head in such a way that the spacer is in contact with the living body to maintain the fixed distance.

5. The laser endoscope device according to claim 1, comprising:
a stain supplier that supplies a stain into the living body for selectively staining a cell group inside the living body in a chromatic color,
wherein the control unit controls the imaging head in such a way that it revolves around an axis of digestive tract of the living body,
the imaging unit images a plurality of imaging regions to be imaged as the imaging head revolves in such a way that imaging regions adjacent to each other in the revolutional direction have identical portions, and
the image processing unit causes the plurality of imaging regions to overlap with each other with the identical portions being aligned to generate the merged image.

6. The laser endoscope device according to claim 1, comprising:
a stain supplier that supplies a stain into the living body for selectively staining a cell group inside the living body in a chromatic color, and
first and second balloons which are disposed in front of and behind the imaging head in the axial direction of digestive tract of the living body and expand to form a closed space inside the digestive tract,
wherein the stain supplier includes a supply port which supplies a fluid into the closed space and a recovery port which recovers the fluid flowing into the closed space,
the control unit controls the imaging head in the closed space in such a way that it revolves around an axis of the digestive tract,
the imaging unit images a plurality of imaging regions to be imaged as the imaging head revolves in such a way that imaging regions adjacent to each other in the revolutional direction have identical portions, and
the image processing unit causes the plurality of imaging regions to overlap with each other with the identical portions being aligned using the gland, the crypt or solitary lymphatic nodule in the imaging regions as marks to generate the merged image.

7. The laser endoscope device according to claim 5,
wherein the control unit controls the imaging head in such a way that it orbits around an axis of the digestive tract.

8. The laser endoscope device according to claim 7,
wherein the control unit controls the imaging head in such a way that it helically moves around the axis of the digestive tract.

9. The laser endoscope device according to claim 5,
wherein the control unit controls the imaging head in such a way that it moves along a tract longitudinal direction of the digestive tract,
the imaging unit images a plurality of imaging regions to be imaged as the imaging head moves in such a way that imaging regions adjacent to each other in the tract longitudinal direction have identical portions, and
the image processing unit causes the plurality of imaging regions to overlap with each other with the identical portions being aligned to generate the merged image in the tract longitudinal direction.

10. The laser endoscope device according to claim 5,
wherein the stain supplier supplies a stain that specifically stains cancer cells and a stain that specifically stains ordinary cells into the living body,
the imaging unit images a plurality of imaging regions at different depths as the focal point position is changed,
the image processing unit places the plurality of images obtained by the imaging performed by the imaging unit in correspondence with the focal point positions to generate a stereoscopic image of interior of the living body or a cross-sectional image of the stereoscopic image, and
the control unit determines degrees of cancer development based on the stereoscopic image or the cross-sectional image by comparing the penetration depth of the stain that specifically stains cancer cells with that of the stain that specifically stains ordinary cells.

11. The laser endoscope device according to claim 10,
wherein the control unit has a first focal point changeable mode in which the focal point position is changed by a first interval and a second focal point changeable mode in which the focal point position is changed by a second interval smaller than the first interval, and in a case where the imaging is performed in the first focal point changeable mode and a resultant image obtained by the imaging contains a portion suspicious of a lesion, the control unit performs the imaging in the second focal point changeable mode in a vicinity of a focal point position where the image of the portion suspicious of a lesion has been captured.

12. The laser endoscope device according to claim 11,
wherein the control unit stores an image of healthy cells having no lesion in advance and compares any of the images obtained in the first focal point changeable mode with the image of healthy cells in terms of at least one of shape and brightness to evaluate the suspicion of a lesion.

13. The laser endoscope device according to claim 1,
wherein in a case where the image obtained by the imaging unit contains cells having a lesion, the control unit increases power of the laser light as compared with power in the imaging and applies the laser light having the increased power to the cells having a lesion to remove the cells having a lesion.

14. The laser endoscope device according to claim 1, further comprising:
a stain supplier that supplies stains for staining a cell group in the living body in at least two selective chromatic colors different from each other in accordance with a cell type into the living body,
wherein the imaging unit images the cell group stained with the stains supplied from the stain supplier in the at least two colors.

15. The laser endoscope device according to claim 14,
wherein the stain is a stain containing a curcumin-based compound and Acid Red or two stains formed of a stain containing a curcumin-based compound and a stain containing Acid Red.

16. The laser endoscope device according to claim 14,
wherein the stain is a stain containing a curcumin-based compound and FastGreen FCF or two stains formed of a stain containing a curcumin-based compound and a stain containing FastGreen FCF.

17. A laser endoscope device according to claim 14,
wherein the stain is a stain containing RoseBengal that specifically stains a cancer cell surrounding cell group other than the cancer cells located around cancer cells among the cell groups inside the living body in a chromatic color.

* * * * *

UNITED STATES PATENT AND TRADEMARK OFFICE
CERTIFICATE OF CORRECTION

| | |
|---|---|
| PATENT NO. | : 11,140,318 B2 |
| APPLICATION NO. | : 15/999626 |
| DATED | : October 5, 2021 |
| INVENTOR(S) | : Mizoguchi et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 616 days.

Signed and Sealed this
Thirty-first Day of January, 2023

Katherine Kelly Vidal
*Director of the United States Patent and Trademark Office*